(12) United States Patent
Ferguson et al.

(10) Patent No.: US 7,341,573 B2
(45) Date of Patent: Mar. 11, 2008

(54) SAFETY SHIELD FOR MEDICAL NEEDLES

(75) Inventors: F. Mark Ferguson, Salt Lake City, UT (US); Jeremy W. Snow, North Salt Lake, UT (US); B. Chance Bagley, Roy, UT (US); Daniel K. Smith, Woods Cross, UT (US); David L. Thorne, Kaysville, UT (US)

(73) Assignee: Specialized Health Products Inc., Bountiful, UT (US)

( * ) Notice: Subject to any disclaimer, the term of this patent is extended or adjusted under 35 U.S.C. 154(b) by 384 days.

(21) Appl. No.: 10/877,725

(22) Filed: Jun. 24, 2004

(65) Prior Publication Data

US 2004/0236289 A1 Nov. 25, 2004

Related U.S. Application Data

(63) Continuation-in-part of application No. 10/322,288, filed on Dec. 17, 2002, now Pat. No. 7,004,927, and a continuation-in-part of application No. 10/202,201, filed on Jul. 23, 2002, now Pat. No. 6,902,546, which is a continuation-in-part of application No. 09/809,357, filed on Mar. 15, 2001, now Pat. No. 6,595,955.

(60) Provisional application No. 60/424,655, filed on Nov. 7, 2002.

(51) Int. Cl.
*A61M 5/178* (2006.01)

(52) U.S. Cl. .............................. 604/164.01

(58) Field of Classification Search ............... 604/263, 604/110, 192, 164.08
See application file for complete search history.

(56) References Cited

U.S. PATENT DOCUMENTS

| 1,436,707 A | 11/1922 | Gaschke |
| 4,332,323 A | 6/1982 | Reenstierna ............... 206/365 |
| 4,373,526 A | 2/1983 | Kling ....................... 128/215 |
| 4,762,516 A | 8/1988 | Luther ....................... 605/164 |
| 4,790,828 A | 12/1988 | Dombrowski ............. 604/198 |

(Continued)

FOREIGN PATENT DOCUMENTS

EP 0 702 972 B1 7/1995

(Continued)

*Primary Examiner*—Manuel Mendez
(74) *Attorney, Agent, or Firm*—Paul S. Evans; Kevin Laurence

(57) ABSTRACT

A medical needle shield apparatus is provided that includes a needle hub having an outer needle cannula extending therefrom. An inner needle is disposed for slidable movement with the outer needle cannula. At least one shield is extensible from a retracted position to an extended position to enclose a distal end of the inner needle. The shield includes a binding member disposed within the shield and defines binding surfaces that form an aperture configured for slidable receipt of the inner needle. The binding member includes at least one drag inducing member that engages the inner needle during slidable receipt to create a drag force. The drag force facilitates rotation of the binding member such that the binding surfaces engage the inner needle to prevent slidable movement. The binding member further includes a needle communicating surface extending therefrom that is engageable with the inner needle to prevent rotation of the binding member. A retainer extends transversely from the needle communicating surface for releasable engagement with the needle hub.

22 Claims, 47 Drawing Sheets

U.S. PATENT DOCUMENTS

| | | | | |
|---|---|---|---|---|
| 4,804,371 A | 2/1989 | Vaillancourt | | 604/198 |
| 4,826,490 A | 5/1989 | Byrne | | 604/198 |
| 4,832,696 A | 5/1989 | Luther | | 604/164 |
| 4,834,718 A | 5/1989 | McDonald | | 604/195 |
| 4,846,811 A | 7/1989 | Vanderhoof | | 604/263 |
| 4,917,669 A | 4/1990 | Bonaldo | | 604/164 |
| 4,929,241 A | 5/1990 | Kulli | | 604/263 |
| 4,931,048 A | 6/1990 | Lopez | | 604/110 |
| 4,944,725 A | 7/1990 | McDonald | | 604/164 |
| 4,950,252 A | 8/1990 | Luther | | 604/198 |
| 4,952,207 A | 8/1990 | Lemieux | | 604/164 |
| 4,964,854 A | 10/1990 | Luther | | 604/166 |
| 4,978,344 A | 12/1990 | Dombrowski | | 604/198 |
| 4,994,041 A | 2/1991 | Dombrowski | | 604/164 |
| 5,007,901 A | 4/1991 | Shields | | 604/110 |
| 5,049,136 A | 9/1991 | Johnson | | 604/198 |
| 5,051,109 A | 9/1991 | Simon | | 604/263 |
| 5,053,017 A | 10/1991 | Chamuel | | 604/192 |
| 5,059,180 A | 10/1991 | McLees | | 604/110 |
| 5,084,023 A | 1/1992 | Lemieux | | 604/167 |
| 5,084,030 A | 1/1992 | Byrne | | 604/198 |
| 5,085,648 A | 2/1992 | Purdy | | 604/198 |
| 5,127,905 A | 7/1992 | Lemieux | | 604/164 |
| 5,135,504 A | 8/1992 | McLees | | 604/164 |
| 5,147,327 A | 9/1992 | Johnson | | 604/198 |
| 5,171,229 A | 12/1992 | McNeil | | 604/192 |
| 5,183,468 A | 2/1993 | McLees | | 604/164 |
| 5,205,829 A | 4/1993 | Lituchy | | 604/164 |
| 5,215,528 A * | 6/1993 | Purdy et al. | | 604/164.08 |
| 5,300,045 A | 4/1994 | Plassche | | 604/263 |
| 5,312,371 A | 5/1994 | Dombrowski | | 604/198 |
| 5,322,517 A | 6/1994 | Sircom | | 604/198 |
| 5,328,482 A | 7/1994 | Sircom et al. | | |
| 5,334,158 A | 8/1994 | McLees | | 604/110 |
| 5,342,310 A | 8/1994 | Ueyama | | 604/110 |
| 5,344,408 A | 9/1994 | Partika | | 604/192 |
| 5,348,544 A | 9/1994 | Sweeney | | 604/192 |
| 5,411,486 A | 5/1995 | Zadini | | 604/198 |
| 5,417,659 A | 5/1995 | Gaba | | 604/110 |
| 5,419,766 A | 5/1995 | Chang | | 604/110 |
| 5,423,766 A | 6/1995 | Di Cesare | | 604/192 |
| 5,458,658 A | 10/1995 | Sircom | | 604/192 |
| 5,478,313 A | 12/1995 | White | | 604/110 |
| 5,487,733 A | 1/1996 | Caizza | | 604/110 |
| 5,531,704 A | 7/1996 | Knotek | | 604/192 |
| 5,533,974 A | 7/1996 | Gaba | | 604/110 |
| 5,538,508 A | 7/1996 | Steyn | | 604/192 |
| 5,549,570 A | 8/1996 | Rogalsky | | 604/198 |
| 5,558,651 A | 9/1996 | Crawford et al. | | |
| 5,562,624 A | 10/1996 | Righi | | 604/110 |
| 5,562,633 A | 10/1996 | Wozencroft | | 604/171 |
| 5,582,597 A | 12/1996 | Brimhall et al. | | 604/192 |
| 5,584,809 A | 12/1996 | Gaba | | 604/110 |
| 5,584,810 A | 12/1996 | Brimhall | | 604/110 |
| 5,584,818 A | 12/1996 | Morrison | | 604/197 |
| 5,599,310 A | 2/1997 | Bogert | | 604/164 |
| 5,601,532 A | 2/1997 | Gaba | | 604/110 |
| 5,601,536 A | 2/1997 | Crawford | | 604/263 |
| 5,611,781 A | 3/1997 | Sircom | | 604/164 |
| 5,662,610 A | 9/1997 | Sircom | | 604/110 |
| 5,683,365 A | 11/1997 | Brown | | 604/110 |
| 5,697,907 A | 12/1997 | Gaba | | 604/110 |
| 5,718,688 A | 2/1998 | Wozencroft | | 604/164 |
| 5,725,504 A | 3/1998 | Collins | | 604/165 |
| 5,749,856 A | 5/1998 | Zadini | | 604/162 |
| 5,853,393 A | 12/1998 | Bogert | | 604/165 |
| 5,879,337 A | 3/1999 | Kuracina | | 604/192 |
| 5,882,337 A * | 3/1999 | Bogert et al. | | 604/110 |
| 5,910,130 A | 6/1999 | Caizza et al. | | 604/110 |
| 5,911,705 A | 6/1999 | Howell | | 604/110 |
| 5,919,168 A | 7/1999 | Wheeler | | |
| 5,938,641 A | 8/1999 | Villanueva | | |
| 5,947,936 A | 9/1999 | Bonds | | |
| 5,951,515 A | 9/1999 | Osterlind | | 604/110 |
| 5,951,523 A | 9/1999 | Osterlind et al. | | |
| 5,964,731 A | 10/1999 | Kovelman | | |
| 5,980,488 A | 11/1999 | Thorne | | 604/110 |
| 6,001,080 A | 12/1999 | Kuracina | | 604/171 |
| 6,004,294 A * | 12/1999 | Brimhall et al. | | 604/164.08 |
| 6,010,487 A | 1/2000 | DeMichele et al. | | |
| 6,015,397 A | 1/2000 | Elson et al. | | |
| 6,022,366 A | 2/2000 | Schraga | | |
| 6,117,108 A * | 9/2000 | Woehr et al. | | 604/110 |
| 6,132,401 A | 10/2000 | Van Der Meyden | | 604/195 |
| 6,193,694 B1 | 2/2001 | Bell | | 604/192 |
| 6,203,527 B1 | 3/2001 | Zadini | | 604/110 |
| 6,210,373 B1 | 4/2001 | Allmon | | 604/192 |
| 6,221,047 B1 | 4/2001 | Greene et al. | | 604/164 |
| 6,280,419 B1 | 8/2001 | Vojtasek | | 604/192 |
| 6,287,278 B1 | 9/2001 | Woehr et al. | | 604/110 |
| 6,406,459 B1 | 6/2002 | Allmon | | 604/192 |
| 6,443,927 B1 | 9/2002 | Cook | | 604/110 |
| 6,443,929 B1 | 9/2002 | Kuracina et al. | | 604/192 |
| 6,585,704 B2 | 7/2003 | Luther et al. | | 604/263 |
| 6,595,955 B2 * | 7/2003 | Ferguson et al. | | 604/110 |
| 6,616,630 B1 | 9/2003 | Woehr et al. | | 604/110 |
| 6,623,458 B2 | 9/2003 | Woehr et al. | | 604/192 |
| 6,629,959 B2 | 10/2003 | Kuracina et al. | | 604/192 |
| 6,652,486 B2 * | 11/2003 | Bialecki et al. | | 604/110 |
| 6,682,510 B2 | 1/2004 | Niermann | | 604/263 |
| 7,004,927 B2 * | 2/2006 | Ferguson et al. | | 604/110 |
| 7,179,244 B2 | 2/2007 | Smith et al. | | |
| 2002/0099339 A1 | 7/2002 | Niermann | | 604/263 |
| 2002/0107483 A1 | 8/2002 | Cook | | 604/164.01 |
| 2002/0177813 A1 | 11/2002 | Adams et al. | | 604/164.07 |
| 2002/0177818 A1 | 11/2002 | Vaillancourt | | 604/198 |
| 2003/0036731 A1 | 2/2003 | Wilkinson et al. | | 604/198 |
| 2003/0114797 A1 | 6/2003 | Vaillancourt et al. | | 604/171 |
| 2003/0135157 A1 | 7/2003 | Saulenas et al. | | 604/110 |
| 2003/0144627 A1 | 7/2003 | Woehr et al. | | 604/110 |
| 2003/0195471 A1 | 10/2003 | Woehr et al. | | 604/164.08 |
| 2003/0195479 A1 | 10/2003 | Kuracina et al. | | 604/263 |
| 2003/0216687 A1 | 11/2003 | Hwang | | 604/110 |
| 2004/0010227 A1 | 1/2004 | Riesenberger et al. | | 604/110 |
| 2004/0049155 A1 | 3/2004 | Schramm | | |
| 2004/0078003 A1* | 4/2004 | Smith et al. | | 604/164.08 |
| 2004/0171995 A1 | 9/2004 | Niermann | | 604/263 |
| 2004/0181173 A1 | 9/2004 | Wilkinson | | 600/576 |
| 2007/0083167 A1 | 4/2007 | Smith et al. | | |

FOREIGN PATENT DOCUMENTS

| | | |
|---|---|---|
| EP | 0 750 915 A2 | 1/1997 |
| EP | 1 027 903 A1 | 8/2000 |
| EP | 1 110 571 A1 | 6/2001 |
| EP | 1 112 754 A1 | 7/2001 |
| EP | 1 374 772 A1 | 1/2004 |
| WO | WO 97/42989 | 11/1997 |
| WO | WO 01/10488 A1 | 2/2001 |
| WO | WO 01/56642 | 8/2001 |
| WO | WO 02/45786 A2 | 6/2002 |
| WO | WO 03/103757 A1 | 12/2003 |

* cited by examiner

SAFETY SHIELD FOR MEDICAL NEEDLES

CROSS-REFERENCE TO RELATED APPLICATIONS

This patent application is a continuation-in-part of U.S. Utility patent application Ser. No. 10/322,288, filed in the U.S. Patent and Trademark Office on Dec. 17, 2002 now U.S. Pat. No. 7,004,927 by Ferguson et al., which claims priority to U.S. Provisional Patent application Ser. No. 60/424,655, filed in the U.S. Patent and Trademark Office on Nov. 7, 2002 by Bagley et al., and U.S. Utility patent application Ser. No. 10/202,201, filed in the U.S. Patent and Trademark Office on Jul. 23, 2002 now U.S. Pat. No. 6,902,546 by Ferguson et al., which is a continuation-in-part of U.S. Utility patent application Ser. No. 09/809,357, filed in the U.S. Patent and Trademark Office on Mar. 15, 2001 now U.S. Pat. No. 6,595,955 by Ferguson et al., the entire contents of each of these disclosures being hereby incorporated by reference herein.

BACKGROUND

1. Technical Field

The present disclosure generally relates to safety shields for medical needles, and more particularly, to safety shields that protect a needle point of a medical needle.

2. Description of the Related Art

Problems associated with inadvertent needle sticks are well known in the art of blood sampling, percutaneous medication injection and other medical procedures involving use of medical needles. Significant attention has been focused on needle stick problems due to the contemporary sensitivity of exposure to AIDS, Hepatitis and other serious blood-borne pathogen exposures.

Procedures for removing a needle from a patient commonly require a technician to use one hand to place pressure at the wound site where the needle is being withdrawn, while removing the needle device with the other hand. It is also common practice for an attending technician to give higher priority to care for the patient than is given to disposal of a needle. In the case of typical needle devices without safety shields, such priority either requires the convenience of an available sharps container within reach or another means for safe disposal without leaving the patient's side. Providing adequate care while following safety procedures is often compounded by the patient's physical condition and mental state, such as in burn units and psychiatric wards. Under such conditions, it is difficult to properly dispose of a used needle while caring for a patient.

The widespread knowledge and history associated with needle care and disposal problems have resulted in numerous devices for preventing accidental needle sticks. Problems of current safety devices include difficulty of use and high cost due to their complexity and number of parts.

Other known devices employ sheaths that are spring activated, telescoping, pivoting, etc. These devices, however, may disadvantageously misfire or be cumbersome to activate. Further drawbacks of current devices include high manufacturing cost due to complexity and the number of parts. Thus, these type prior art devices may not adequately and reliably shield medical needle apparatus to prevent hazardous exposure.

Consequently, there remains a need to provide a more satisfactory solution for needle safety devices by overcoming the disadvantages and drawbacks of the prior art. Therefore, it would be desirable to provide a more adequate and reliable medical needle shield apparatus that employs a safety shield slidably movable along a medical needle to prevent hazardous exposure to a needle tip. Such a needle shield apparatus should be easily and reliably movable to shield a needle tip of a needle cannula.

SUMMARY

Accordingly, the present disclosure addresses a need for a medical needle shield apparatus which effectively and inexpensively protects a tip of a medical needle after use. The present disclosure resolves related disadvantages and drawbacks experienced in the art. More specifically, the apparatus and method of this invention constitute an important advance in the art of safety needle devices.

In one particular embodiment, a medical needle shield apparatus is provided in accordance with the principles of the present disclosure. The medical needle shield apparatus includes a needle hub having an outer needle cannula extending therefrom to a distal end. An inner needle is disposed for slidable movement with the outer needle cannula. At least one shield is extensible from a retracted position to an extended position to enclose a distal end of the inner needle. The shield includes a binding member disposed within the shield and defines binding surfaces that form an aperture configured for slidable receipt of the inner needle between the retracted position and the extended position.

The binding member includes at least one drag inducing member such that the member engages the inner needle during slidable receipt of the inner needle to create a drag force with the inner needle. The drag force facilitates rotation of the binding member relative to a longitudinal axis of the inner needle such that the binding surfaces engage the inner needle to prevent slidable movement of the inner needle in the extended position of the shield. The binding member further includes a needle communicating surface extending therefrom such that the needle communicating surface is engageable with the inner needle to prevent rotation of the binding member. A retainer extends transversely from the needle communicating surface for releasable engagement with the needle hub.

The binding member may be rotatable, relative to a longitudinal axis of the inner needle, between a non-binding orientation whereby the inner needle is slidable relative to the binding member and a binding orientation whereby the binding surfaces engage the inner needle to prevent slidable movement of the inner needle in the extended position of the at least one shield. The binding member may include one or more outwardly arcuate arms that extend to the needle-communicating surface.

The inner needle can be attached to a handle for manipulation thereof. The needle hub may define a hub slot configured for receipt of the retainer. The needle hub may be releasably mountable with a housing of the at least one shield. The medical needle shield apparatus may further include a plurality of shields.

The at least one drag inducing member may define a cavity that is substantially aligned with the aperture. The cavity is configured for slidable receipt of the needle to create the drag force with the needle. The binding member may include a substantially planar aperture plate that includes the binding surfaces that form the aperture. The at least one drag inducing member may include a pair of arms extending from the aperture plate. The arms can have curled end portions spaced apart from the aperture plate. The arms can include deflectable members.

The shield can include a housing that defines at least one blocking member extending from an interior surface thereof. The at least one blocking member can be engageable with the binding member for urging the binding member to a binding orientation. The aperture plate is axially movable for engagement with the at least one blocking member that causes rotation of the binding member to a binding orientation.

The medical needle shield apparatus may further include an external gripping element that encloses the at least one shield. The external gripping element supports the at least one shield for relative rotational movement therewith. The at least one shield can be supported for relative rotational movement by the external gripping element by at least one bearing.

In an alternate embodiment, the medical needle shield apparatus includes a shield being extensible from a retracted position to an extended position to enclose a distal end of the outer needle cannula. The shield defines a probe guide at a distal end thereof that is configured for receipt of a probe. The probe is configured for slidable movement with the outer needle cannula.

In another embodiment, the medical needle shield apparatus includes a needle hub having an outer needle cannula extending therefrom to a distal end. An inner needle is disposed for slidable movement with the outer needle cannula. A handle is attached to the inner needle and defines a flash chamber in communication with the inner needle. The flash chamber has a fitting that facilitates connection to a medical device. A shield is releasably mountable to the needle hub and extensible from a retracted position to an extended position to enclose a distal end of the inner needle. The handle is disposed adjacent the shield.

BRIEF DESCRIPTION OF THE DRAWINGS

The foregoing and other features and advantages of the present invention will be more fully understood from the following detailed description of the exemplary embodiments, taken in conjunction with the accompanying drawings in which.

DETAILED DESCRIPTION OF THE EXEMPLARY EMBODIMENTS

Figure 1:
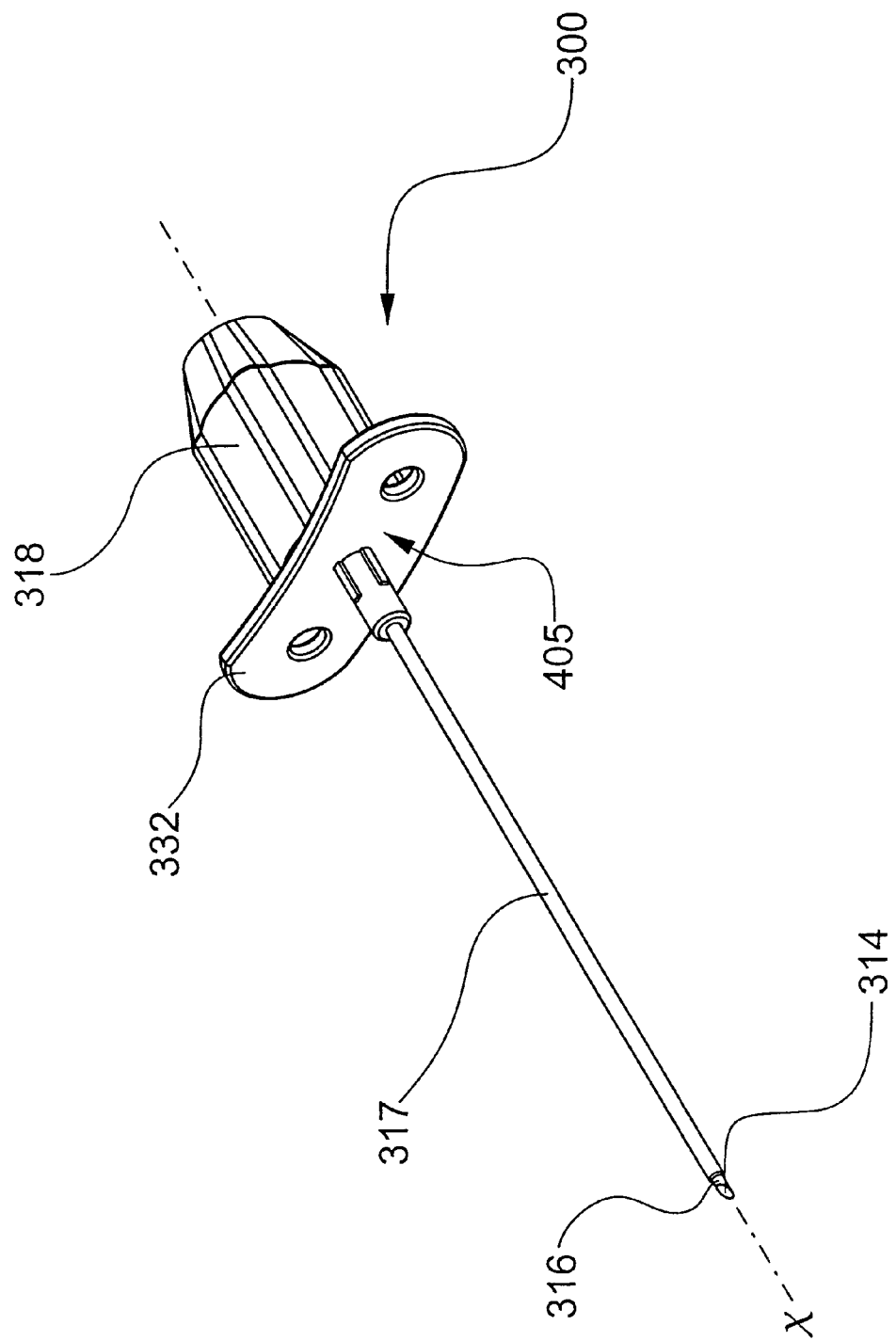
FIG. 1 is a perspective view of one particular embodiment of a medical needle shield apparatus in accordance with the principles of the present disclosure.

The exemplary embodiments of the medical needle shield apparatus and methods of operation disclosed are discussed in terms of medical needles for infusion of intravenous fluids, medication infusion or fluid collection, and more particularly, in terms of needle shield apparatus employed with a needle cannula that prevent hazardous exposure to the needle tip, including, for example, inadvertent needle sticks. It is envisioned that the present disclosure, however, finds application to a wide variety of cannula needles and devices for the infusion of preventive medications, medicaments, therapeutics, etc. to a subject, such as, for example, epidural needles, spinal needles, biopsy needles, chiba needles, potts cournand needles, etc. It is also envisioned that the present disclosure may be employed for collection of body fluids and/or tissues, including those employed during procedures relating to bone biopsy, phlebotomy, digestive, intestinal, urinary, veterinary, etc. It is contemplated that the medical needle shield apparatus may be utilized with other medical needle applications including, but not limited to, fluid infusion, fluid collection, catheters, catheter introducers, guidewire introducers, spinal and epidural, biopsy, aphaeresis, dialysis, blood donor, Veress needles, Huber needles, etc.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the medical needle shield apparatus. According to the present disclosure, the term "clinician" refers to an individual administering an infusion, performing fluid or tissue collection, installing or removing a needle cannula from a medical needle shield apparatus and may include support personnel.

The following discussion includes a description of the medical needle shield apparatus, followed by a description of the method of operating the medical needle shield apparatus in accordance with the present disclosure. Reference will now be made in detail to the exemplary embodiments of the disclosure, which are illustrated in the accompanying figures.

Turning now to the figures, wherein like components are designated by like reference numerals throughout the several views. Referring initially to FIGS. 1-8, there is illustrated a medical needle shield apparatus, constructed in accordance with the principals of the present disclosure. The medical needle shield apparatus includes a shield 300 that is extensible from a retracted position (FIG. 1) to an extended position (FIG. 4) to enclose a distal end 314 of a needle such as, for example, stylette 316 of a needle assembly. The needle assembly includes a hollow outer needle 317. Stylette 316 is slideably and concentrically disposed with needle 317 for employment therewith during a medical needle application, as will be discussed. A stylette handle 318 is connected to stylette 316 to facilitate manipulation thereof. Other needle assemblies are also contemplated, including for example, needle cannulae, guide wire/introducers, etc.

A binding member 364 is disposed within shield 300 and defines binding surfaces 368. Binding surfaces 368 form an aperture 366 configured for slidable receipt of stylette 316 between the retracted position and the extended position. Binding member 364 includes a drag inducing member, such as, for example, friction members 362 extending therefrom. Binding member 364 has a needle communicating surface 372 that is engageable with stylette 316 to prevent rotation of binding member 364.

Friction members 362 are configured for slidable engagement with stylette 316 between the retracted position and the extended position such that friction members 362 engage stylette 316 to create a drag force with stylette 316. It is envisioned that one or a plurality of friction members 362 may be employed.

Figure 4:
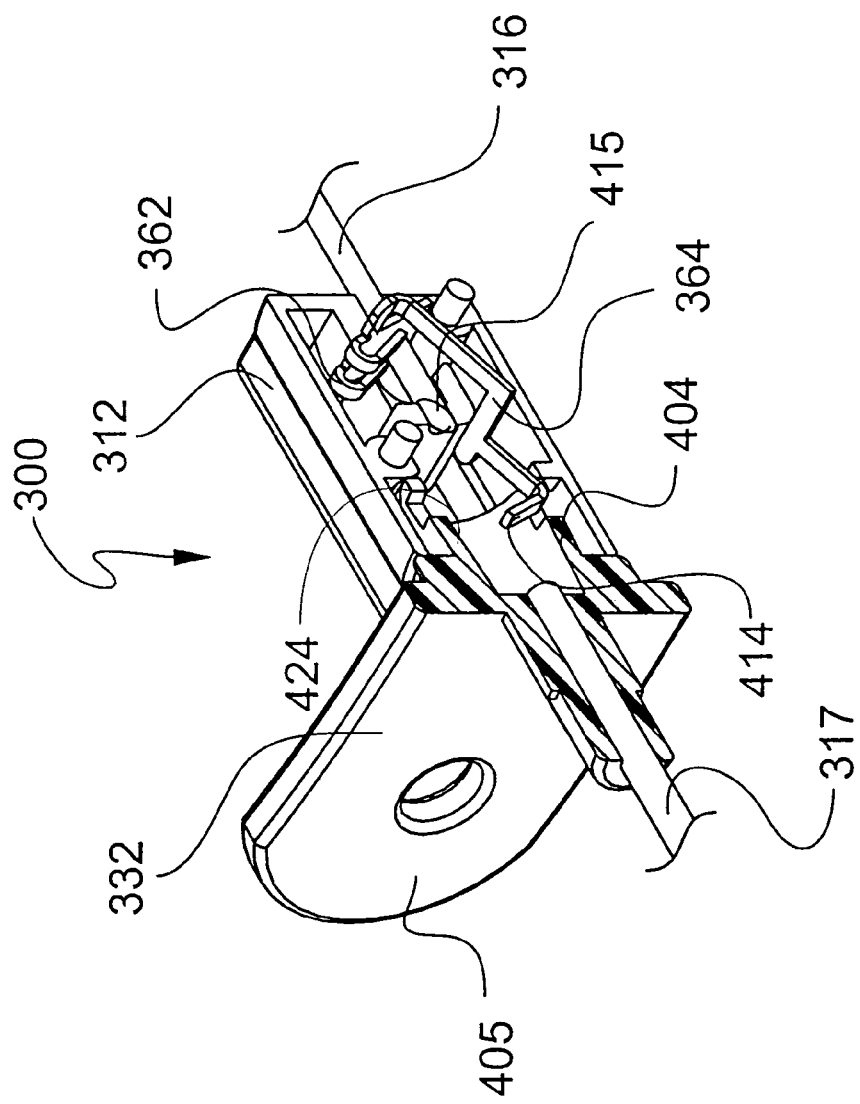
FIG. 4 is a cutaway perspective view of the shield, in a binding orientation, of the medical needle shield apparatus shown in FIG. 1 with the housing section removed.
Figure 5:
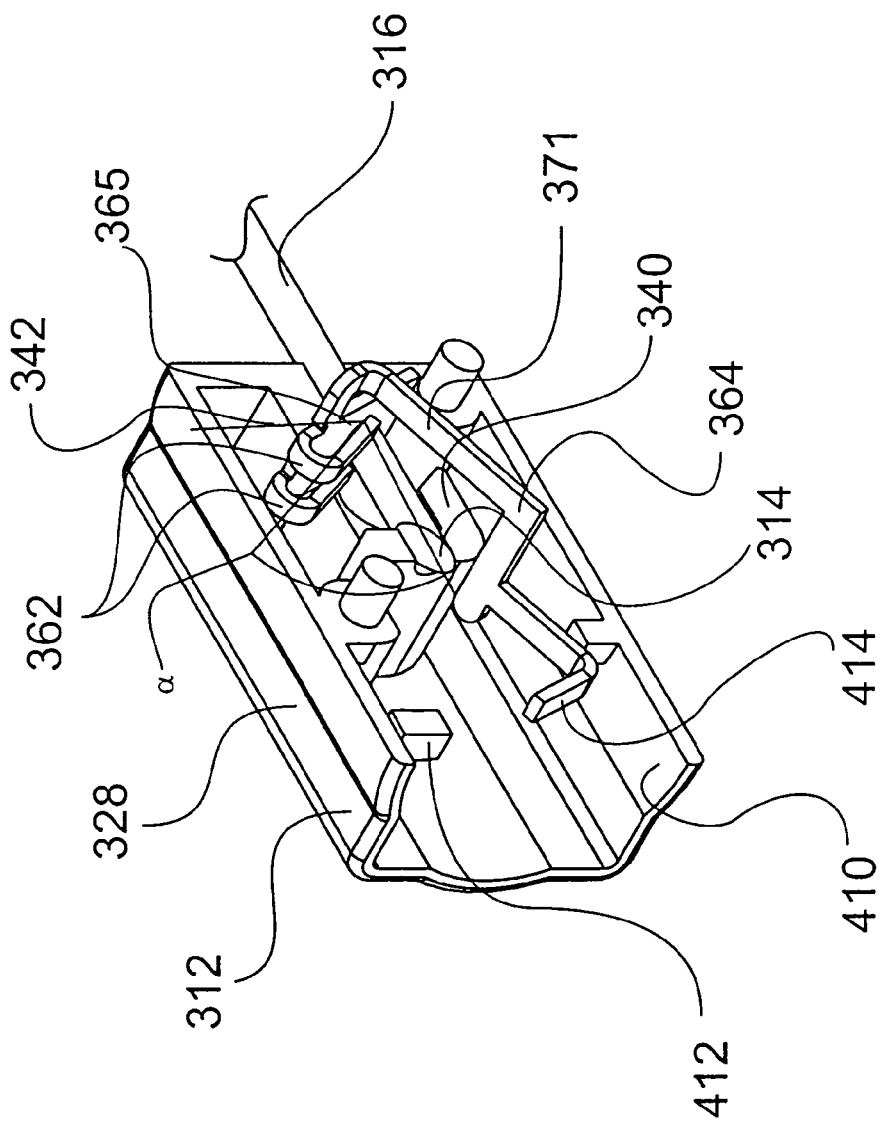
FIG. 5 is a cutaway perspective of the shield shown in FIG. 4 in a locked position.
Figure 6:
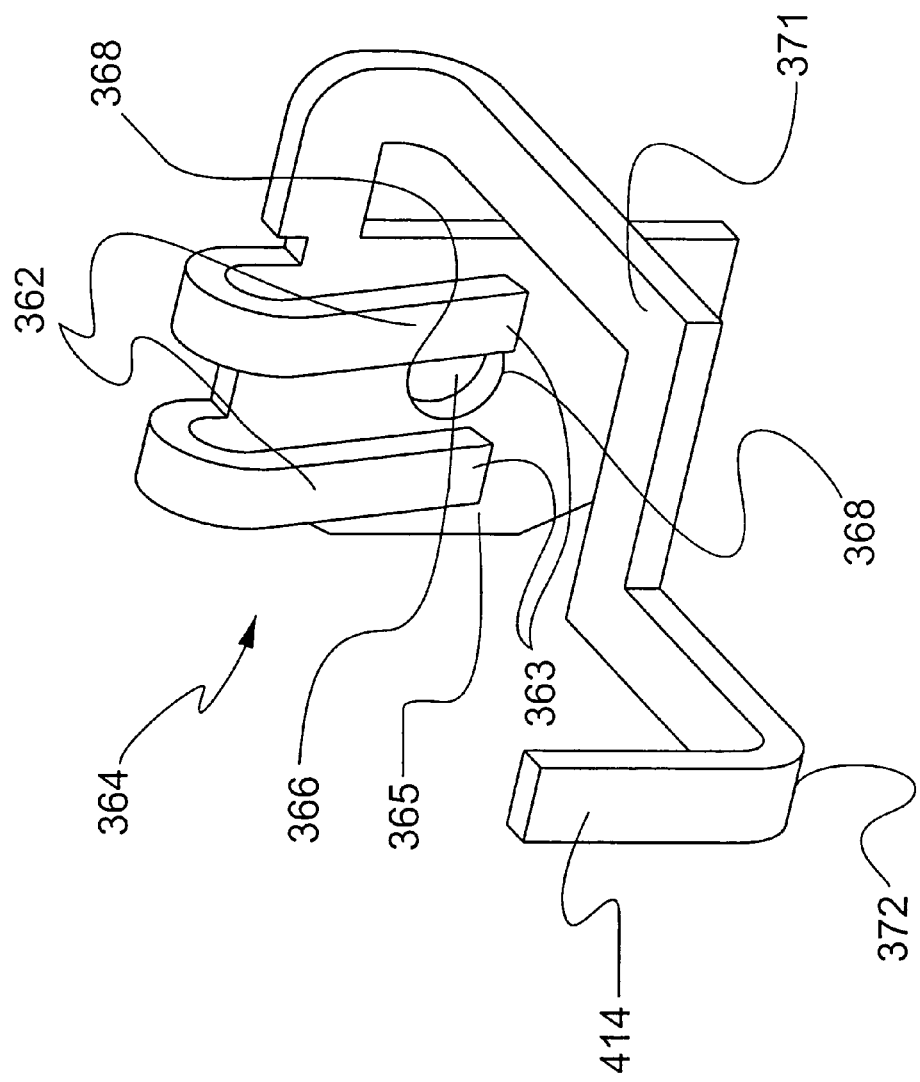
FIG. 6 is an enlarged perspective view of a binding member of the medical needle shield apparatus shown in FIG. 1.
Figure 7:
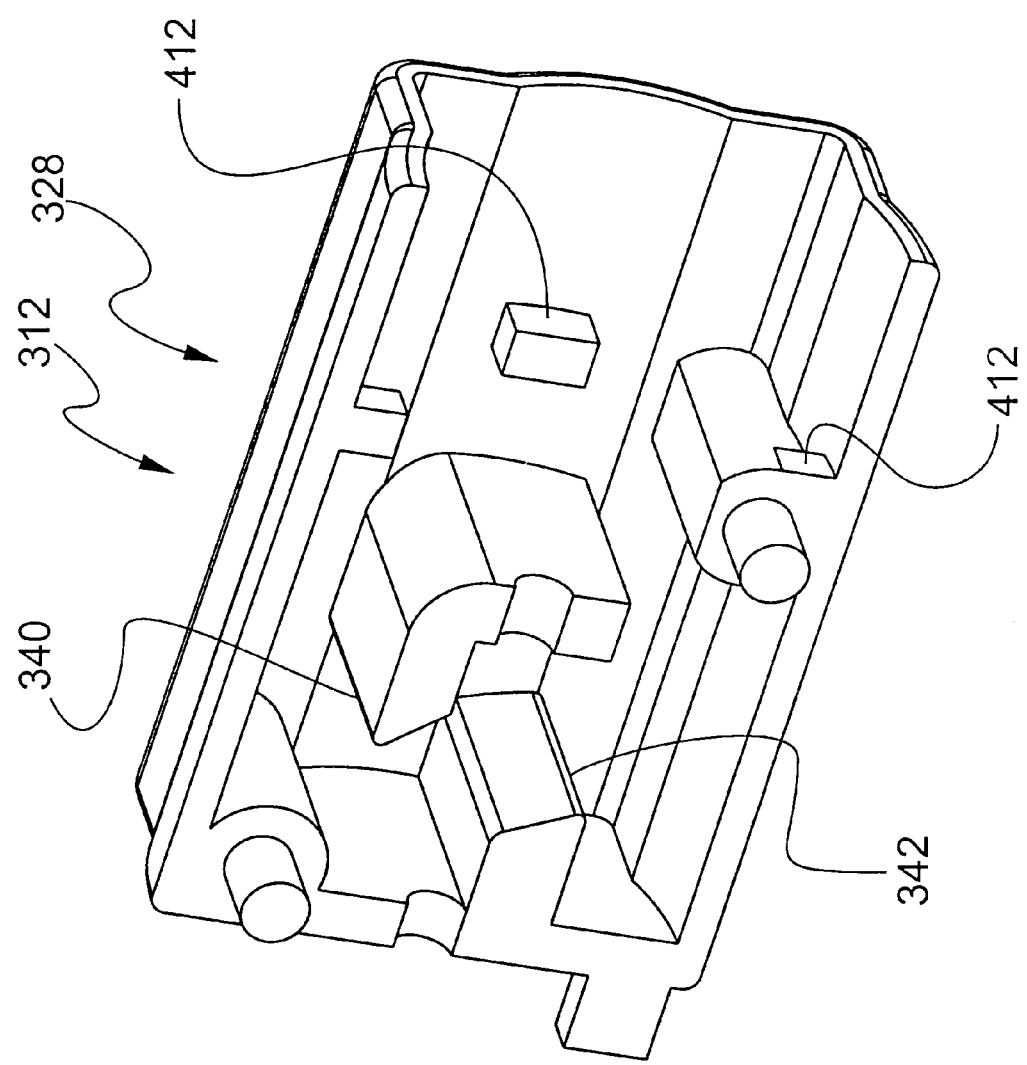
FIG. 7 is an enlarged perspective view of a housing section of the shield shown in FIG. 5.
Figure 8:
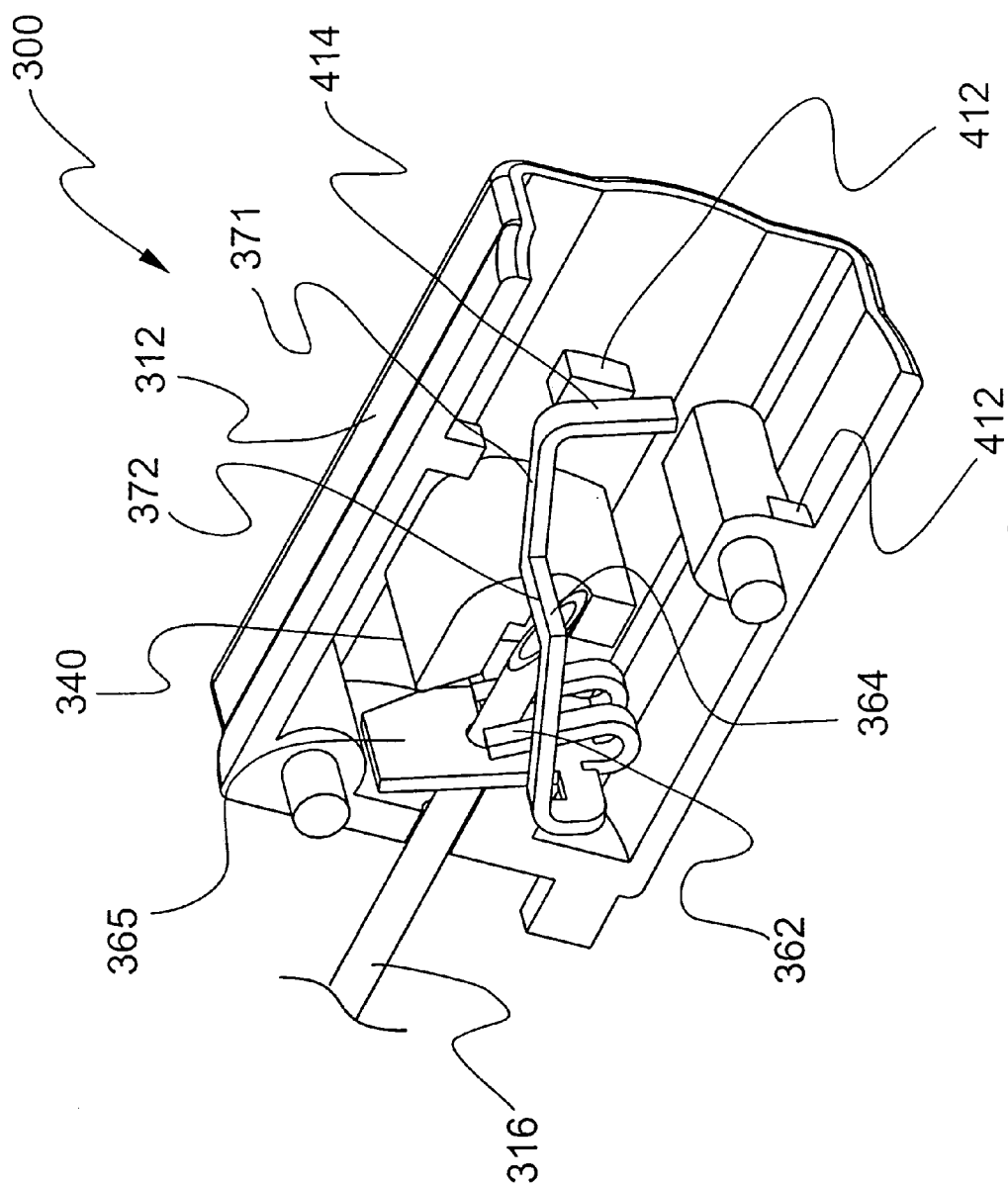
FIG. 8 is an alternate cutaway perspective view of the shield shown in FIG. 5.

The drag force in conjunction with one of blocking members 340 and/or 342, cause binding member 364 to move to a binding position (FIGS. 4 and 5). The force created by blocking members 340 and/or 342 acts in a direction opposite to the drag force. This causes a force couple, which moves binding member 364 to the binding position.

As stylette 316 is released from engagement with a needle communicating surface 372, binding member 364 and a retainer 414 move to the binding position. Rotation of binding member 364 is no longer opposed by engagement with stylette 316 at needle communicating surface 372. Thus, binding member 364, with retainer 414, is subject to inclination into the binding position. Rotation of binding member 364 causes binding surfaces 368 to frictionally engage stylette 316 to prevent movement thereof.

Blocking members 340 and/or 342 cause binding member 364 to move to the binding position as forces imposed on shield 300 cause relative movement thereof in either direction along longitudinal axis x. This maintains stylette 316 within shield 300 to avoid hazardous exposure to distal end 314. It is envisioned that needle communicating surface 372 may include ribs, projections, cavities, etc. for engagement with stylette 316 or that a portion of needle communicating surface 372 engages stylette 316.

The components of the medical needle shield apparatus can be fabricated from a material suitable for medical applications, such as, for example, polymerics or metals, such as stainless steel, depending on the particular medical application and/or preference of a clinician. Semi-rigid and rigid polymerics are contemplated for fabrication, as well as resilient materials, such as molded medical grade polypropylene. However, one skilled in the art will realize that other materials and fabrication methods suitable for assembly and manufacture, in accordance with the present disclosure, also would be appropriate.

Shield 300 includes a housing 312 that encloses binding member 364. Housing 312 includes a housing first section 328 and a housing second section 330. It is envisioned that housing sections 328, 330 may be variously configured and dimensioned such as, for example, rectangular, spherical, etc. It is further envisioned that housing sections 328, 330 may be joined by any appropriate process such as, for example, snap fit, adhesive, solvent weld, thermal weld, ultrasonic weld, screw, rivet, etc. Alternatively, housing 312 may be monolithically formed or integrally assembled of multiple housing sections and may be substantially transparent, opaque, etc. Housing sections 328, 330 may include ribs, ridges, etc. to facilitate manipulation of the medical needle shield apparatus.

In the retracted position, shield 300 is disposed adjacent to a needle hub 332 of outer needle 317. It is contemplated that outer needle 317 may also be comprised of a flexible, polymeric material, and that the components of the medical needle apparatus may be employed with other needle applications, such as, for example, catheters, guidewire introducers, such as a Seldinger needle, etc.

Binding member 364 may be monolithically formed and includes an aperture plate 365, frictional members 362, end sensing member 371, needle communicating surface 372 and retainer 414. It is contemplated that binding member 364 may include one or more frictional members 362. Aperture plate 365 has a rectangular, generally planar configuration with sufficient stiffness to produce forces for binding stylette 316, as will be discussed. It is envisioned that aperture plate 365 may have an arcuate surface, undulating, etc. It is further envisioned that aperture plate 365 may have various degrees of stiffness according to the requirements of a particular application.

Frictional members 362 may be monolithically formed with binding member 364 and extend from aperture plate 365 in association therewith for alignment with aperture 366 and engagement with stylette 316. Each frictional member 362 may include a flexible arm 363, which are spaced apart to facilitate sliding engagement with stylette 316. Such engagement creates a frictional drag force with stylette 316. This frictional drag force in conjunction with one of the blocking members 340 and/or 342 causes binding member 364 to move with stylette 316, which generates a canting force and inclination of aperture plate 365. The canting force and inclination urge rotation of binding member 364. It is contemplated that a single friction member may be employed. It is further contemplated that frictional members 362 may have flexible portions, which may be of varying flexibility according to the particular requirements of a needle application.

As facilitated by movement of stylette 316, the canting force causes a lever or moment of end sensing member 371, which is opposed to prevent rotation of binding member 364. The canting force is opposed by engagement of needle communicating surface 372 with stylette 316 in a non-binding or sliding orientation (FIG. 2) of binding member 364.

End sensing member 371 extends distally from aperture plate 365, parallel to stylette 316. End sensing member 371 may be perpendicularly oriented relative to a plane defined by aperture plate 365. This perpendicular orientation facilitates inclination of aperture plate 364 for disposal in a binding or non-binding orientation of binding member 364. It is envisioned that end sensing member 371 may be variously oriented with aperture plate 365 and may flexibly extend therefrom.

Needle communicating surface 372 opposes the canting force of end sensing member 371 directed to stylette 316. The canting force is generated by friction members 362 in conjunction with one of blocking members 340 and/or 342 and facilitates inclination of aperture plate 365. Inclination, however, is prevented in the non-binding or sliding orientation because of the engagement of needle communicating surface 372 with stylette 316. As stylette 316 is retracted proximally and shield 300 is extended distally, stylette 316 continues to slideably engage needle communicating surface 372.

As stylette 316 is released from engagement with needle communicating surface 372, as shown in FIG. 4, a drag force is created between friction members 362 and stylette 316. The drag force in conjunction with blocking member 342, cause aperture plate 365 to move to the binding position, as discussed.

Rotation of aperture plate 365 causes binding surfaces 368 to frictionally engage stylette 316 to prevent movement thereof. Blocking members 340, 342 cause aperture plate 365 to move to the binding position as forces are imposed on shield 300 in either direction along longitudinal axis x. This maintains stylette 316 within shield 300 to avoid hazardous exposure to distal end 314.

Aperture 366 is formed within aperture plate 365 for slidable engagement with stylette 316 during movement between the retracted position and the extended position of shield 300. Aperture 366 includes binding surfaces 368 formed on opposing sides of aperture 366 that engage stylette 316 to prevent movement thereof in the extended position of shield 300. It is contemplated that engagement to prevent movement of stylette 316 may include penetrating, frictional, interference, etc. It is envisioned that aperture 366 may have various geometric configurations, such as radial, polygonal, etc. It is further envisioned that aperture 366 may define an open cavity within aperture plate 365, such as, for example, "U" shaped and open to one or a plurality of edges of aperture plate 365.

Figure 2:
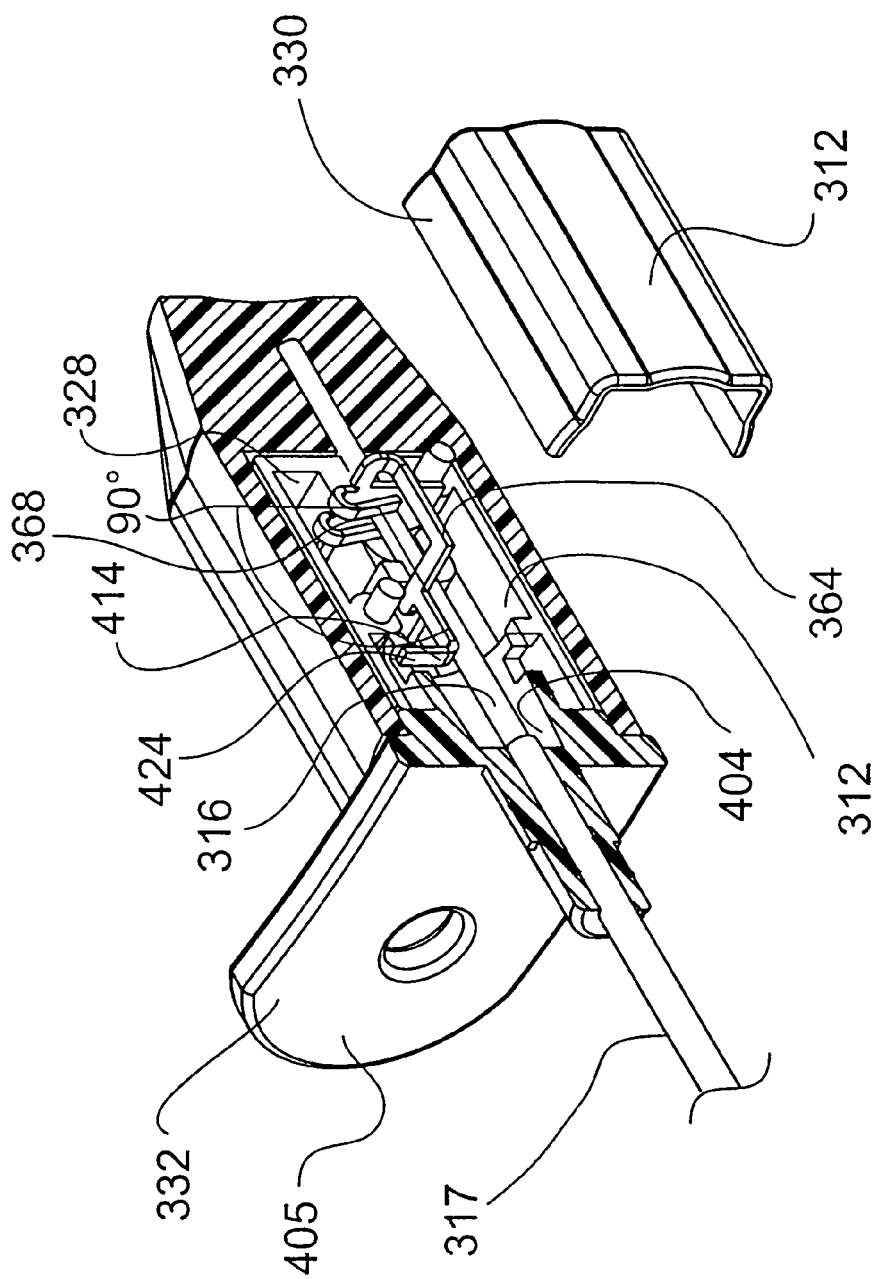
FIG. 2 is a cutaway perspective view of a shield, in a non-binding orientation, of the medical needle shield apparatus shown in FIG. 1 with a housing section separated.
Figure 3:
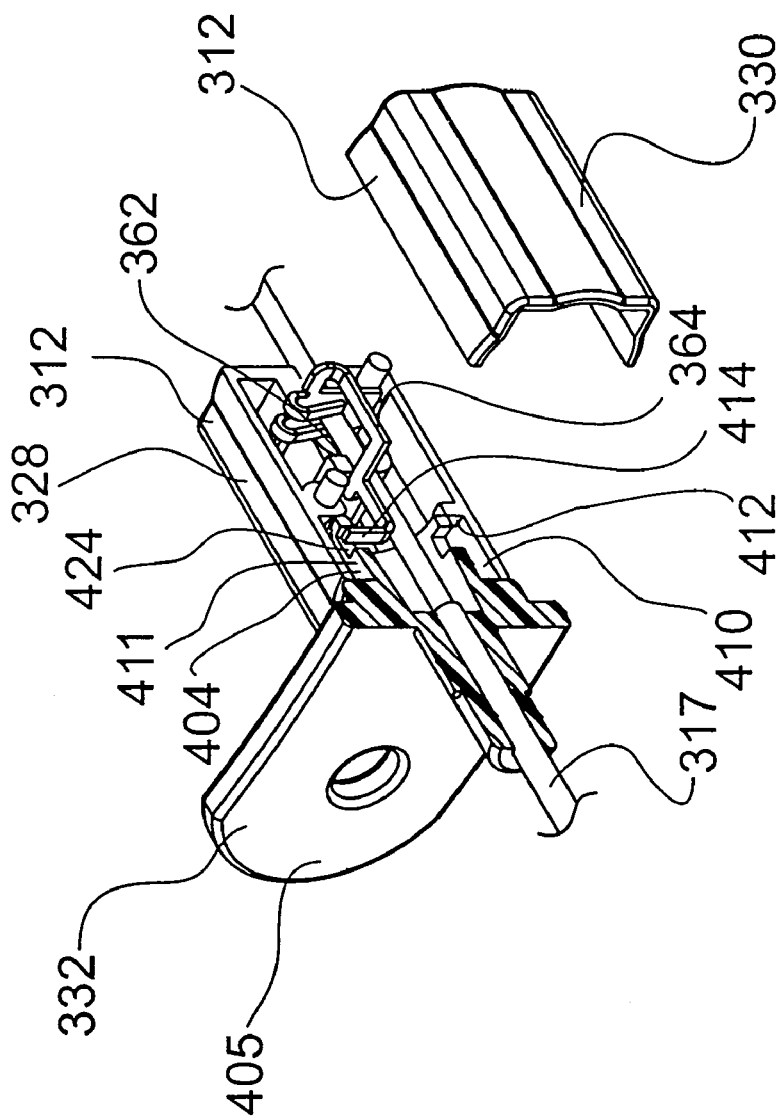
FIG. 3 illustrates the cutaway perspective view of the medical needle shield apparatus shown in FIG. 2.

The inclination of aperture plate 365 relative to longitudinal axis x facilitates sliding and binding, via binding surfaces 368, of stylette 316 within shield 300 to prevent hazardous exposure to distal end 314. For example, as shown in FIG. 2, aperture plate 365 is oriented at an angle of approximately 90° relative to longitudinal axis x such that aperture plate 365 is disposed substantially perpendicular to stylette 316. In this non-binding or sliding orientation, stylette 316 is free to slide within aperture 366. As stylette 316 is retracted and shield 300 is extended, stylette 316 continues to engage needle communicating surface 372 and aperture plate 365 maintains its perpendicular orientation relative to longitudinal axis x.

Referring to FIG. 5, shield 300 is manipulated such that friction members 362 in conjunction with blocking member 342 cause binding member 364 to rotate relative to longitudinal axis x. Aperture plate 365 rotates out of perpendicular alignment with stylette 316 such that aperture plate 365 is oriented at an angle α, which is less than 90° with respect to longitudinal axis x. It is contemplated that angle α may be measured from either side of aperture plate 365.

Aperture plate 365 rotates to angle α and binding member 364 approaches a binding orientation. The binding orientation includes engagement of binding surfaces 368 with stylette 316 due to the binding orientation of aperture plate 365. This engagement creates binding frictional forces on stylette 316, in conjunction with frictional members 362 and blocking members 340, 342 to prevent movement of stylette 316 relative to shield 300 in both distal and proximal directions, and to maintain distal end 314 within shield 300 to prevent hazardous exposure thereto.

Blocking members 340, 342 may be formed with one or both of housing sections 328 and 330, and are disposed not to interfere with stylette 316. Blocking members 340, 342 define surfaces 340A, 342A respectively, that facilitate disposal of aperture plate 365 in a binding orientation.

For example, as shown in FIG. 2, shield 300 is in a retracted position and stylette 316 is fully extended. Binding member 364 and aperture plate 365 are in a non-binding or sliding orientation such that aperture plate 365 is substantially perpendicular to longitudinal axis x. Blocking members 340, 342 may engage aperture plate 365 to maintain aperture plate 365 in the perpendicular orientation. Blocking members 340, 342 may also maintain such orientation during extension of stylette 316 or may not engage stylette 316.

As stylette 316 is retracted and shield 300 is extended, as shown in FIG. 5, friction members 362 create a drag force via engagement with stylette 316 on binding member 364 and in conjunction with blocking member 342 cause aperture plate 365 to rotate in a counter-clockwise direction to the binding position. Blocking member surfaces 340A, 342A engage aperture plate 365 to facilitate rotation thereof from the perpendicular position into the binding position such that binding surfaces 368 engage stylette 316, as discussed. This configuration prevents movement of stylette 316.

Binding of binding member 364 to stylette 316 is facilitated by the friction force generated between binding surfaces 368 and stylette 316. This frictional engagement prevents axial movement of stylette 316 relative to housing 312 when shield 300 is in the extended position. This configuration advantageously prevents hazardous exposure to stylette 316. It is contemplated that binding surfaces 368 may include sharp edges to increase frictional engagement. It is further contemplated that the binding friction force may be created and varied by one or more altering factors, such as, for example, aperture 366 configuration and dimension, stylette 316 configuration and dimension, aperture plate 365 thickness, the dimension from blocking members 340, 342 contact point to the centerline of stylette 316 and the coefficient of friction between aperture 366 and stylette 316 depending on the particular requirements of a needle application. It is envisioned that friction members 362 may be configured so as to vary the drag force with variation of the inclination of the aperture plate 365, this variation in drag force may be accomplished by geometric changes in the shape of the friction members 362, such as wedge shapes or the inclusion of notches to engage stylette 316, this variation in drag force may also be accomplished through the selective application of friction modifying materials or coatings such as oils, jells, greases, or coatings which increase friction.

Needle hub 332 is mounted with needle 317. Needle hub 332 is releasably mounted with shield 300 via releasable engagement with retainer 414. Needle hub 332 is employed with the medical needle shield apparatus of the present disclosure for various utility according to the requirements of a particular medical needle application. Shield 300 and needle hub 332 slidably support needle 317 and stylette 316 for use thereof. Handle 318 facilitates manipulation thereof.

Needle hub 332 has a hub slot 424 for receipt and engagement with binding member 364. Needle hub 332 has a finger tab 405 for urging needle hub 332 in a direction, along longitudinal axis x, away from shield 300. This configuration facilitates removal and use of needle hub 332 and needle 317 from shield 300 during a medical needle application. It is contemplated that finger tab 405 may be alternatively configured and dimensioned according to the needle application.

A flange 404 of needle hub 332 is concentrically supported by a control surface 410 disposed about an inner surface of housing 312. Control surface 410 engages an outer surface 411 of flange 404 for releasable support thereof. Outer surface 411 may engage control surface 410 in a frictional, interference, etc. fit to maintain releasable positioning with housing 312. It is contemplated that control surface 410 may engage other portions of needle hub 332.

Housing 312 includes hub stop surfaces 412 that facilitate positioning of needle hub 332 with housing 312. Hub stop surfaces 412 prevent proximal movement of needle hub 332 during mounting with and relative to housing 312. Hub stop surfaces 412 advantageously facilitate control of the degree of insertion with housing 312 according to the requirements of a particular medical needle application. One or a plurality of hub stop surfaces 412 may be employed. It is contemplated that hub stop surfaces 412 may include springs, clips, etc. to facilitate attachment with needle hub 332.

Retainer 414 extends transversely from a distal end of needle communicating surface 372. Hub retainer 414 extends a sufficient length for corresponding receipt within hub slot 424 of needle hub 332. In association with a non-binding or sliding orientation of binding member 364, retainer 414 engages needle hub 332, in hub slot 424, for releasably mounting with housing 312 of shield 300.

As stylette 316 is retracted in a proximal direction and shield 300 is extended in a distal direction, retainer 414 rotates in a counter clockwise direction (FIG. 4) relative to longitudinal axis x due to the canting forces generated by friction members 362. Retainer 414 disengages from hub slot 424 to release needle hub 332 from housing 312. A clinician may manipulate finger tab 405 to manipulate needle hub 332 distally and apart from shield 300. It is contemplated that retainer 414 may be variously oriented from needle communicating surface 372. It is further contemplated that hub slot 424 may be variously dimensioned to extend about the circumference of needle hub 332. Hub slot 424 may include tabs, etc. for retention with retainer 414.

Figure 9:
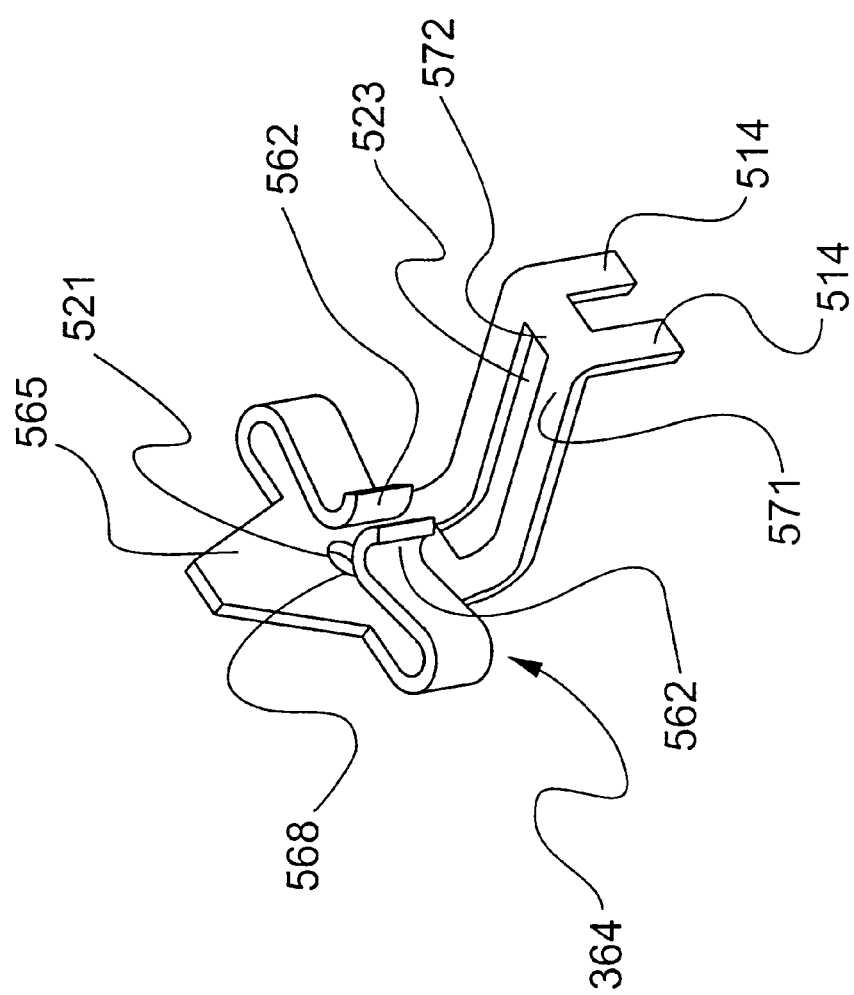
FIG. 9 is an enlarged perspective view of an alternate embodiment of the binding member shown in FIG. 6.

Referring to FIG. 9, an alternate embodiment of binding member 364, similar to that described, is shown. An aperture plate 565 has a polygonal geometric configuration and an end sensing member 571 that extends in a uniform axial orientation, parallel to stylette 316. Needle communicating surface 572 extends transversely to bridge a cavity 523 between arms of end sensing member 571. Binding member 364 includes retainers 514 that extend for engagement with hub slot 424, similar to that described. Friction members 562 extend laterally from aperture plate 365. Friction members 562 include a curled engagement surface for engagement with stylette 316.

Figure 10:
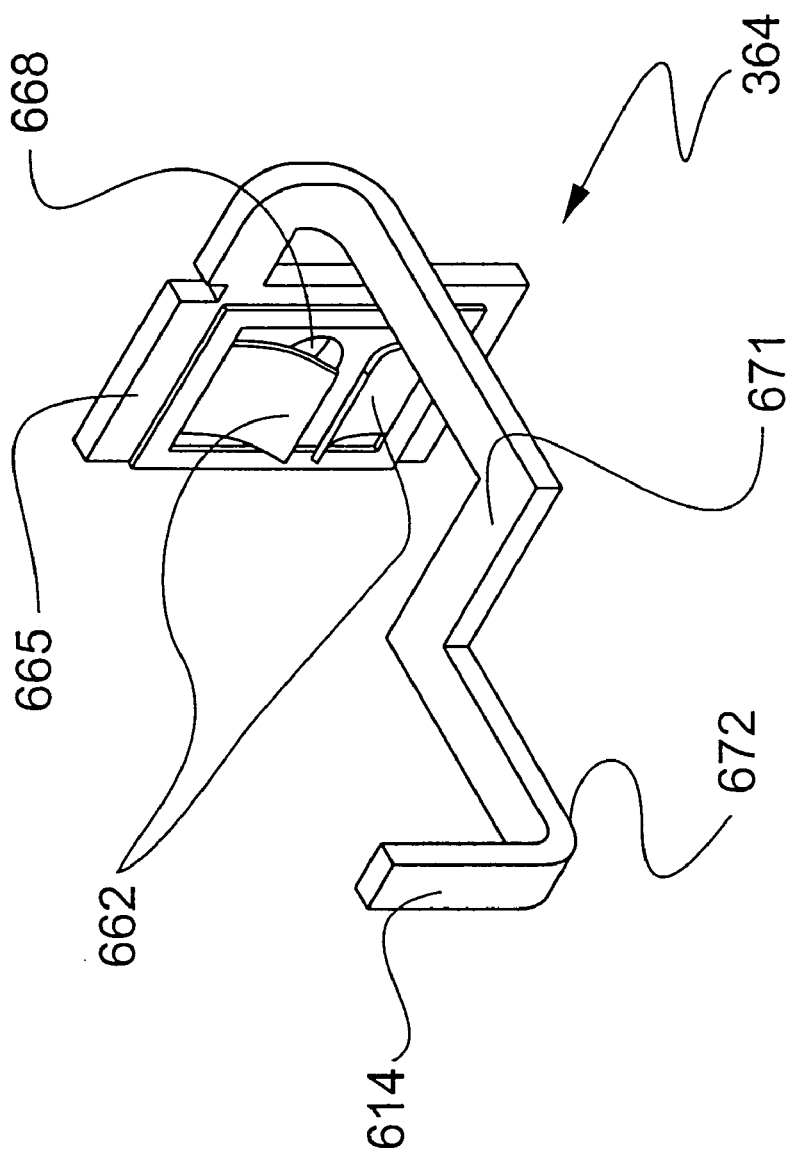
FIG. 10 is an enlarged perspective view of another alternate embodiment of the binding member shown in FIG. 6.

Referring to FIG. 10, another alternate embodiment of binding member 364, similar to those described, is shown. An end sensing member 671 extends axially from an aperture plate 665 and a retainer 614 extends transversely therefrom. Friction members 662 are disposed adjacent to binding surfaces 668. Friction members 662 deflect in an arcuate configuration from aperture plate 665 to slidably engage stylette 316 and create a drag force, as described herein. Binding member 364 has a needle communicating surface 672 that is engageable with stylette 316 to prevent rotation of binding member 364.

Figure 11:
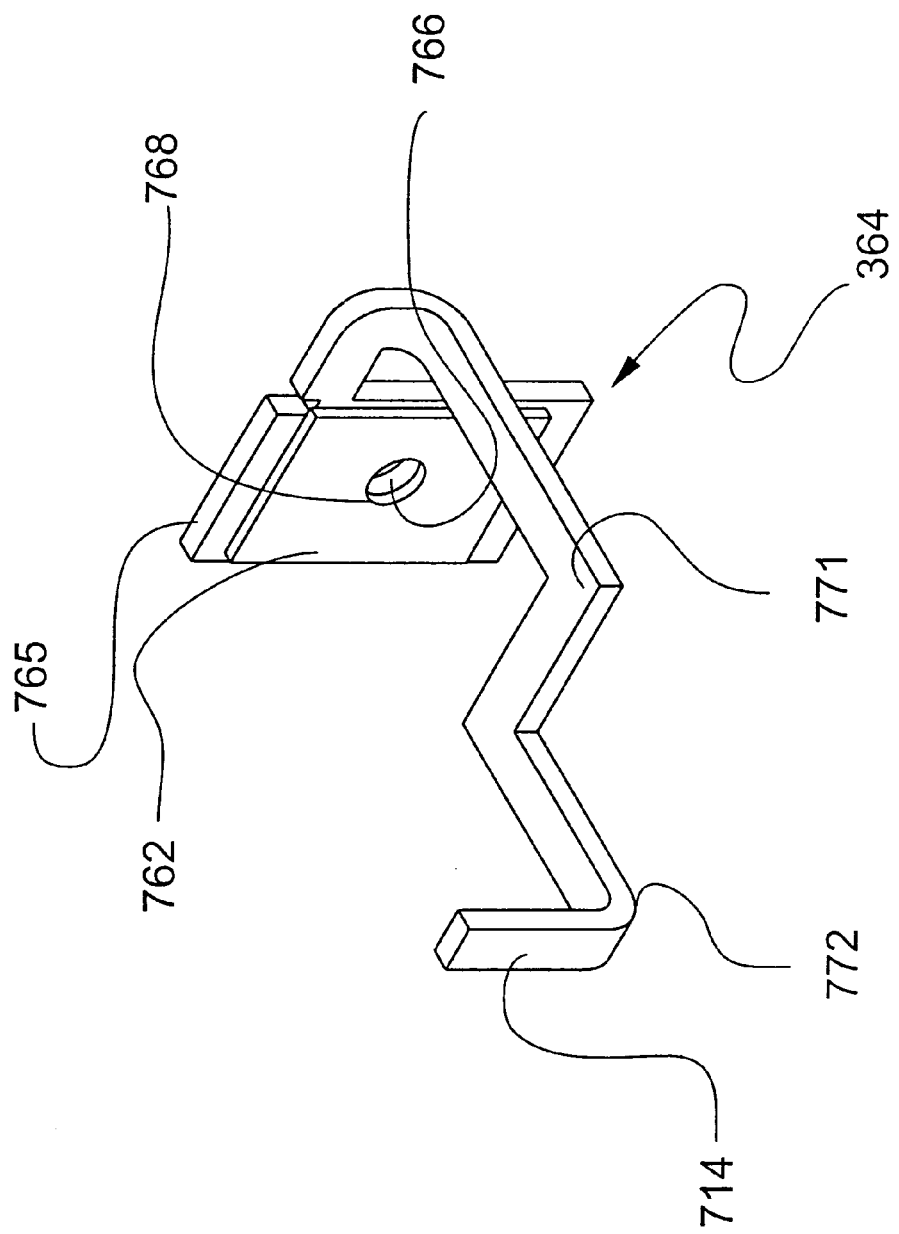
FIG. 11 is an enlarged perspective view of another alternate embodiment of the binding member shown in FIG. 6.

Referring to FIG. 11, another embodiment of binding member 364, similar to those described, is shown. An end sensing member 771 extends axially from an aperture plate 765 and a retainer 714 extends transversely therefrom. Friction member 762 has a rectangular configuration that is mounted with aperture plate 765. Friction member 762 defines an opening that is aligned with aperture 766. The opening of friction member 762 and binding surfaces 766 of aperture 766 slidably engage stylette 316 to create a drag force therewith, similar to that described. Binding member 364 has a needle communicating surface 772 that is engageable with stylette 316 to prevent rotation of binding member 364.

Figure 33:
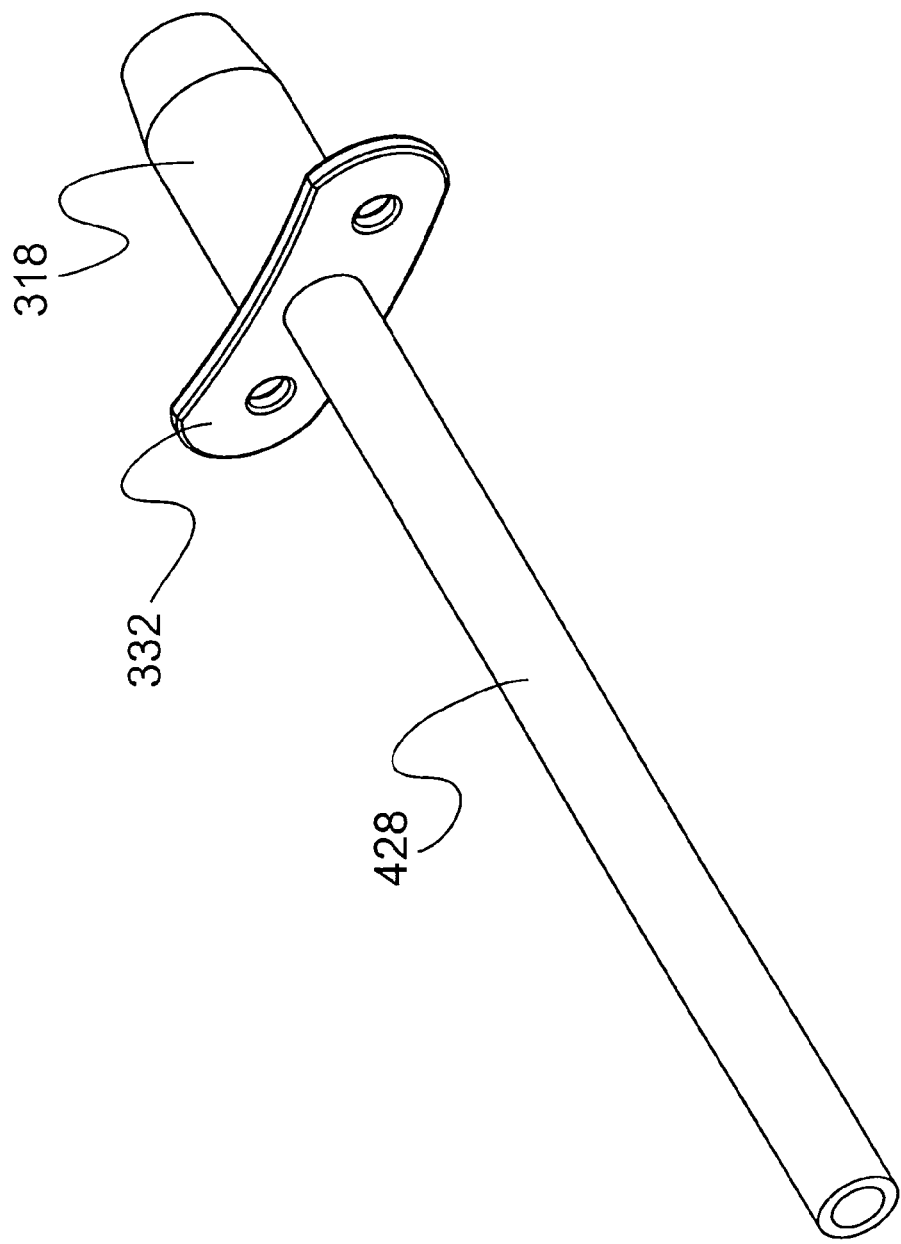
FIG. 33 is a perspective view of the medical needle shield apparatus shown in FIG. 16 with a sheath.

In operation, the medical needle shield apparatus, similar to that described in accordance with the principles of the present disclosure is provided for employment with needle hub 332. The components of the medical needle shield apparatus are fabricated, properly sterilized and otherwise prepared for storage, shipment and use. Referring to FIG. 33, the medical needle shield apparatus is manipulated such that handle 318 is held and a removable sheath 428 is removed therefrom. Sheath 428 is removably mounted to needle hub 332 to enclose the components of the medical needle shield apparatus via friction, snap fit, interference fit, etc.

Referring to FIGS. 1-8, the clinician (not shown) manipulates handle 318 such that shield 300 is in the retracted position (FIG. 2) and binding member 364 is in a non-binding or sliding position. Stylette 316 is extended relative to shield 300 such that needle hub 332 is disposed about needle 317 and needle hub 332 is releasably mounted with housing 312. A procedure employing the medical needle shield apparatus with stylette 316 and needle 317 is performed by the clinician to completion.

Stylette 316 is retracted proximally such that shield 300 is extended toward the extended position. Binding member 364 is in the non-binding or sliding position such that stylette 316 engages needle communicating surface 372 and binding surfaces 368 to facilitate sliding through aperture 366, as discussed.

Referring to FIG. 5, as stylette 316 clears needle communicating surface 372, retainer 414 is free to rotate due to the canting forces created via the engagement of stylette 316 with frictional members 362. Aperture plate 365 rotates counter-clockwise, relative to longitudinal axis x, from the perpendicular orientation to an inclination for a binding orientation as facilitated by blocking members 340, 342. Aperture plate 365 rotates to angle α relative to longitudinal axis x.

Retainer 414 disengages from hub slot 424 such that needle hub 332 is released from housing 312. Needle hub 332 can be manipulated distally via finger tab 405. In the binding position, binding surfaces 368 engage stylette 316 to bind and prevent axial movement of stylette 316 within housing 312. Shield 300 is disposed in the extended position to prevent hazardous exposure to distal end 314.

Figure 12:
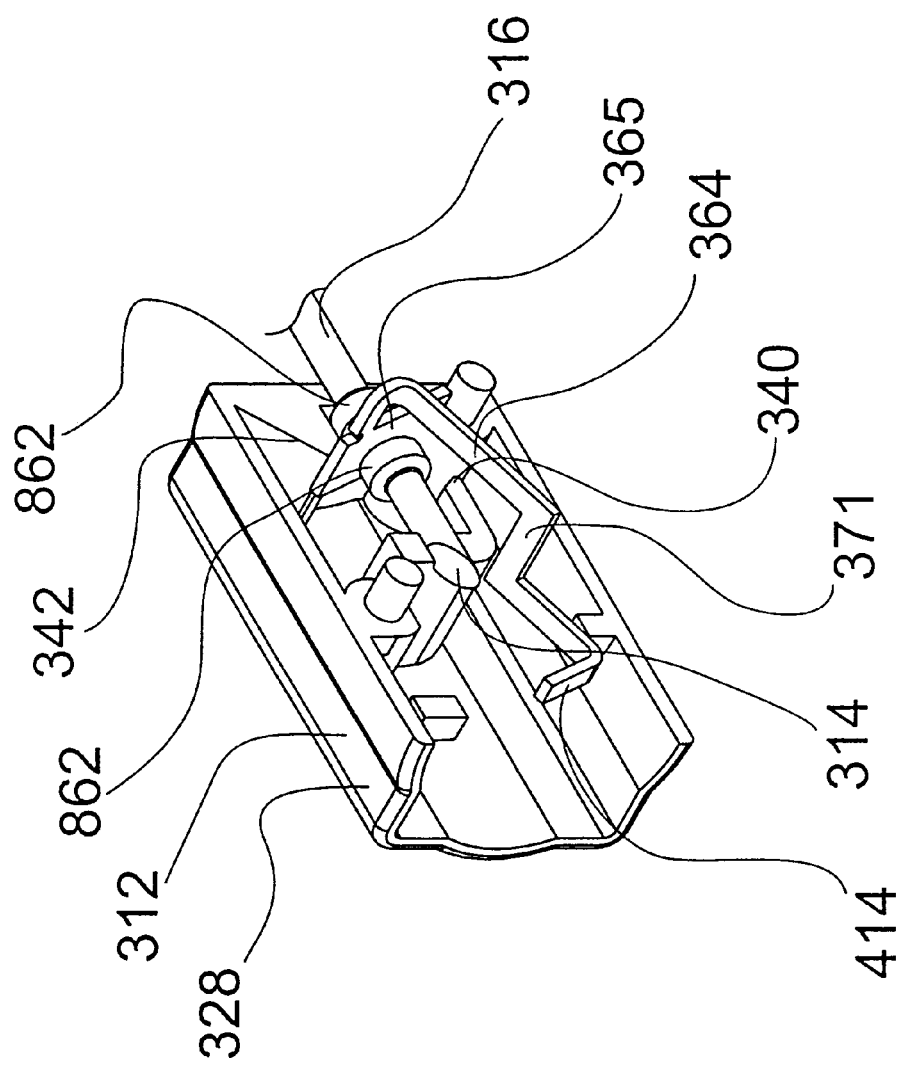
FIG. 12 is a cutaway perspective view of the shield shown in FIG. 5 illustrating an alternate embodiment of the friction members.

In an alternate embodiment, as shown in FIG. 12, binding member 364 includes separate frictional members 862 that are disposed on a proximal side and a distal side of aperture plate 365, respectively. Friction members 862 are friction fit rings, which allow sliding of stylette 316 therewith and provide a frictional drag force, similar to that discussed, via engagement with stylette 316. The drag force is created as stylette 316 slides and friction members 862 engage aperture plate 365. Friction members 862 engage aperture plate 365, and in cooperation with blocking member 340, cause aperture plate 365 to rotate counter-clockwise. Binding surfaces 368 engage stylette 316 to prevent axial movement of stylette 316, as discussed. It is contemplated that friction members 862 may be fabricated from materials such as, polymerics, metals, etc.

Figure 13:
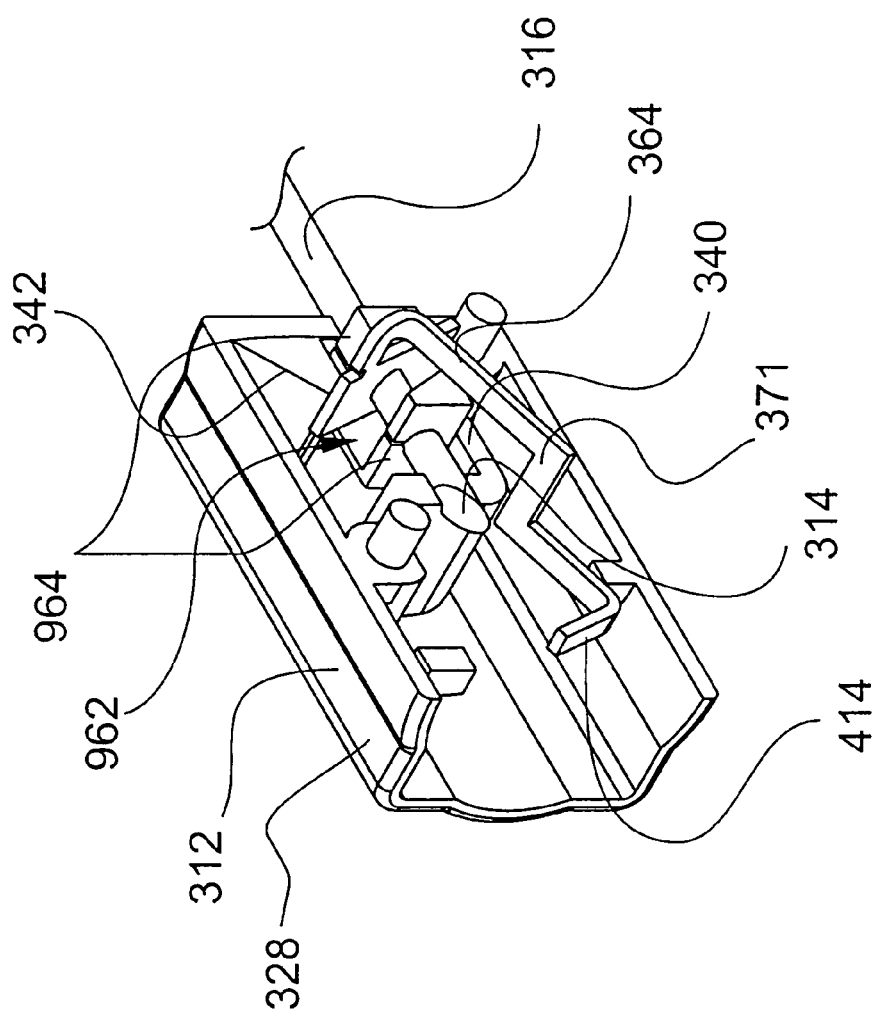
FIG. 13 is a cutaway perspective view of the shield shown in FIG. 12 illustrating another embodiment of the friction members.

Alternatively, friction member 962 may form a monolithic member that links or joins two members 964, as shown in FIG. 13. Members 964 engage stylette 316 and aperture plate 365 to prevent axial movement of stylette 316, similar to that discussed with regard to FIG. 12. It is envisioned that aperture 366 may create a drag force via engagement with stylette 316 to cause rotation of binding member 364, similar to that described. It is further envisioned that materials such as, for example, jells, greases, etc. may be employed to create a frictional drag force with stylette 316 to cause rotation of binding member 364.

Figure 14:
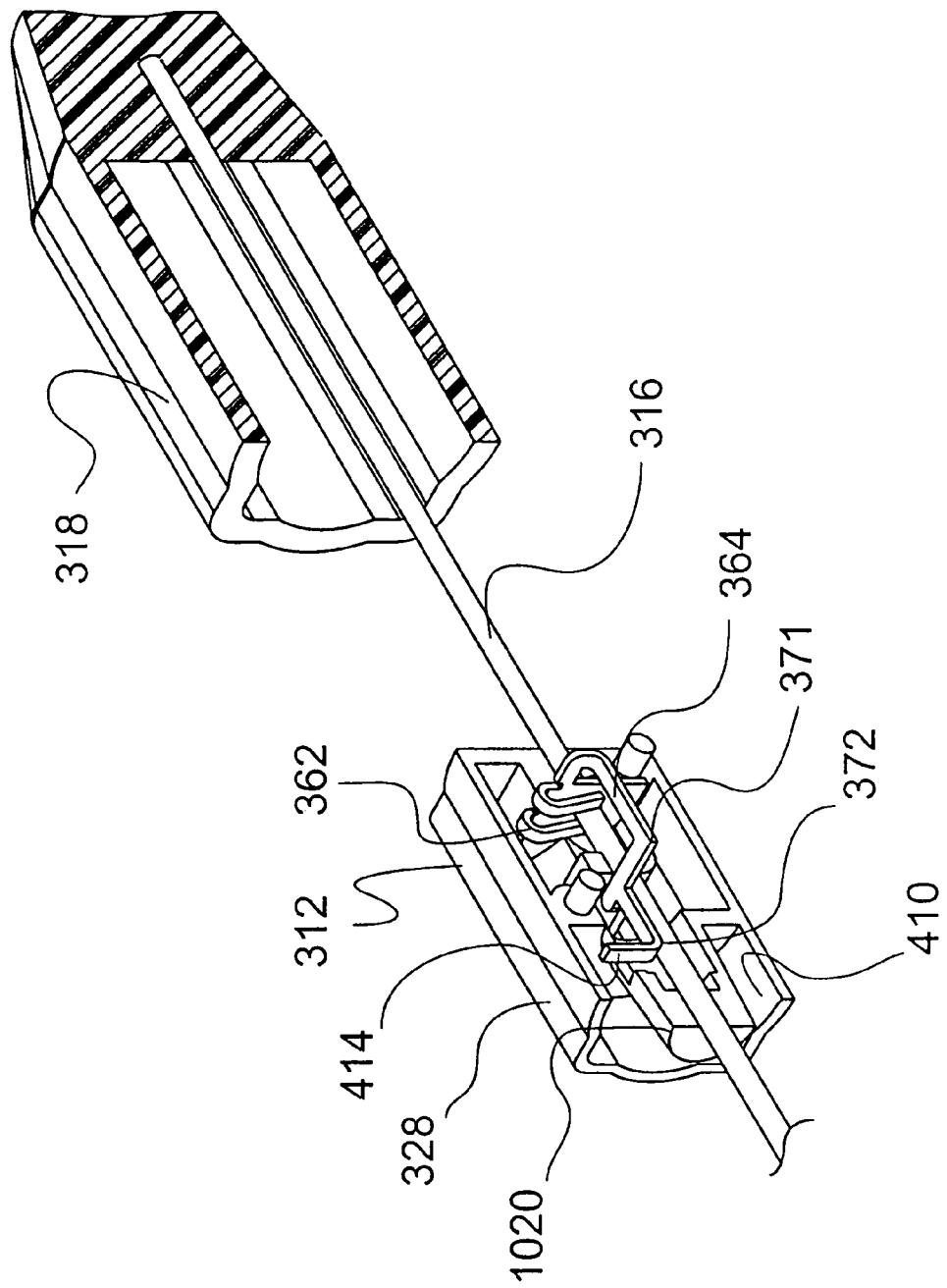
FIG. 14 is a cutaway perspective view of an alternate embodiment of the medical needle shield apparatus shown in FIG. 1, with an additional hub support.
Figure 15:
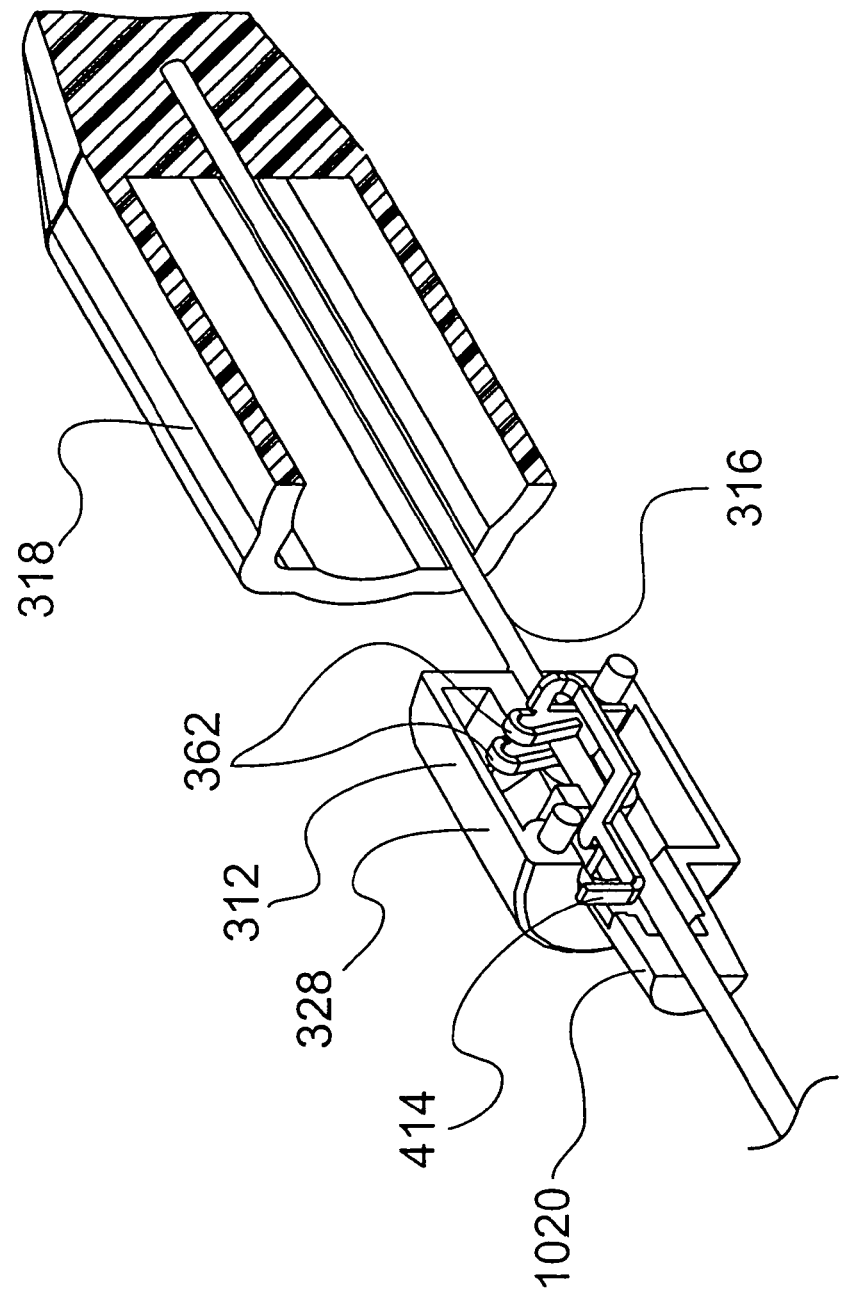
FIG. 15 is a cutaway perspective view of the medical needle shield apparatus shown in FIG. 1 illustrating an alternate embodiment of the shield.
Figure 16:
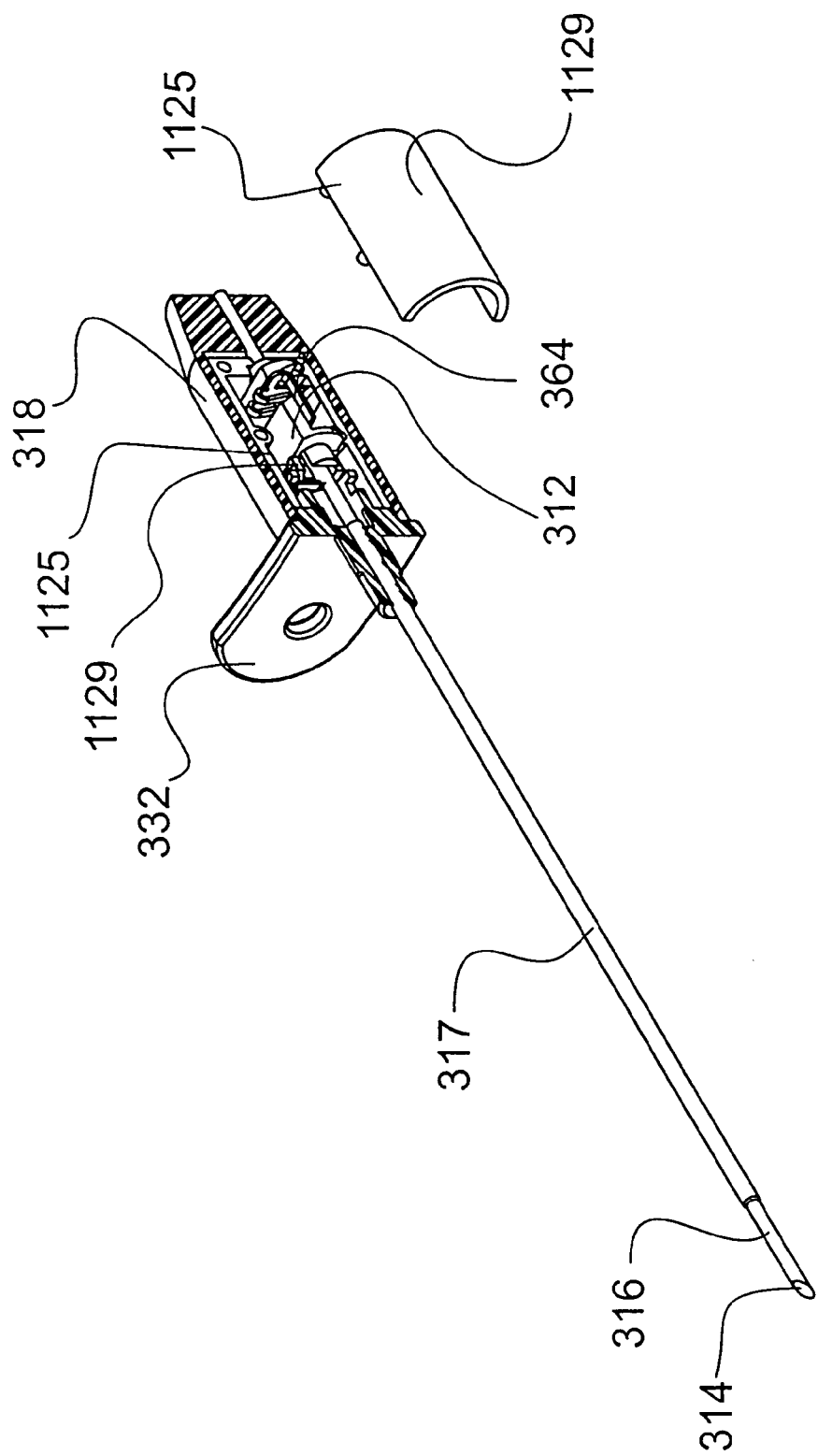
FIG. 16 is a cutaway perspective view of the medical needle shield apparatus shown in FIG. 1 with an outer rotatable housing.
Figure 17:
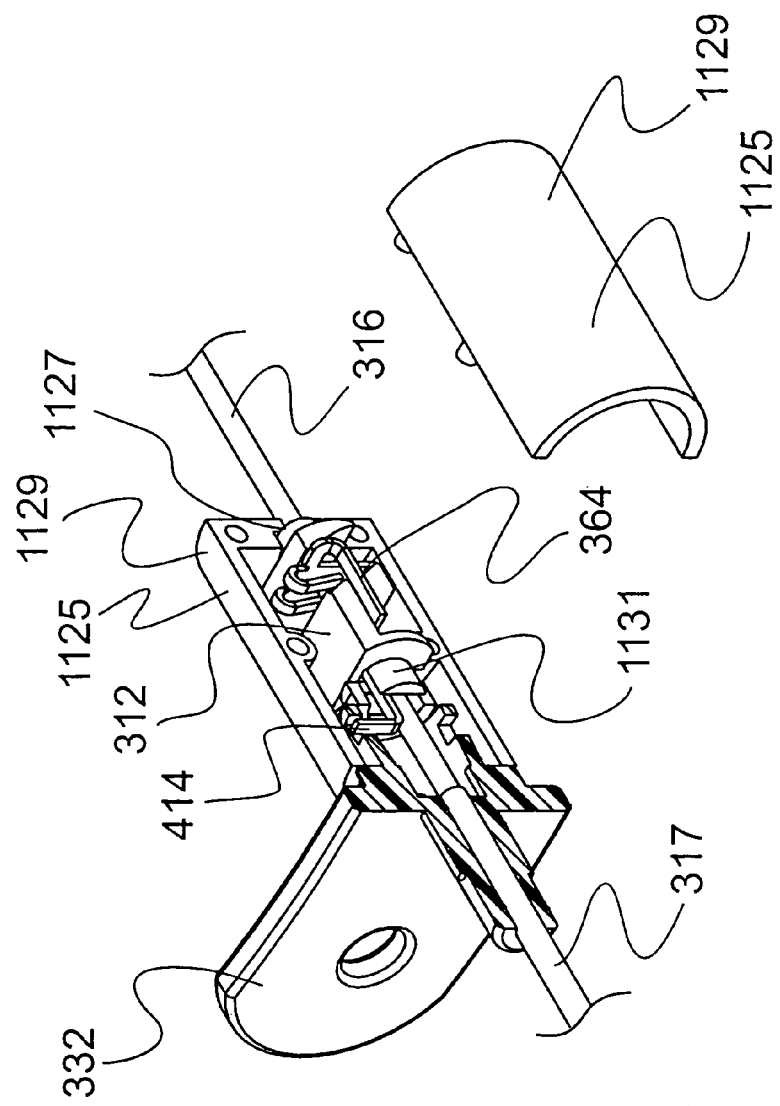
FIG. 17 is an enlarged cutaway perspective view of the medical needle shield apparatus shown in FIG. 16, with a housing section removed.
Figure 18:
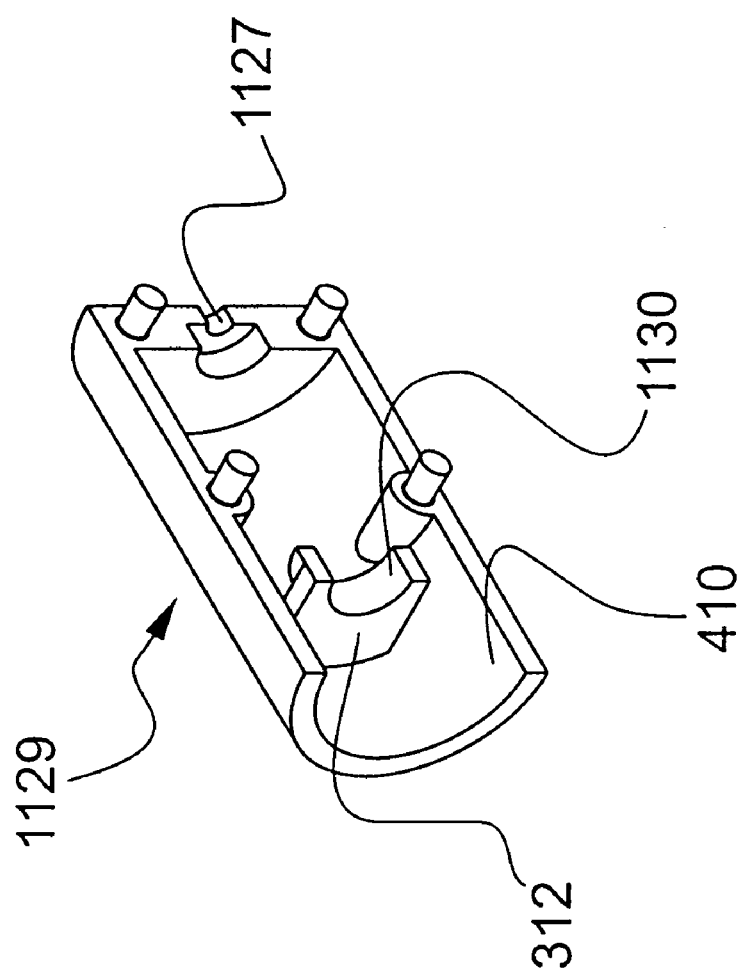
FIG. 18 is a perspective view of a housing section shown in FIG. 17.
Figure 19:
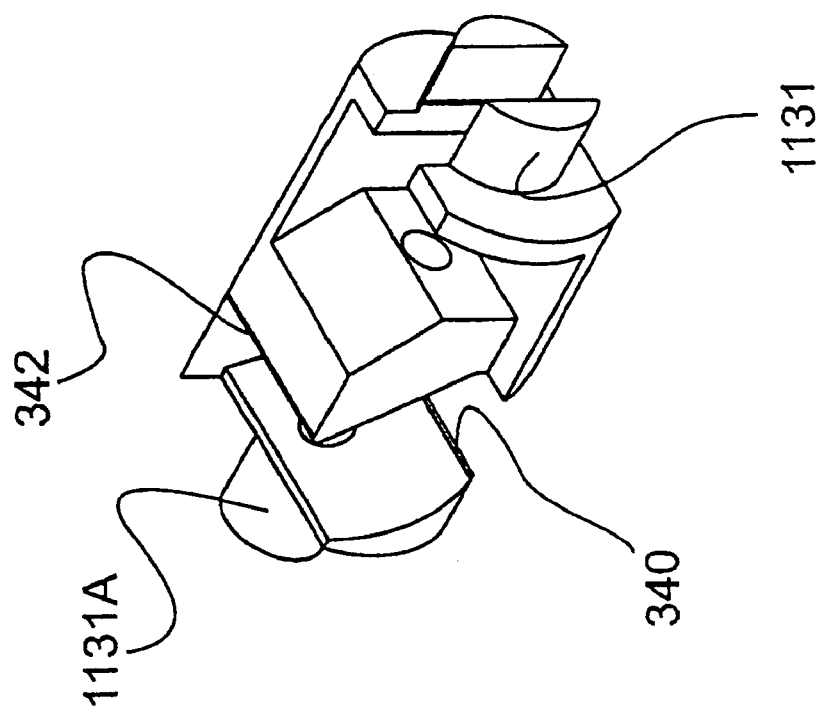
FIG. 19 is an enlarged perspective view of an axle of the medical needle shield apparatus shown in FIG. 16.

In an alternate embodiment, as shown in FIG. 14, housing 312 includes a hub support 1020. Hub support 1020 is received by needle hub 332 to advantageously facilitate removable mounting of needle hub 332 with shield 300. Alternatively, as shown in FIG. 15, control surface 410 of housing 312 may be cut back or eliminated. This configuration allows hub support 1020 to solely facilitate mounting of needle hub 332 via a concentric relationship therewith.

Referring to FIGS. 16-19, another alternate embodiment of the medical needle safety apparatus is shown. An external grip element 1125, having grip element sections 1129, is disposed for rotation and enclosure of shield 300. External grip element 1125 is mounted with handle 318 and freely rotates relative to shield 300 and stylette 316 in the extended position of shield 300. Relative rotation of external gripping element 1125 is facilitated by support at bearing opening 1127 and bearing opening 1130 formed in external gripping element 1125. Axles 1131, 1131A are rotationally supported in bearing openings 1130, 1127, respectively. In a binding position, the bearing configuration supports rotation of external gripping element 1125 relative to shield 300 and stylette 316. Housing 312 includes blocking member 340, 342, similar to those discussed. Stylette 316 passes through blocking members 340, 342 for slidable movement relative thereto. The halves of axle 1131 are spaced apart such that stylette 316 and retainer 414 may be disposed therein.

Figure 26:
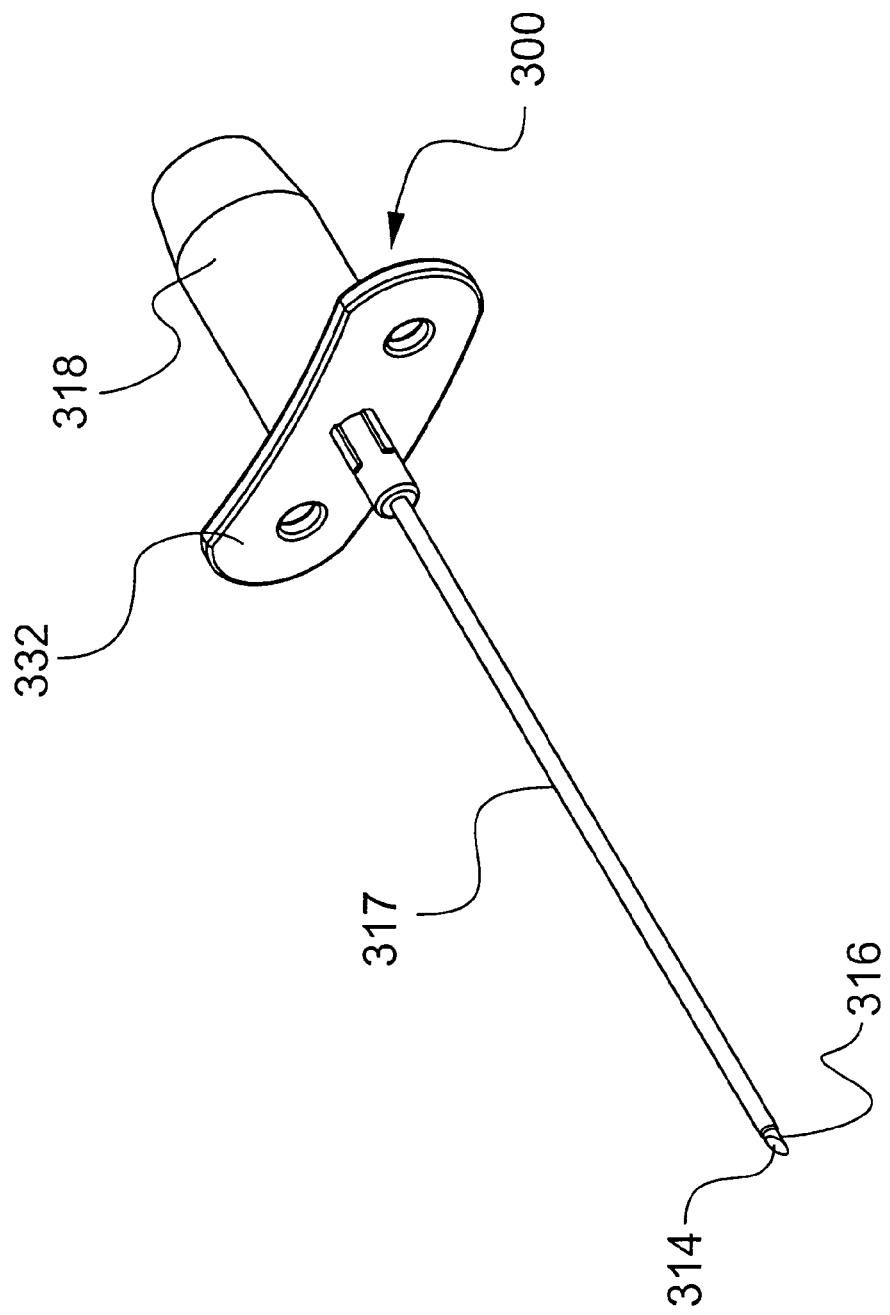
FIG. 26 is a perspective view of the medical needle shield apparatus shown in FIG. 16, prior to actuation.
Figure 27:
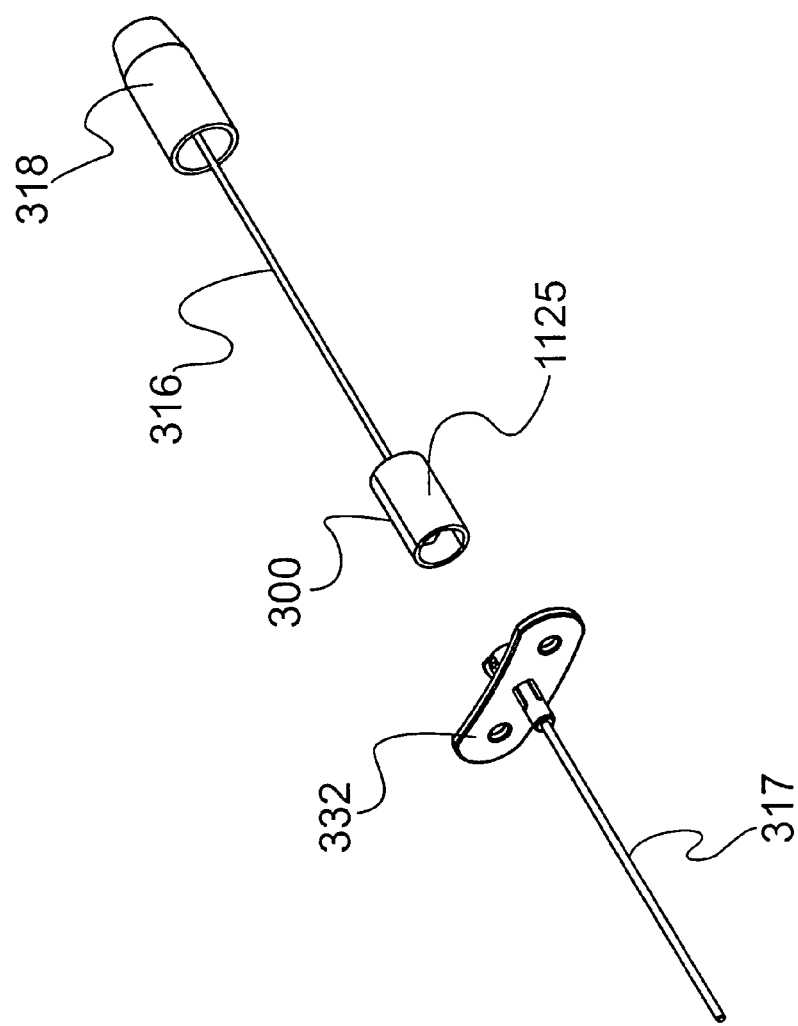
FIG. 27 is a perspective view of the medical needle shield apparatus shown in FIG. 16, in the actuated position.
Figure 28:
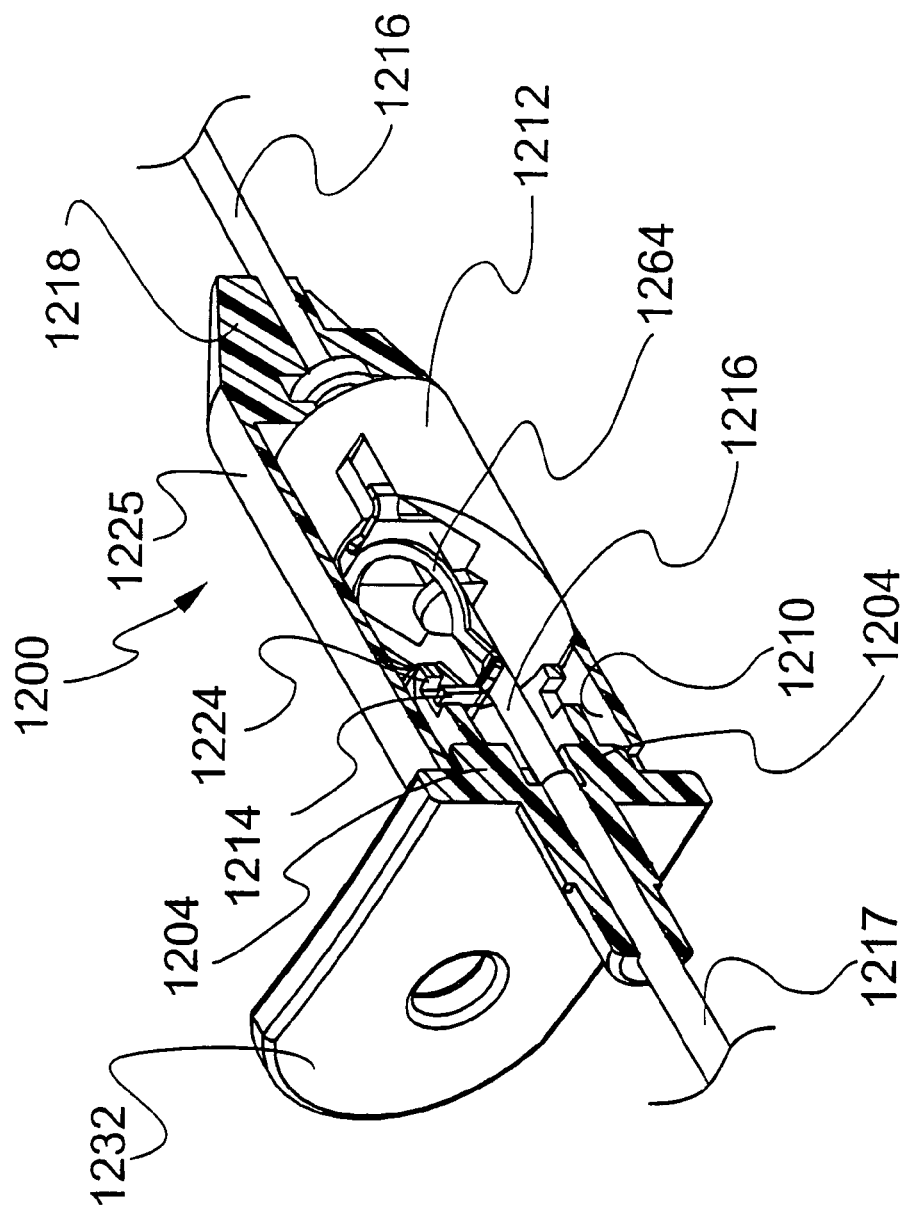
FIG. 28 is a cutaway perspective view of another embodiment of the medical needle shield apparatus shown in FIG. 16, with a housing section removed.

Referring to FIG. 26, shield 300 is in the retracted position and binding member 364 is in a non-binding or sliding position. Stylette 316 is extended relative to shield 300 such that distal end 314 protrudes out of needle 317. Needle hub 332 is releasably mounted with housing 312. Referring to FIG. 27, stylette 316 is retracted proximally such that shield 300 is extended to the extended position and binding member 364 is disposed in a binding position. Needle hub 332 is released from shield 300 and external gripping element 1125 encloses shield 300 in the extended position.

This configuration prevents rotation of shield 300 about longitudinal axis x of stylette 316 such that binding member 364 is not undesirably rotated to disturb the protective binding engagement with stylette 316. Thus, the possibility of intentionally abusing and defeating the protective configuration of shield 300, in the extended position, by manually and abusively twisting shield 300 is reduced. It is envisioned that the length of opening 1127 may be increased such that the radial clearance of opening 1127 with stylette 316 limits tilting of shield 300 within external grip element 1125. This configuration prevents radial contact of shield 300 with external grip element 1125.

Figure 20:
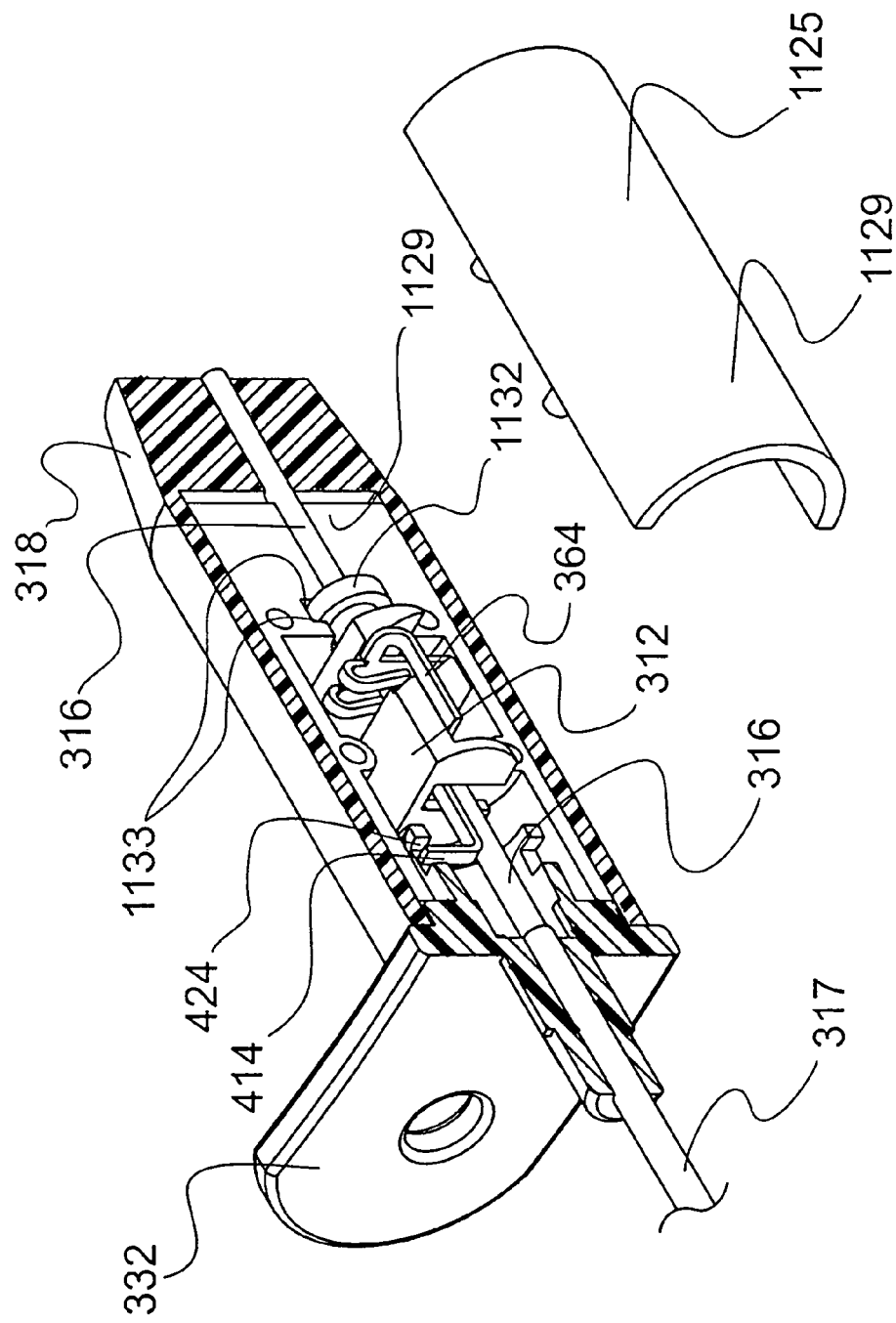
FIG. 20 is a cutaway perspective view of an alternate embodiment of the medical needle shield apparatus shown in FIG. 16 with parts separated.

Referring to FIG. 20, in an alternate embodiment, housing 312 includes a thrust collar 1132 mounted to housing 312. A corresponding thrust base 1133 of external grip element 1125 is configured to support thrust collar 1132 and controls relative axial movement between housing 312 and external grip element 1125. Thrust collar 1132 freely rotates within thrust base 1133 to facilitate rotation of housing 312 and limit tilting of shield 300 within external grip element 1125.

Figure 21:
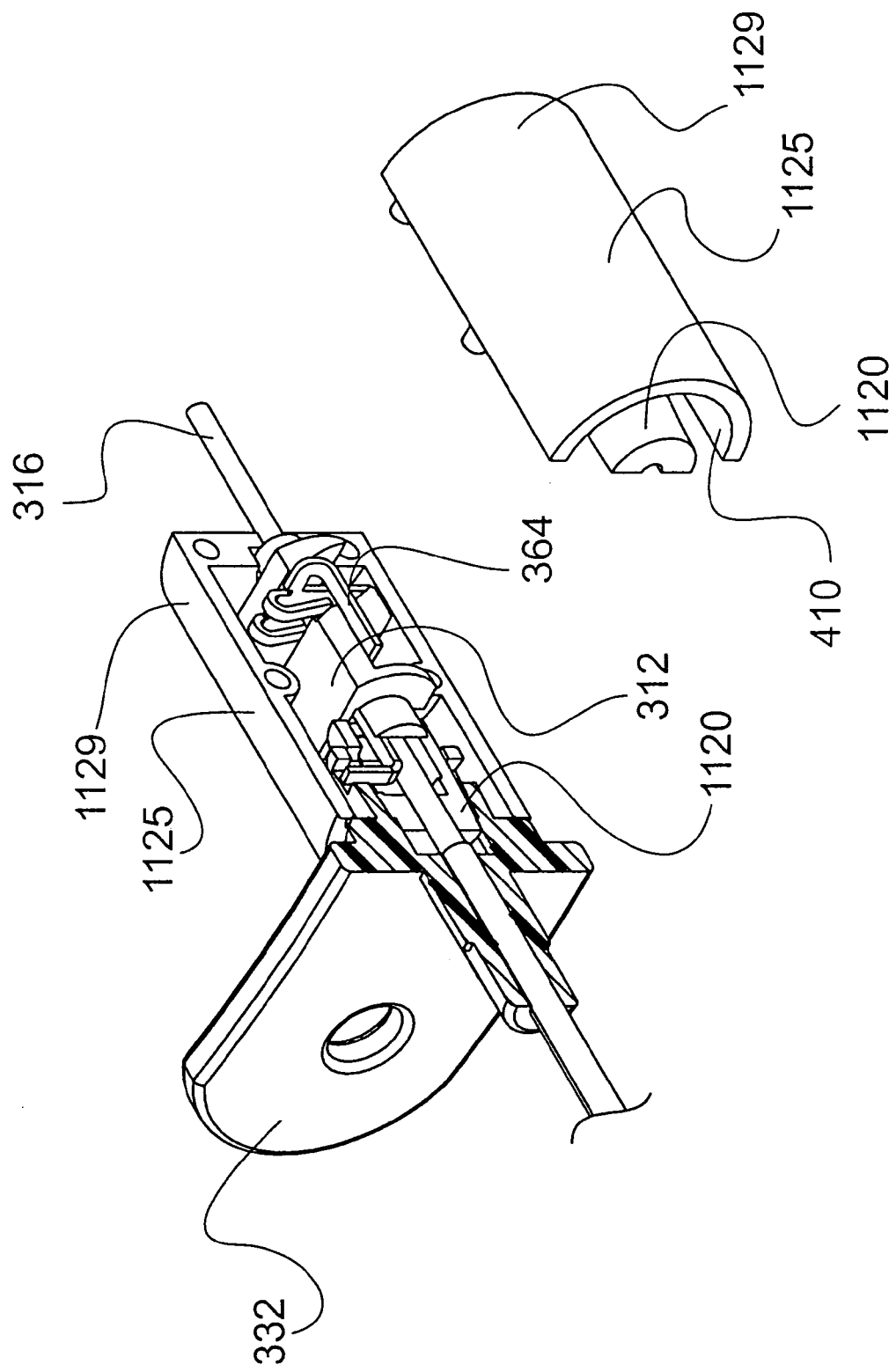
FIG. 21 is a cutaway perspective view of another alternate embodiment of the medical needle shield apparatus shown in FIG. 16 with parts separated.
Figure 22:
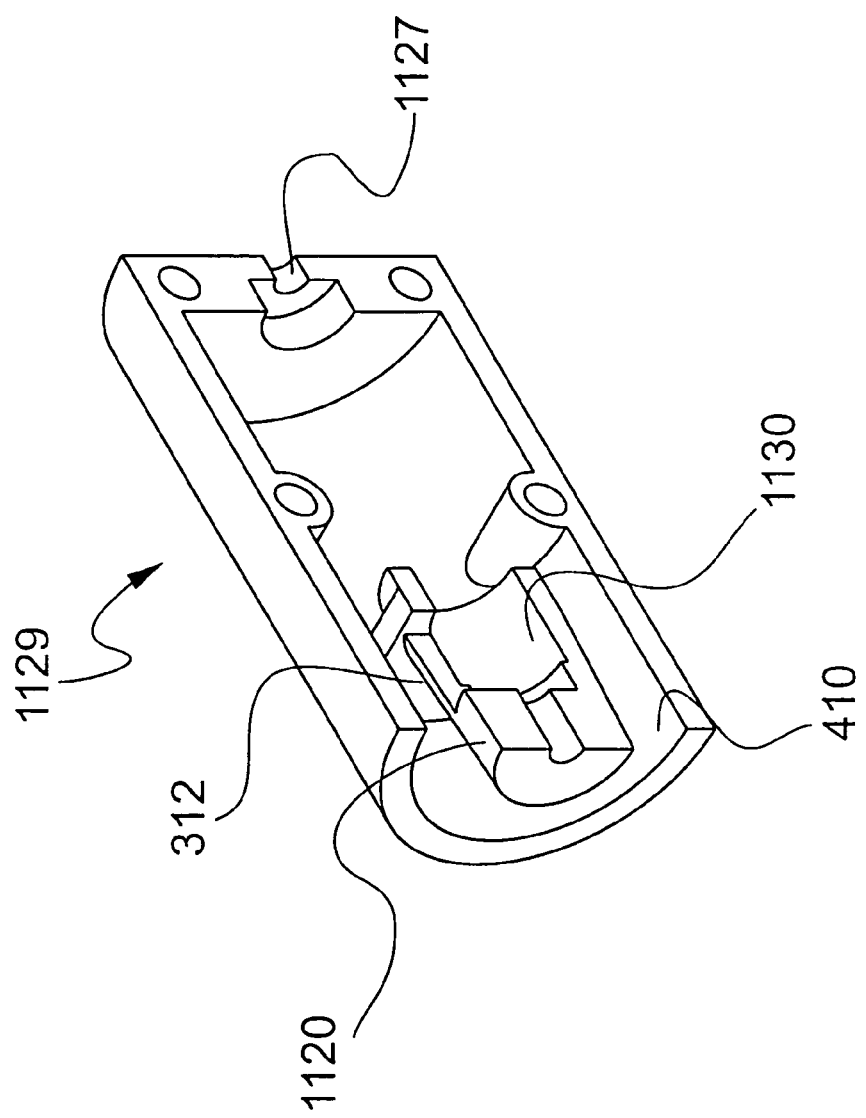
FIG. 22 is an enlarged perspective view of a housing section shown in FIG. 21.
Figure 23:
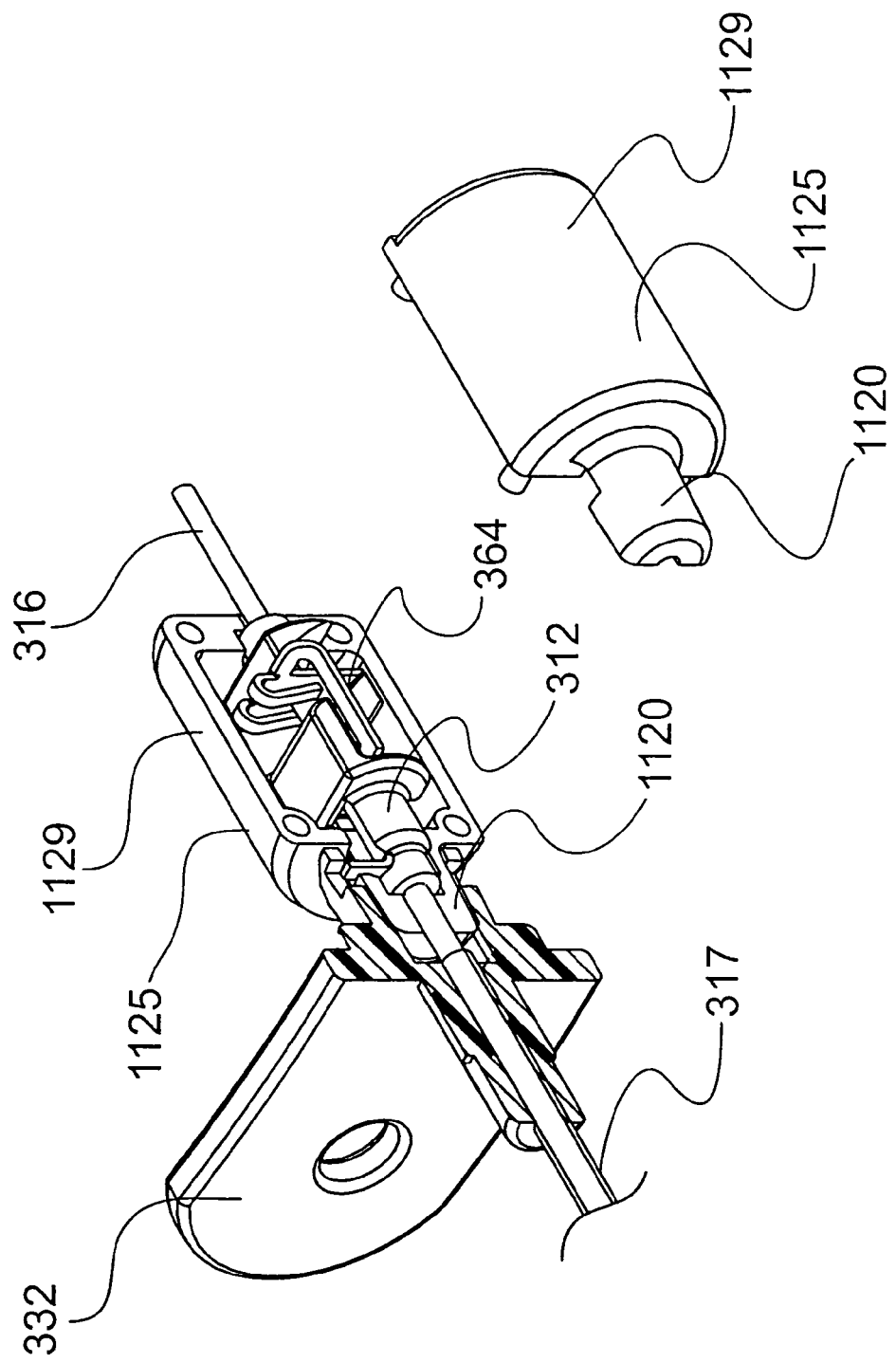
FIG. 23 is an enlarged perspective view of an alternate embodiment of the medical needle apparatus shown in FIG. 16, with a housing section removed.
Figure 24:
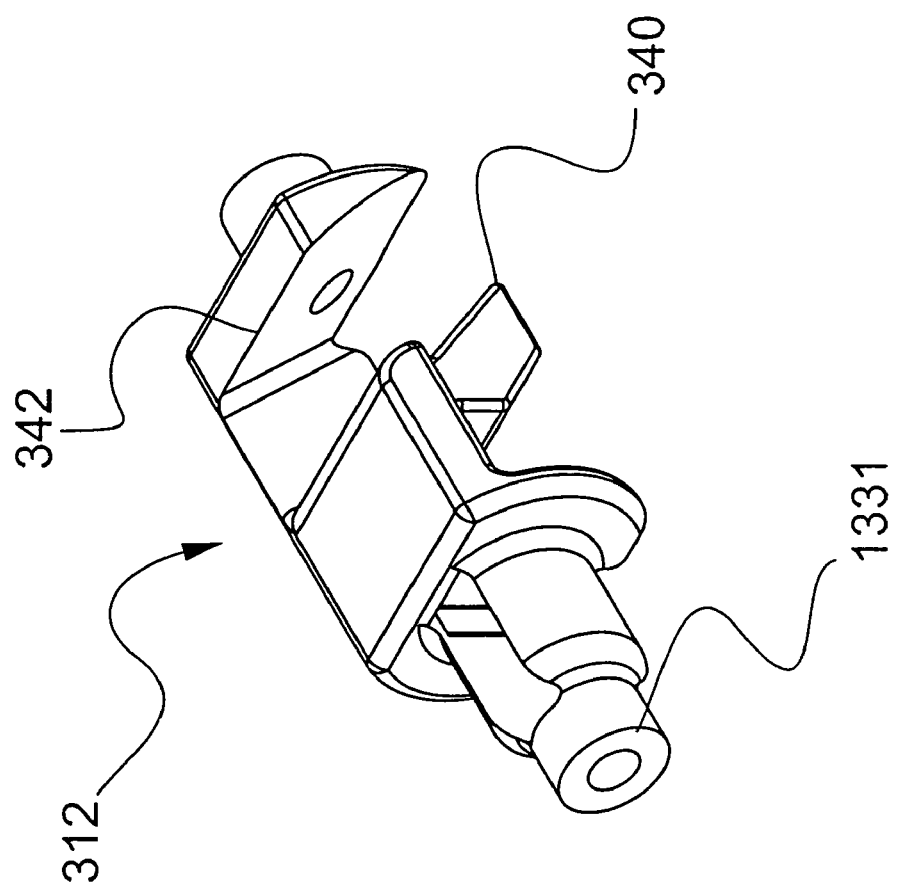
FIG. 24 is an enlarged perspective view of an axle shown in FIG. 23.
Figure 25:
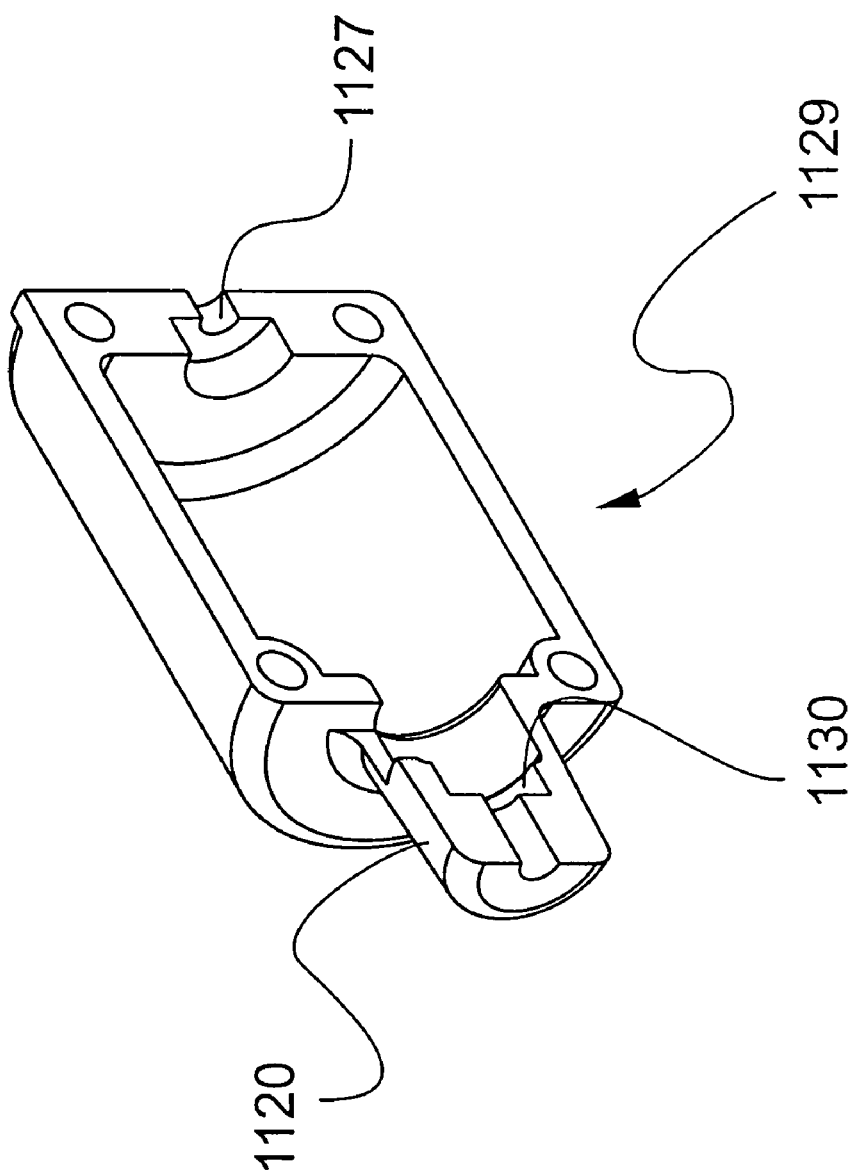
FIG. 25 is an enlarged perspective view of a housing section shown in FIG. 23.

Alternatively, as shown in FIGS. 21 and 22, external grip element 1125 includes a hub support 1120, similar to that discussed above. In another alternative, as shown in FIGS. 23-25, control surface 410 of housing 312 may be cut back or eliminated, similar to that discussed above. Hub support 1120 is connected to external gripping element 1125 to facilitate the mounting relationship of needle hub 332 with housing 312.

In another alternate embodiment, as shown in FIGS. 28-32, the medical needle shield apparatus includes a shield 1200, similar to those described, that is extensible from a retracted position to an extended position to enclose a distal end 1215 of a stylette 1216 of a needle assembly. Stylette 1216 is slideably and concentrically disposed with a needle 1217 of the needle assembly for employment therewith during a medical needle application. A stylette handle 1218 is connected to stylette 1216.

A binding member 1264 is disposed within shield 1200 and defines binding surfaces 1268. Binding surfaces 1268 form an aperture 1266. Binding member 1264 includes friction members 1262 extending therefrom. Binding member 1264 has a needle communicating surface 1272 that is engageable with stylette 1216 to prevent rotation of binding member 1264. Friction members 1262 are configured for slidable engagement with stylette 1216 between the retracted position and the extended position such that friction members 1262 engage stylette 1216 to create a drag force, similar to those described, with stylette 1216. Shield 1200 includes a housing 1212 that encloses binding member 1264.

As stylette 1216 is released from engagement with a needle communicating surface 1272, binding member 1264 and a retainer 1214 move to a binding position. Rotation of binding member 1264 causes binding surfaces 1268 to frictionally engage stylette 1216 to prevent movement thereof. Housing 1212 includes blocking members 1240 and/or 1242 that cause binding member 1264 to move to the binding position as forces imposed on shield 1200 cause relative movement thereof in either direction along longitudinal axis x. This maintains stylette 1216 within shield 1200 to avoid hazardous exposure to distal end 1214.

Binding member 1264 includes an aperture plate 1265, frictional members 1262, end sensing member 1271, needle communicating surface 1272 and retainer 1214. End sensing member 1271 includes a pair of arcuate arms that facilitate rotation of needle communicating surface 1272 and retainer 1214, as discussed.

Frictional members 1262 extend from aperture plate 1265 for alignment with aperture 1266 and engagement with stylette 1216. Each frictional member 1262 may include a U-shaped arm that is spaced apart from aperture plate 1265. The U-shaped arms are spaced apart to facilitate sliding engagement with stylette 1216. Such engagement creates a frictional drag force with stylette 1216. This frictional drag force in conjunction with one of the blocking members 1240 and/or 1242 causes binding member 1264 to move with stylette 1216, which generates a canting force in retainer 1214 and inclination of aperture plate 1265. Needle communicating surface 1272 opposes the canting force of end sensing member 1271 directed to stylette 1216.

As stylette 1216 is released from engagement with needle communicating surface 1272, rotation of aperture plate 1265 causes binding surfaces 1268 to frictionally engage stylette 1216 to prevent movement thereof. Blocking members 1240, 1242 cause aperture plate 1265 to move to the binding position as forces are imposed on shield 1200 in either direction along longitudinal axis x. This maintains stylette 1216 within shield 1200 to avoid hazardous exposure to distal end 1214.

Figure 29:
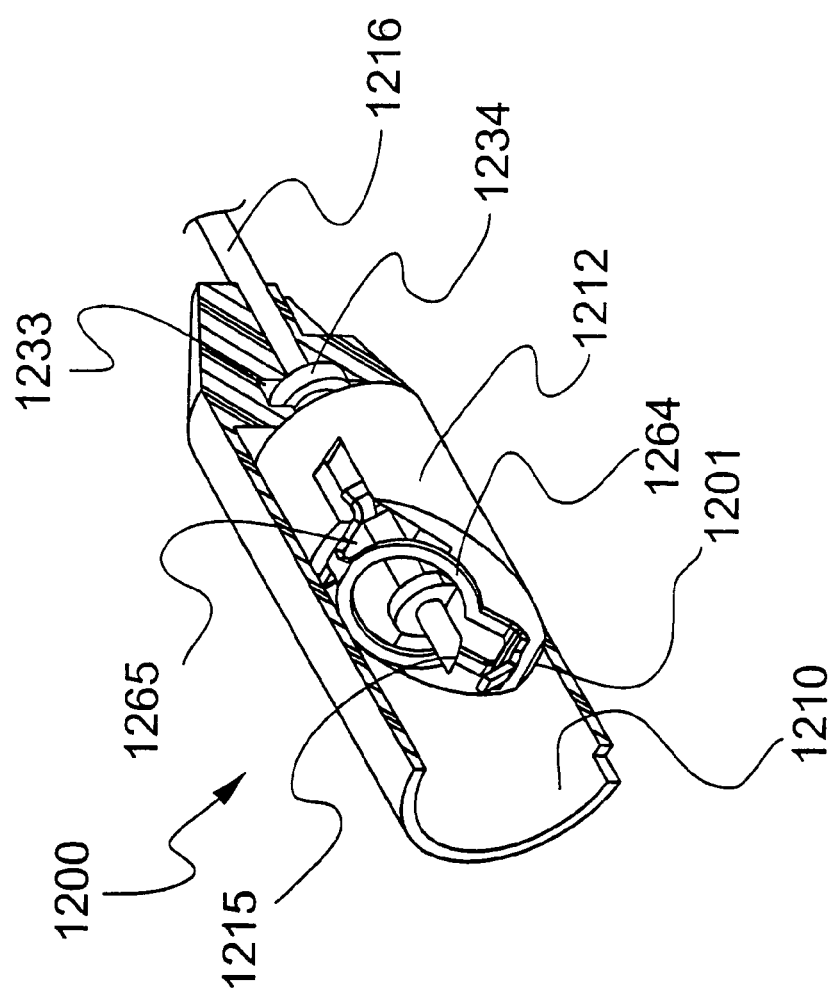
FIG. 29 is an enlarged perspective view of the housing of the medical needle shield apparatus shown in FIG. 28.
Figure 30:
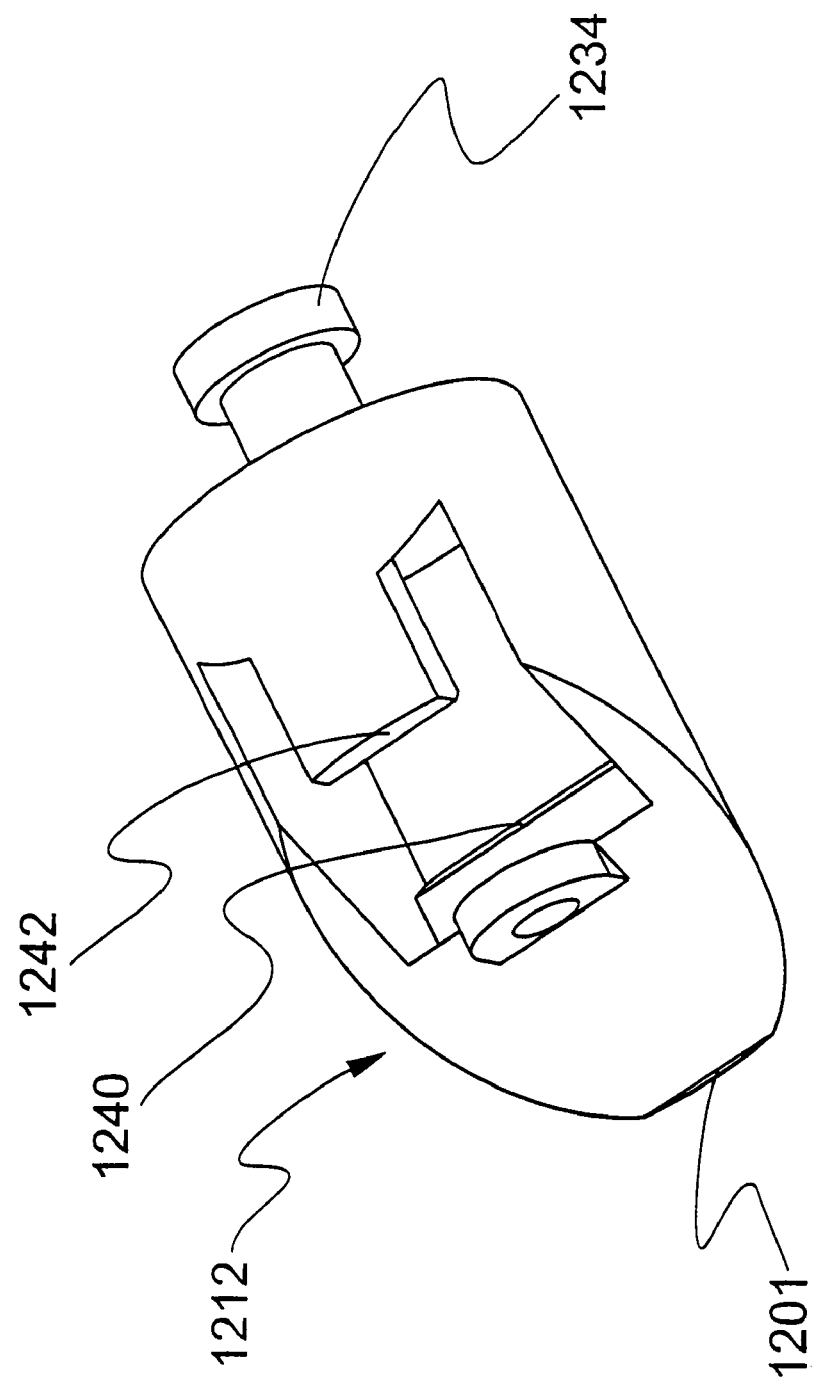
FIG. 30 is an alternate perspective view of the housing shown in FIG. 29.
Figure 31:
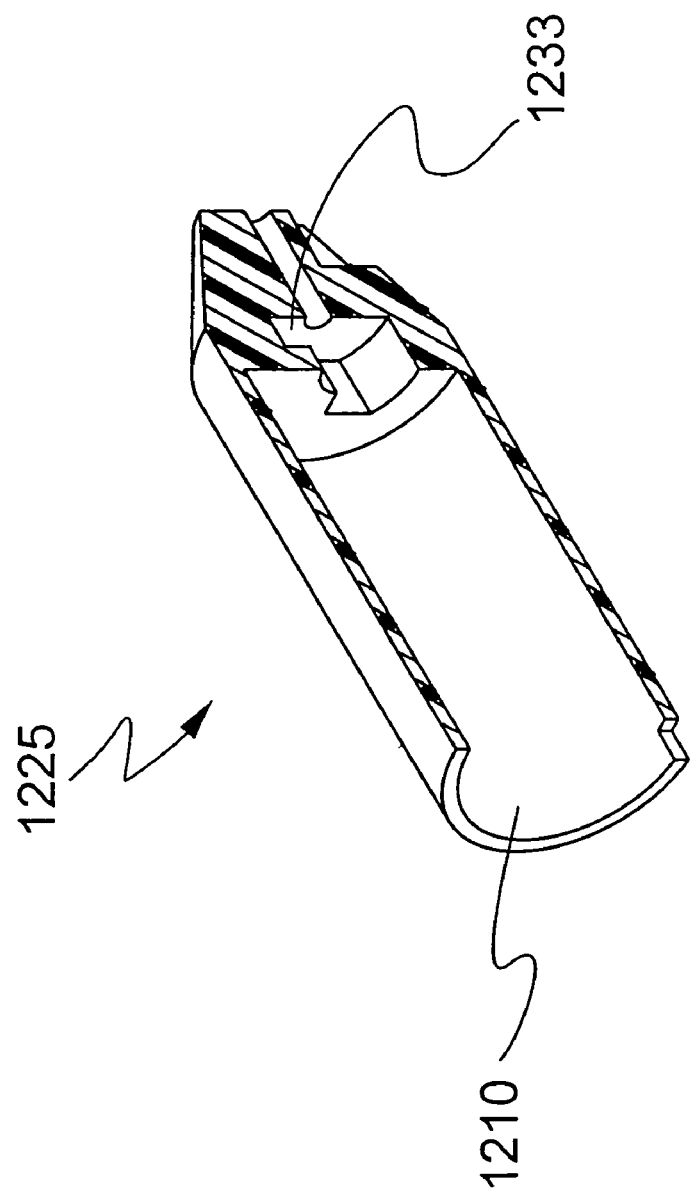
FIG. 31 is an enlarged perspective view of a gripping element of the housing shown in FIG. 28.
Figure 32:
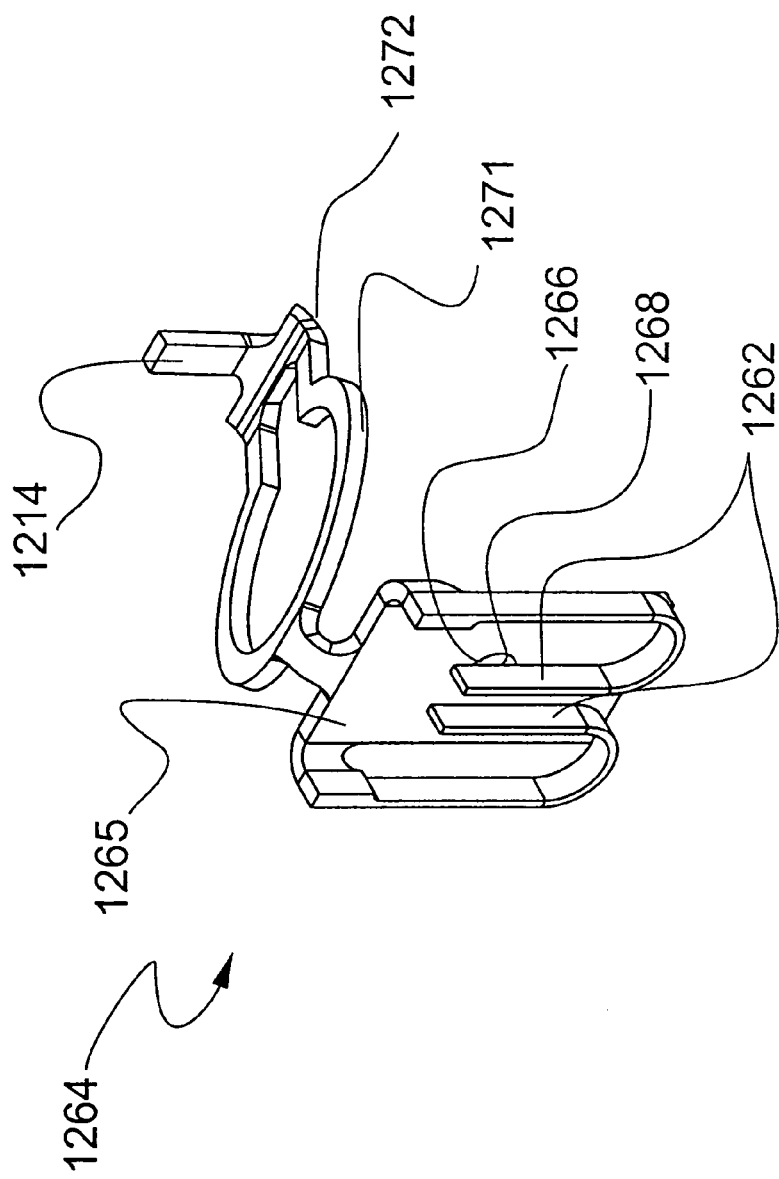
FIG. 32 is an enlarged perspective view of a binding member employed with the medical needle shield apparatus shown in FIG. 28.

As stylette 1216 is retracted and shield 1200 is extended, as shown in FIG. 29, friction members 1262 create a drag force via engagement with stylette 1216 on binding member 1264 and in conjunction with blocking member 1240 cause aperture plate 1265 to rotate in a counter-clockwise direction to the binding position. Blocking members 1240A, 1242A engage aperture plate 1265 to facilitate rotation thereof from the perpendicular position into the binding position such that binding surfaces 1268 engage stylette 1216, as discussed. This configuration prevents movement of stylette 1216.

Needle hub 1232 is mounted with needle 1217. Needle hub 1232 is releasably mounted with shield 1200 via releasable engagement with retainer 1214. Needle hub 1232 has a hub slot 1224 for receipt and engagement with retainer 1214. This configuration facilitates removal and use of needle hub 1232 and needle 1217 from shield 1200 during a medical needle application.

A flange of needle hub 1232 is concentrically supported by a control surface 1210 of an external grip element 1225, discussed below. It is contemplated that other forms of connection may be employed. Control surface 1210 engages flange 1204 for releasable support thereof. Housing 1212 may include hub stop surfaces 1201 that facilitate positioning of needle hub 1232 with housing 1212.

Retainer 1214 extends from needle communicating surface 1272 for receipt within hub slot 1224 of needle hub 1232. In association with a non-binding or sliding orientation of binding member 1264, retainer 1214 is disposed within hub slot 1224 for releasably mounting with shield 1200. As stylette 1216 is retracted and shield 1200 is extended, retainer 1214 rotates in a counter clockwise direction and disengages from hub slot 1224 to release needle hub 1232 from housing 1212.

An external grip element 1225 is disposed for rotation and enclosure of shield 1200. External grip element 1225 is mounted with handle 1218 and freely rotates relative to shield 1200 and stylette 1216 in the extended position of shield 1200. Relative rotation of external gripping element 1225 is facilitated by support at bearing openings 1233 formed in external gripping element 1225 and axles 1234, similar to those described above. In a binding position, the bearing configuration, including at least one bearing, supports rotation of external gripping element 1225 relative to shield 1200 and stylette 1216.

Figure 34:
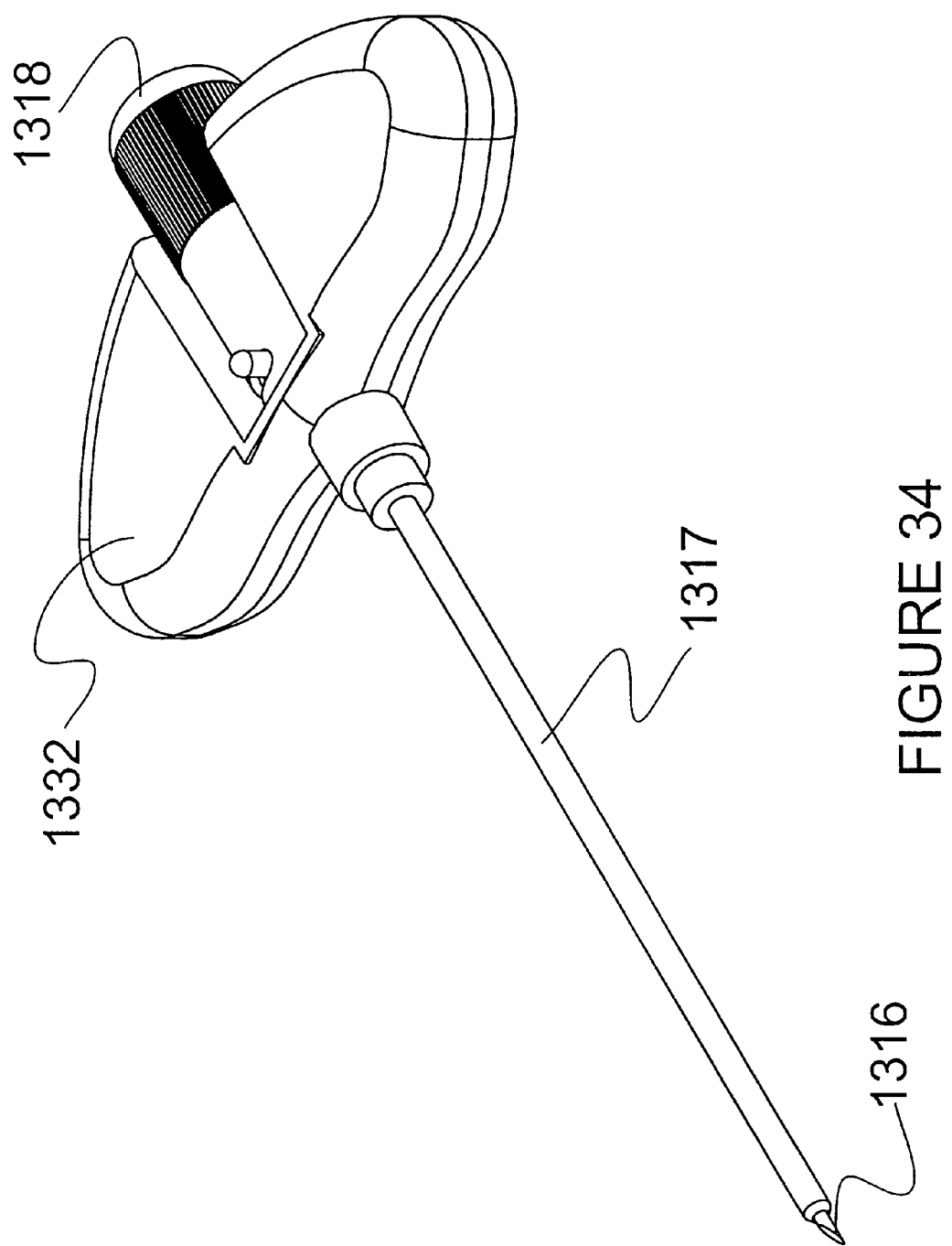
FIG. 34 is a perspective view of another embodiment of the medical needle shield apparatus shown in FIG. 28.
Figure 35:
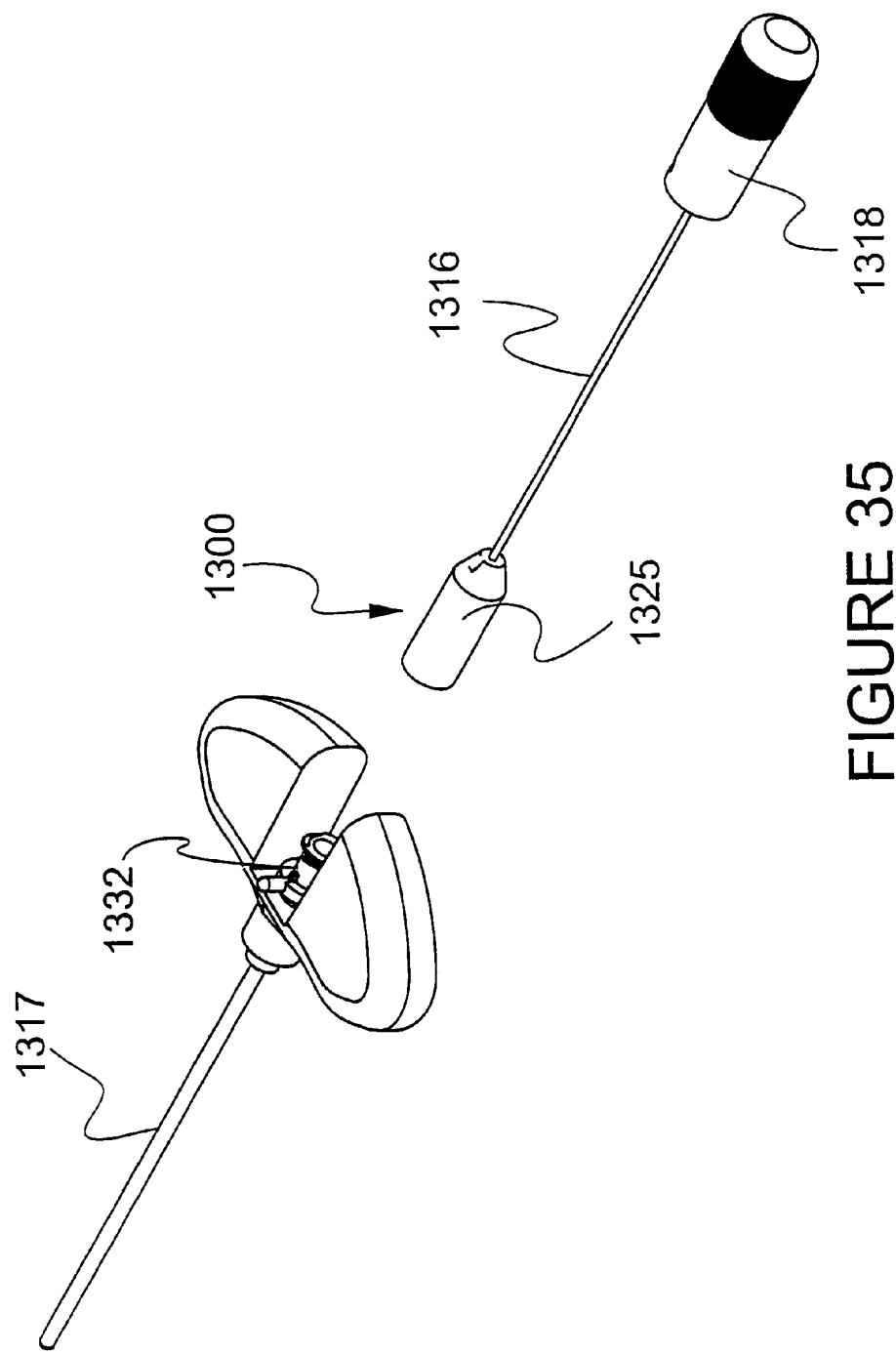
FIG. 35 is a perspective view of the medical needle shield apparatus shown in FIG. 34, with parts separated.
Figure 36:
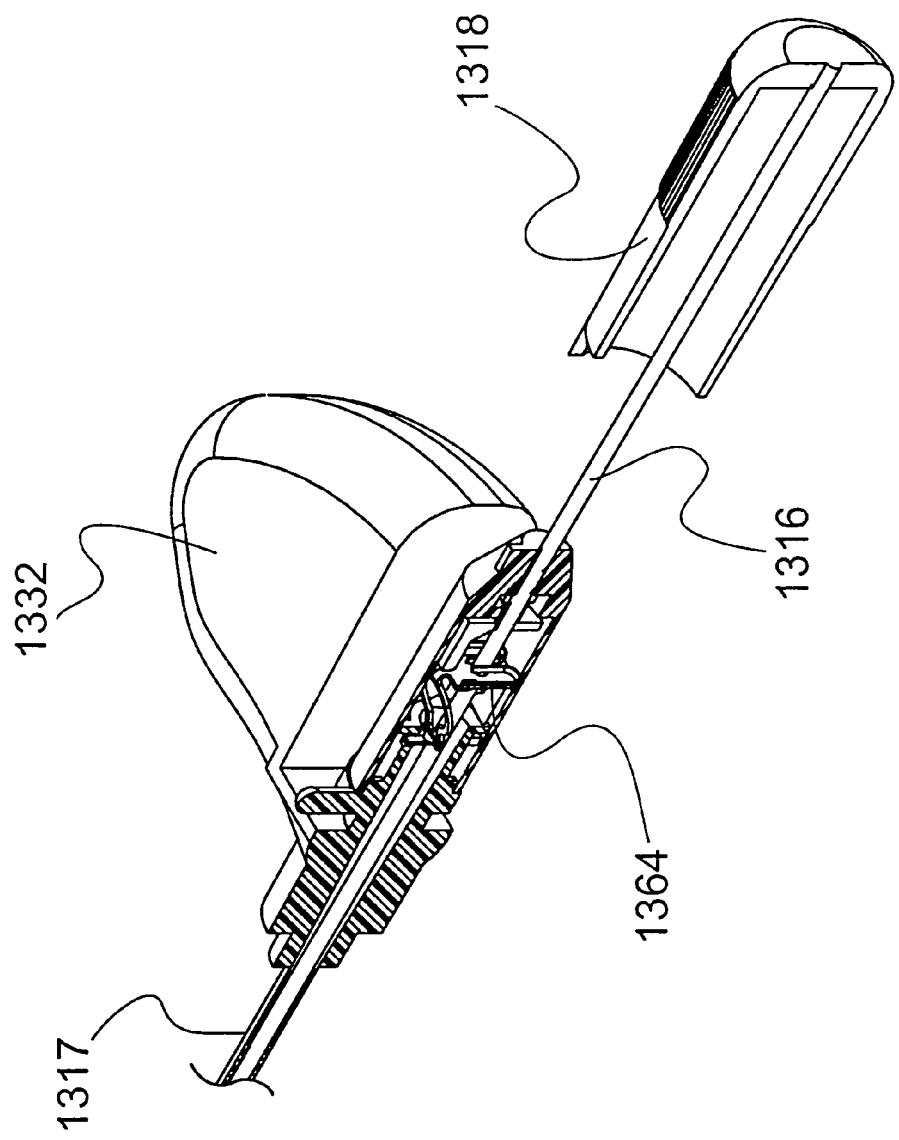
FIG. 36 is a cutaway perspective view of the medical needle shield apparatus shown in FIG. 34, in cross-section.

In another embodiment, as shown in FIGS. 34-36, the medical needle shield apparatus includes a binding member 1364 that is disposed within a shield 1300 (FIG. 35), similar to that described with regard to FIGS. 28-32, that is extensible from a retracted position to an extended position to enclose a distal end of a stylette 1316 of a needle assembly. Stylette 1316 is slideably and concentrically disposed with a needle 1317 of the needle assembly for employment therewith during a bone biopsy needle application. A stylette handle 1318 is connected to stylette 1316.

In operation, the medical needle shield apparatus, similar to that described, in accordance with the principles of the present disclosure is provided for employment with needle hub 1332. The clinician (not shown) manipulates handle 1318 such that shield 1300 is in the retracted position (FIG. 34) and binding member 1364 is in a non-binding or sliding position. Stylette 1316 is extended relative to shield 1300 such that needle hub 1332 is disposed about needle 1317 and needle hub 1332 is releasably mounted with housing 1312.

A procedure employing the medical needle shield apparatus with stylette 1316 and needle 1317 is performed by the clinician to completion.

Needle hub 1332 is releasably mounted with housing 1312. Referring to FIG. 35, stylette 1316 is retracted proximally such that shield 1300 is extended to the extended position and binding member 1364 is disposed in a binding position. Needle hub 1332 is released from shield 1300 and an external gripping element 1325 encloses shield 1300 in the extended position. This maintains stylette 1316 within shield 1300 to avoid hazardous exposure to the distal end of stylette 1316.

Figure 37:
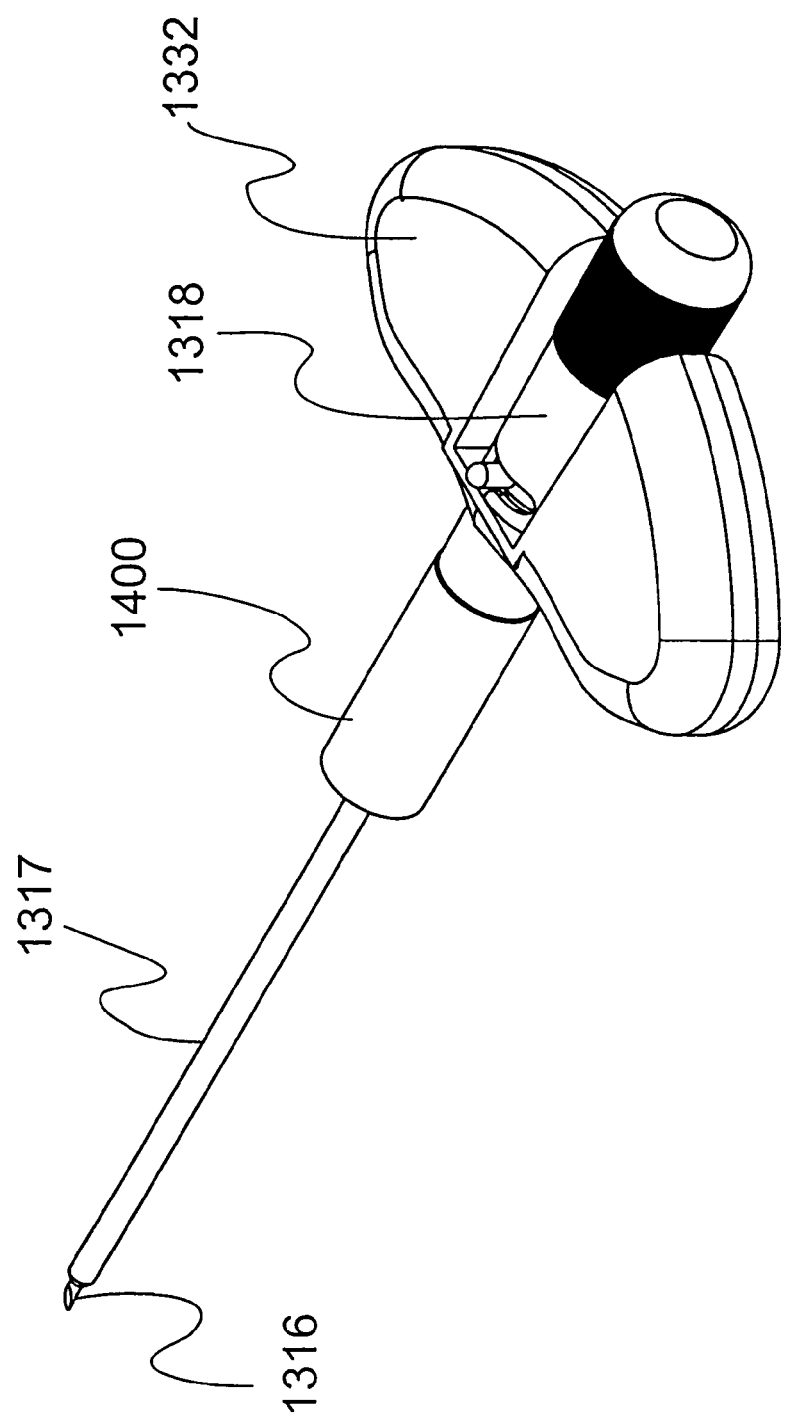
FIG. 37 is a perspective view of another embodiment of the medical needle shield apparatus shown in FIG. 34.
Figure 38:
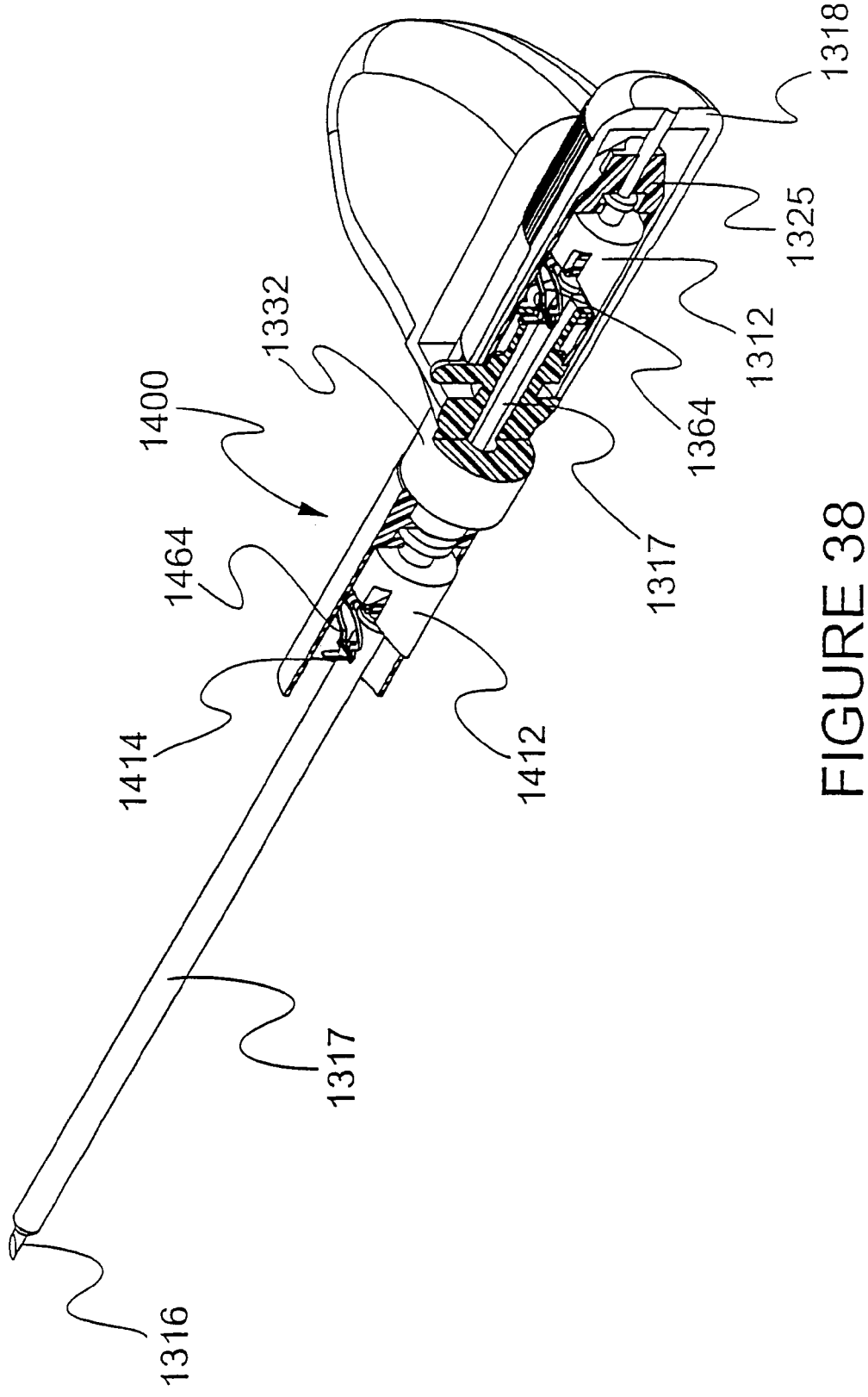
FIG. 38 is a perspective view, in part cross-section, of the medical needle shield apparatus shown in FIG. 37.
Figure 39:
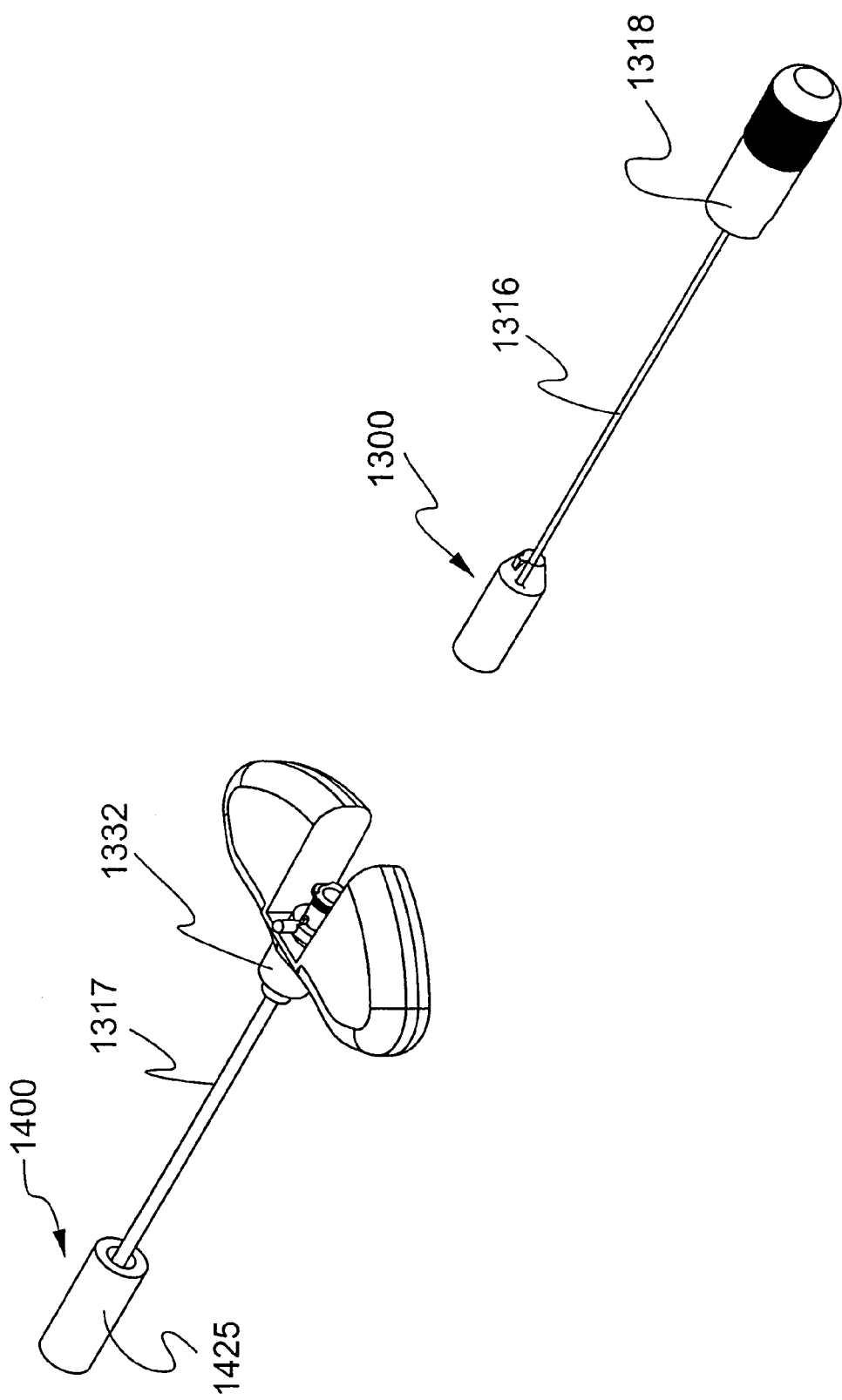
FIG. 39 is a perspective view of the medical needle shield apparatus shown in FIG. 37, with parts separated.

Alternatively, as shown in FIGS. 37-39, the medical needle shield apparatus including shield 1300 described above with regard to FIGS. 34-36, further includes a binding member 1464 that is disposed within a shield 1400, similar to that described with regard to FIGS. 28-32. Shield 1400 includes a housing 1412 that encloses binding member 1464. Shield 1400 is extensible from a retracted position to an extended position to enclose a distal end of needle 1317.

In operation, needle hub 1332 is released from shield 1300 and an external gripping element 1325 encloses shield 1300 in the extended position, as described above. An external gripping element 1425 encloses shield 1400 in the extended position. This maintains needle 1317 within shield 1400 to avoid hazardous exposure to the distal end thereof.

Figure 40:
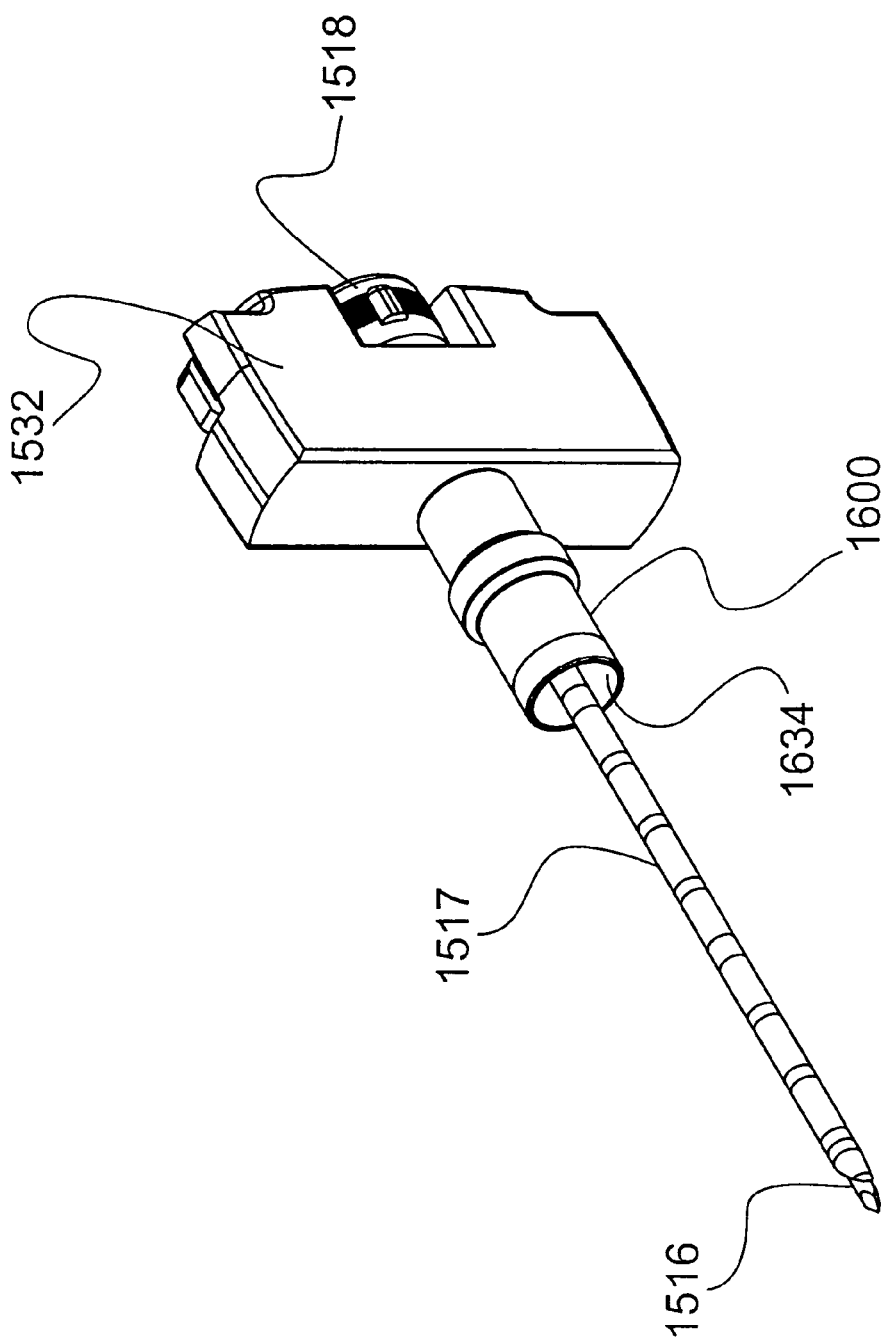
FIG. 40 is a perspective view of another embodiment of the medical needle shield apparatus shown in FIG. 1.
Figure 41:
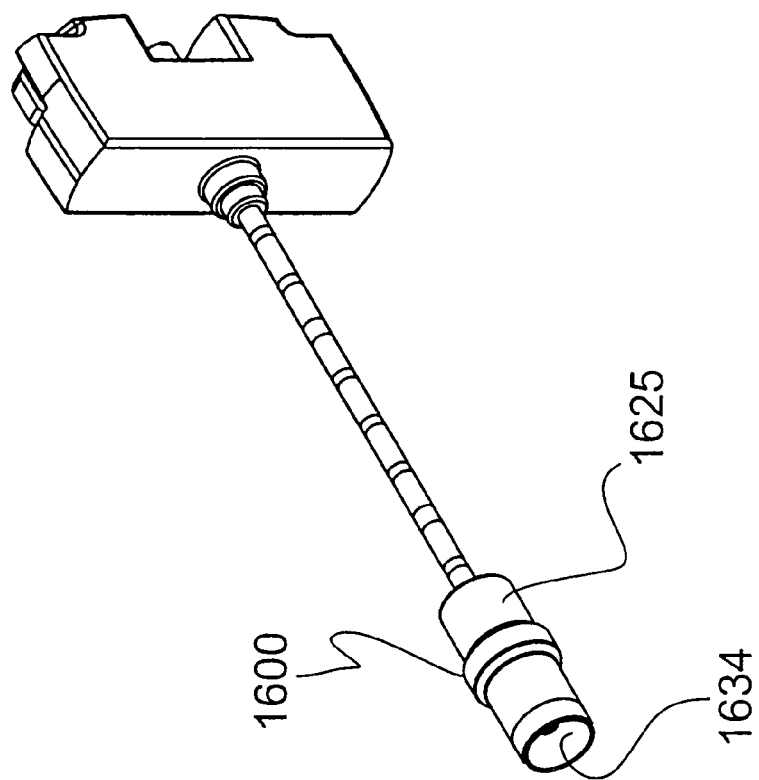
FIG. 41 is a perspective view of the medical needle shield apparatus shown in FIG. 40, with parts separated.
Figure 42:
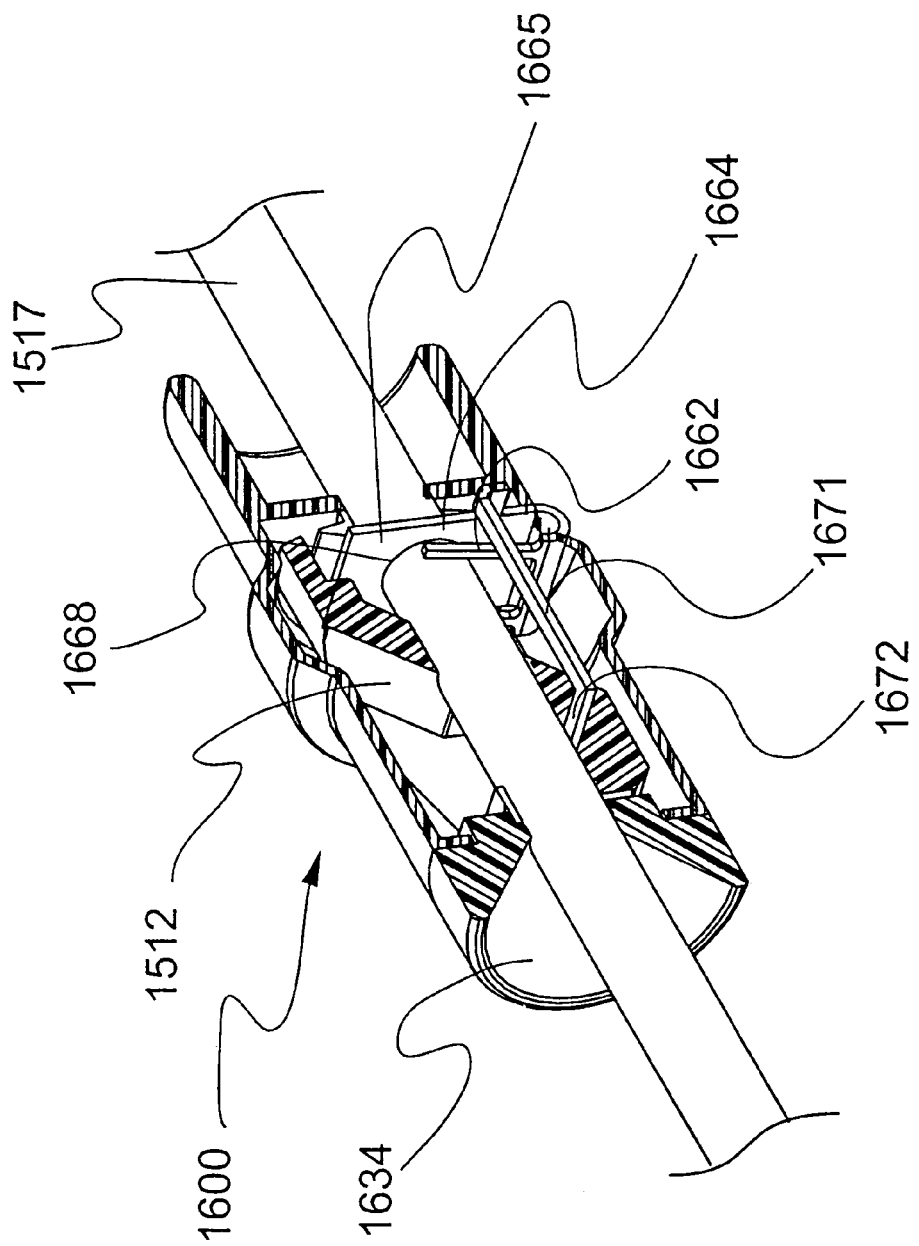
FIG. 42 illustrates a housing shown in FIG. 41 in part cross section.
Figure 43:
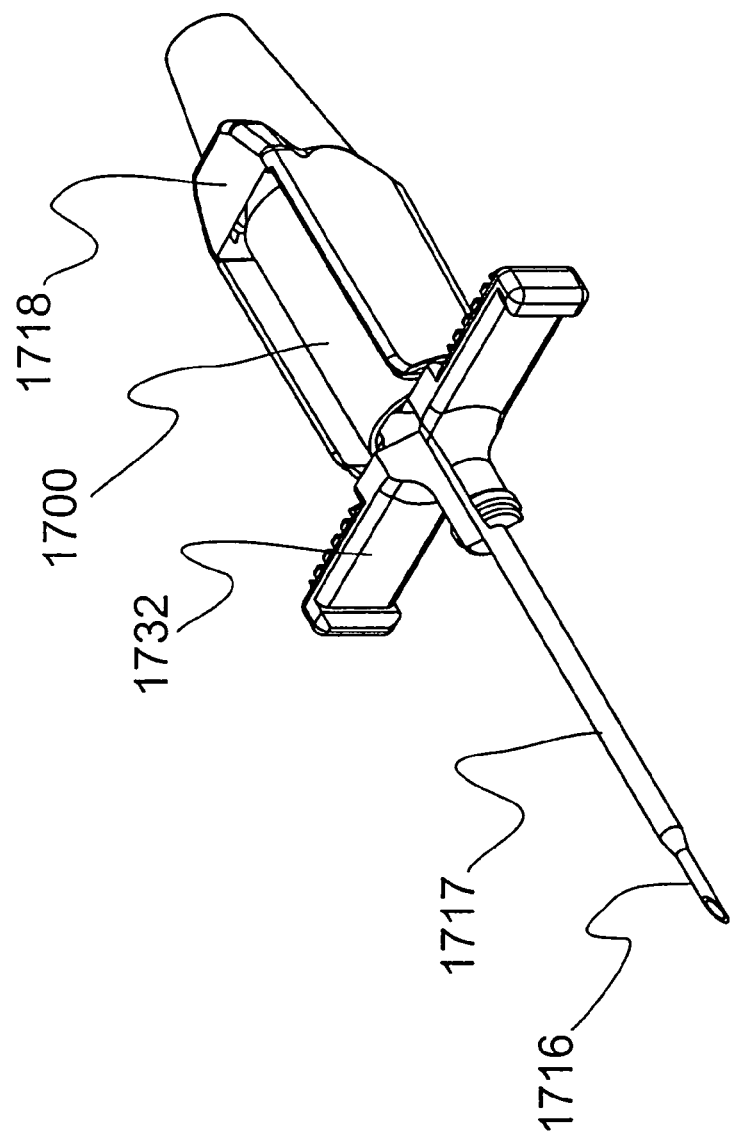
FIG. 43 is a perspective view of another embodiment the medical needle shield apparatus shown in FIG. 28.
Figure 44:
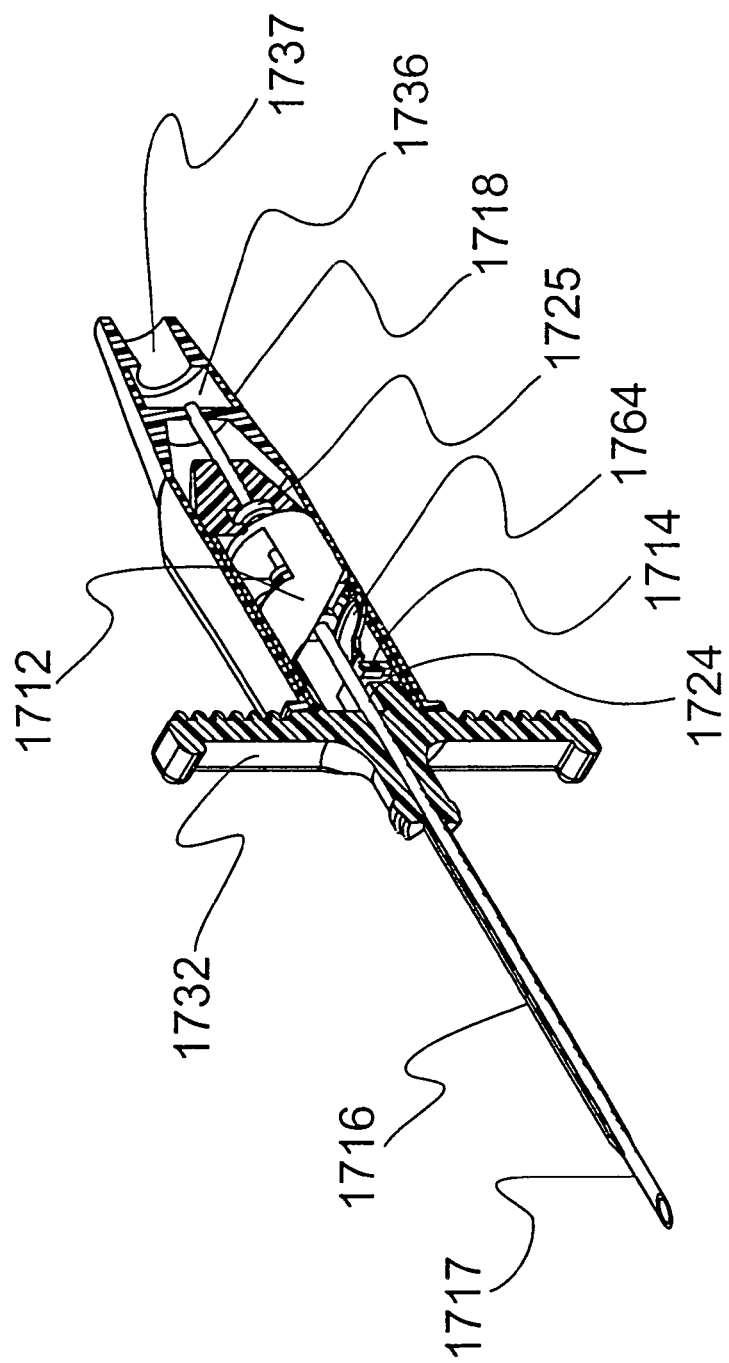
FIG. 44 is a perspective view, in a cross-section of the medical needle shield apparatus shown in FIG. 43.
Figure 45:
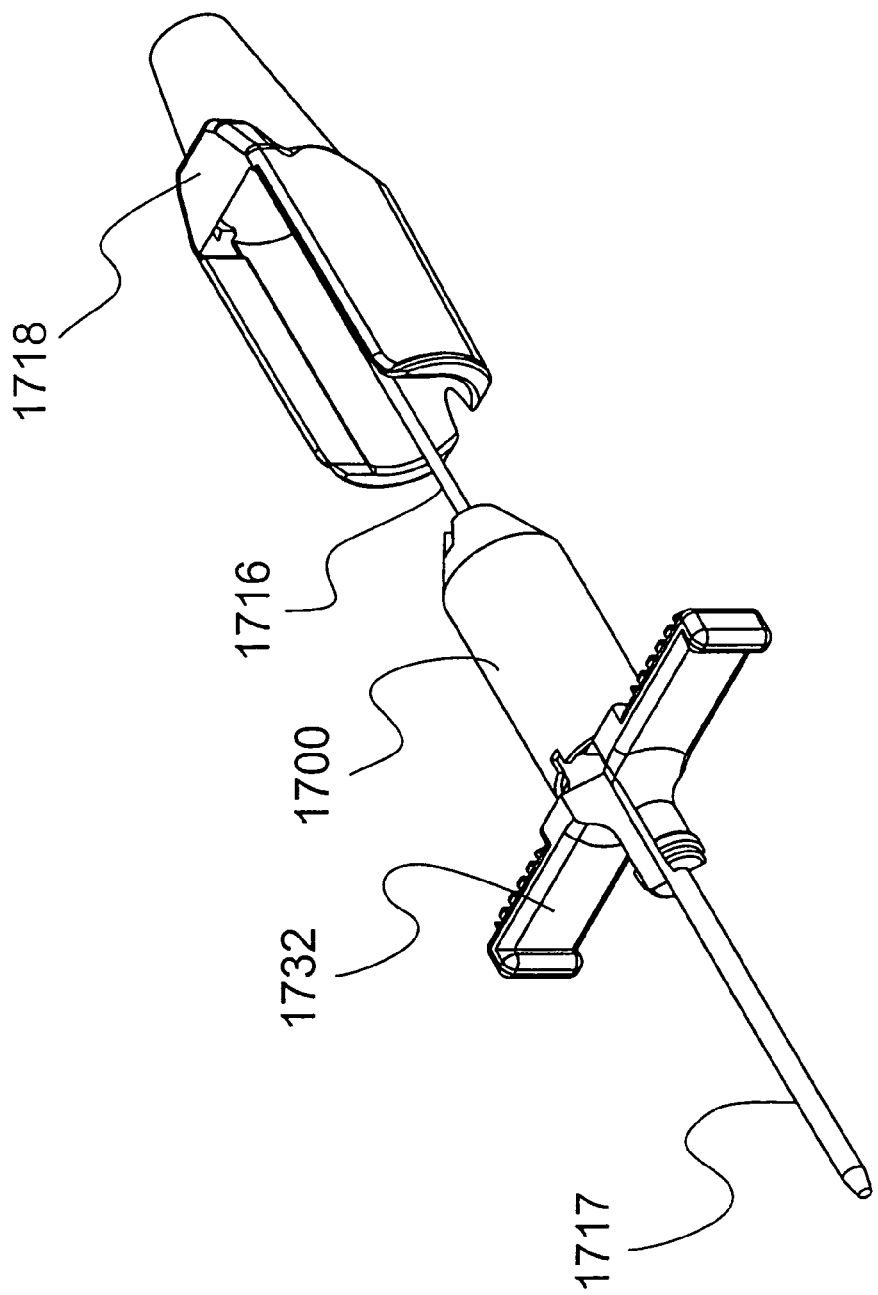
FIG. 45 is a perspective view of the medical needle shield apparatus shown in FIG. 43, with parts separated.
Figure 46:
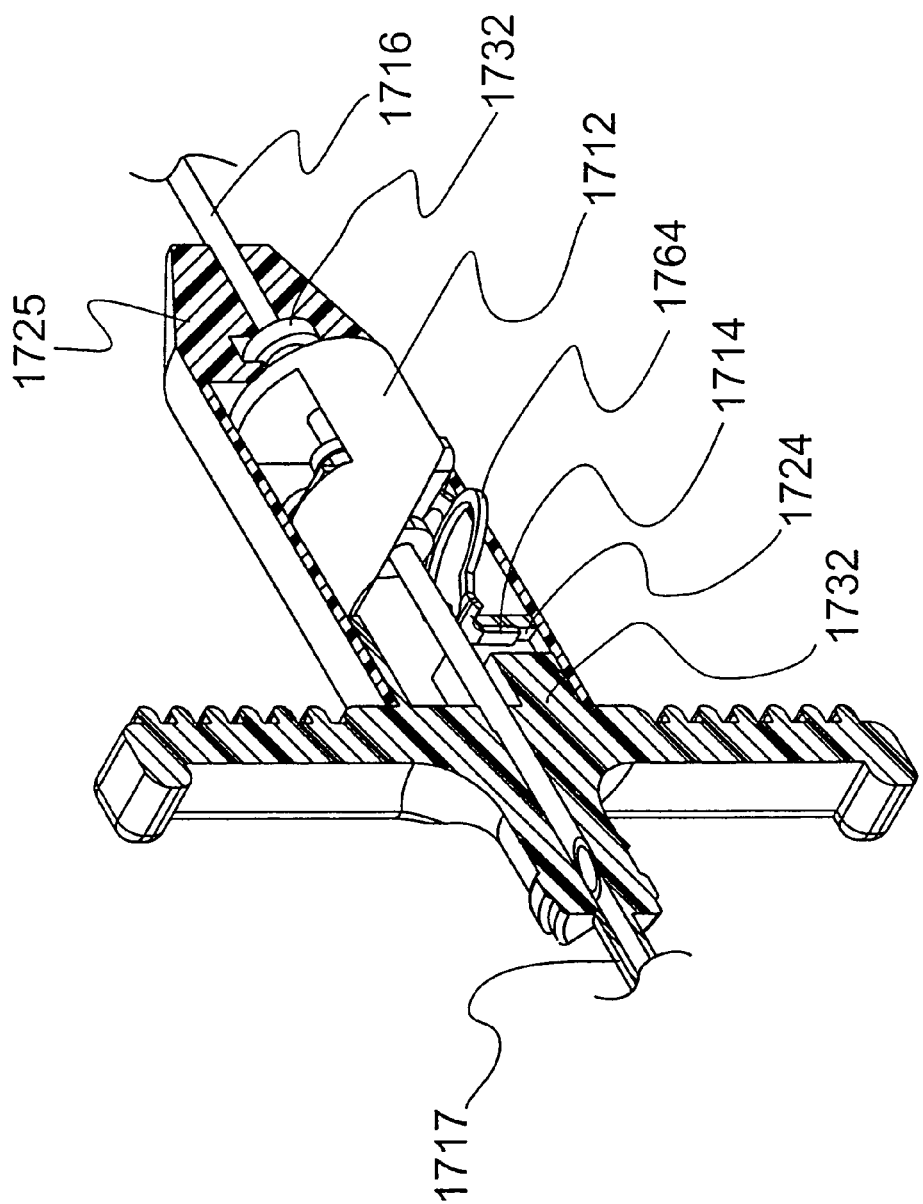
FIG. 46 is a cutaway perspective view of the medical needle shield apparatus shown in FIG. 43.

In alternate embodiment, as shown in FIGS. 40-42, the medical needle shield apparatus includes a binding member 1664 that is disposed within a shield 1600, similar to those described, that is extensible from a retracted position to an extended position to enclose a distal end of a needle 1517 of a needle assembly. A stylette 1516 is slideably and concentrically disposed with needle 1517 of the needle assembly for employment therewith during a bone biopsy needle application using a probe guide 1634. A handle 1518 is attached to stylette 1516.

Binding member 1664 is disposed within shield 1600 and defines binding surfaces 1668. Binding member 1664 includes friction members 1662 extending therefrom. Binding member 1664 has a needle communicating surface 1672 that is engageable with needle 1517 to prevent rotation of binding member 1664. Friction members 1662 are configured for slidable engagement with needle 1517 between the retracted position and the extended position such that friction members 1662 engage needle 1517 to create a drag force, similar to those described, with needle 1517.

Binding member 1664 includes an aperture plate 1665, frictional members 1662, end sensing member 1671 and needle communicating surface 1672. End sensing member 1671 facilitates rotation of needle communicating surface 1672, as discussed.

In operation, the medical needle shield apparatus, similar to that described, in accordance with the principles of the present disclosure is provided for employment with needle hub 1532. The clinician manipulates hub 1532 such that shield 1600 is in the retracted position (FIG. 40) and binding member 1664 is in a non-binding or sliding position.

Needle hub 1532 is releasably mounted with shield 1600. Referring to FIG. 41, needle 1517 is retracted proximally such that shield 1600 is extended to the extended position and binding member 1664 is disposed in a binding position. Needle hub 1532 is released from shield 1600 and an external gripping element 1625 encloses shield 1600 in the extended position. This maintains needle 1517 within shield 1600 to avoid hazardous exposure to the distal end of needle 1517.

Probe guide 1634 has a funnel configuration, integral to shield 1600, and is installed over needle 1517, which may be contaminated from a bone biopsy procedure. The funnel configuration of probe guide 1634 facilitates attachment with a probe rod 1535. Thus, shield 1600 and probe guide 1634 prevent hazardous exposure to the clinician. Probe rod 1535 is inserted into a distal end of needle 1517 and passed therethrough to force a sample (not shown) out of needle hub 1532.

In another alternate embodiment, as shown in FIGS. 43-47, the medical needle shield apparatus includes a shield 1700, similar to those described, that is extensible from a retracted position (FIG. 43) to an extended position (FIG. 47) to enclose a distal end of a needle 1716 of a needle assembly. Needle 1716 is slideably and concentrically disposed with a sheath 1717 of the needle assembly for employment therewith during a PICC introducer application. Sheath 1717 may, or may not, be splitable. Needle 1716 is a hollow bore cannula having a sharpened distal tip. Sheath 1717 is desirably fabricated from a polymeric material.

A handle 1718 is connected to Needle 1716. Handle 1718 may have a flash chamber 1736 in communication with needle 1716. A luer fitting 1737 communicates with flash chamber 1736 that facilitates connection to various medical devices via either a luer slip or luer lock attachment feature.

A binding member 1764, similar to that described with regard to FIGS. 28-32, is disposed within shield 1700. Shield 1700 includes a housing 1712 that encloses binding member 1764.

Needle hub 1732 is mounted with needle 1717. Needle hub 1732 is releasably mounted with shield 1700 via releasable engagement with a retainer 1714 of binding member 1764. Needle hub 1732 has a hub slot 1724 for receipt and engagement with binding member 1764. This configuration facilitates removal and use of needle hub 1732 and sheath 1717 from shield 1700 during a medical needle application.

A flange of needle hub 1732 is concentrically supported by a control surface of an external grip element 1725, discussed below. The control surface engages the flange for releasable support thereof. Retainer 1714 extends for receipt within a hub slot 1724 of needle hub 1732. In association with a non-binding or sliding orientation of binding member 1764, retainer 1714 is disposed within hub slot 1724 for releasably mounting with shield 1700. As needle 1716 is retracted and shield 1700 is extended, retainer 1714 rotates in a counter clockwise direction and disengages from hub slot 1724 to release needle hub 1732 from housing 1712.

An external grip element 1725 is disposed for rotation and enclosure of shield 1700. External grip element 1725 is mounted with handle 1718 and freely rotates relative to shield 1700 and needle 1716 in the extended position of shield 1700. Relative rotation of external gripping element 1725 is facilitated by support at bearing openings formed in external gripping element 1725 and axles, similar to those described above. In a binding position, the bearing configuration supports rotation of external gripping element 1725 relative to shield 1700 and needle 1716.

Figure 47:
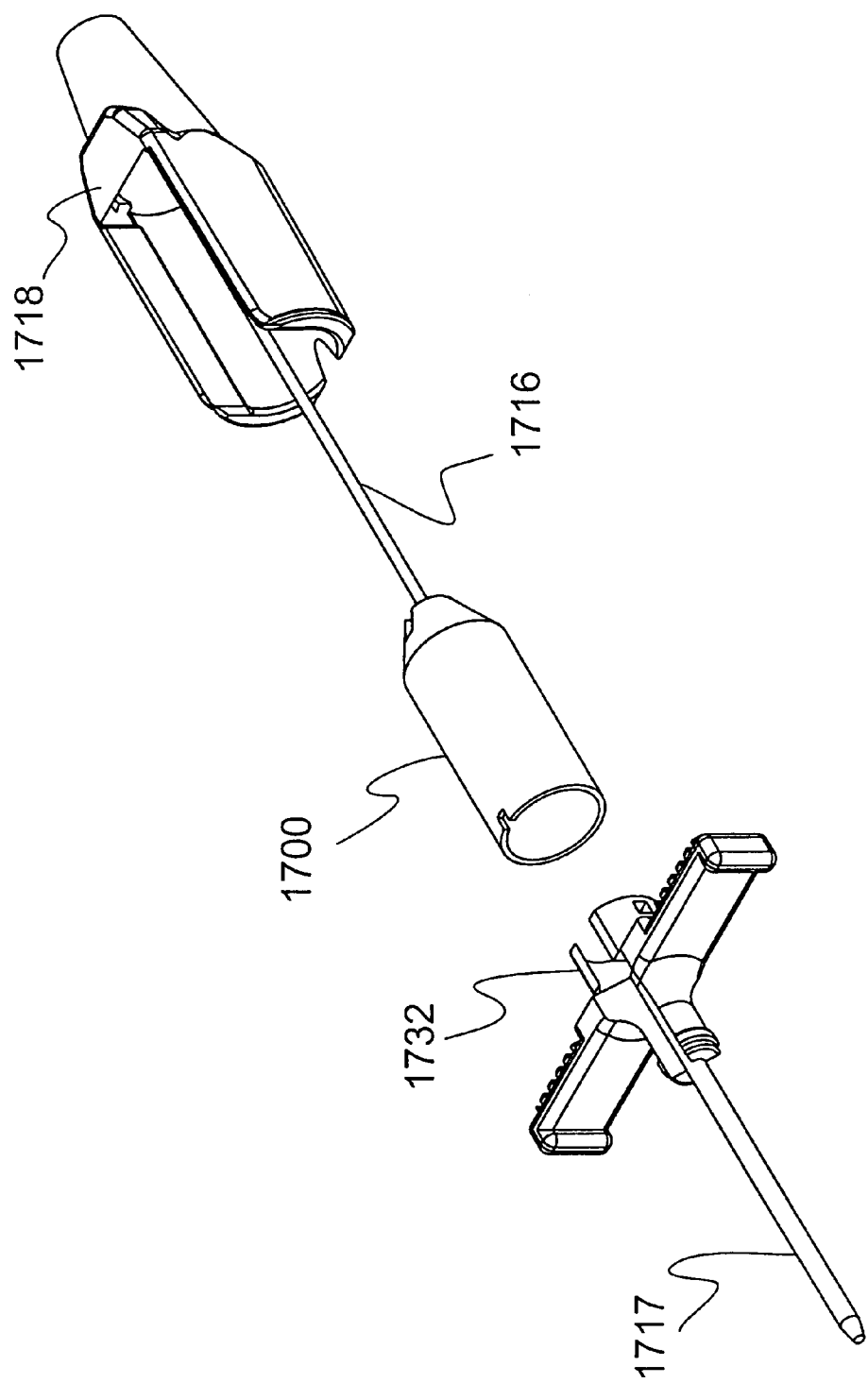
FIG. 47 is a perspective view of the medical needle shield apparatus shown in FIG. 43 with parts separated.

Referring to FIG. 47, needle 1716 is retracted proximally such that shield 1700 is extended to the extended position and binding member 1764 is disposed in a binding position. Needle hub 1732 is released from shield 1700 and shield 1700 encloses the distal end of needle 1716 in the extended position. This maintains needle 1716 within shield 1700 to avoid hazardous exposure to the distal end of needle 1716.

It is envisioned that the outer rotating housing may be comprised of multiple sections of various configurations, or may be monolithically formed, as is appropriate to the particular application.

The various shields disclosed above may be used to measure a desired insertion depth by positioning the shield along the needle at a desired insertion depth. It is also contemplated that the various shields disclosed above may be used to stabilize the needle by grasping the shield during insertion.

The invention of the present disclosure may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A medical needle shield apparatus comprising:
    a needle hub having an outer needle cannula extending therefrom to a distal end, an inner needle being disposed for slidable movement with the outer needle cannula;
    at least one shield being extensible from a retracted position to an extended position to enclose a distal end of the inner needle; and
    a binding member disposed within the shield and comprising binding surfaces that define an aperture configured for slidable receipt of the inner needle between the retracted position and the extended position,
    the binding member further comprising at least one drag inducing member such that the at least one drag inducing member engages the inner needle during slidable receipt of the inner needle to create a drag force with the inner needle,
    the binding member further comprising a needle communicating surface extending therefrom such that the needle communicating surface is engageable with the inner needle to prevent inclination of the binding member,
        wherein the drag force facilitates inclination of the binding member relative to a longitudinal axis of the inner needle once the needle communicating surface no longer contacts the distal end of the inner needle such that the binding surfaces engage the inner needle to prevent slidable movement of the shield in the extended position.

2. A medical needle shield apparatus as recited in claim 1, wherein the at least one drag inducing member defines a cavity that is substantially aligned with the aperture, the cavity being configured for slidable receipt of the needle to create the drag force with the needle.

3. A medical needle shield apparatus as recited in claim 1, wherein the binding member comprises a substantially planar aperture plate that includes the binding surfaces that form define the aperture.

4. A medical needle shield apparatus as recited in claim 3, wherein the at least one drag inducing member includes a pair of arms extending from the aperture plate, the arms having curled end portions spaced apart from the aperture plate.

5. A medical needle shield apparatus as recited in claim 4 wherein each arm comprises a deflectable member.

6. A medical needle shield apparatus as recited in claim 3, wherein the shield comprises a housing that defines at least one blocking member extending from an interior surface thereof, the aperture plate being axially movable for engagement with the at least one blocking member that facilities inclination of the binding member to a binding orientation.

7. A medical needle shield apparatus as recited in claim 1, wherein the binding member further comprises a retainer extending transversely from the needle communicating surface for releasable engagement with the needle hub.

8. A medical needle shield apparatus as recited in claim 7, wherein the needle hub defines a hub slot that is configured to receive the retainer of the binding member.

9. A medical needle shield apparatus as recited in claim 1, wherein the shield includes a housing that defines at least one blocking member extending from an interior surface thereof, the at least one blocking member being engageable with the binding member for urging the binding member to a binding orientation.

10. A medical needle shield apparatus as recited in claim 1, further comprising an external gripping element that encloses the at least one shield, the external gripping element supporting the at least one shield for relative rotational movement therewith.

11. A medical needle shield apparatus as recited in claim 10, wherein the at least one shield is supported for relative rotational movement by the external gripping element by at least one bearing.

12. A medical needle shield apparatus as recited in claim 1, wherein the inner needle is attached to a handle for manipulation thereof.

13. A medical needle shield apparatus as recited in claim 1, wherein the needle hub is releasably mountable with a housing of the at least one shield.

14. A medical needle shield apparatus as recited in claim 1, wherein the binding member comprises at least one outwardly arcuate arm that extends to the needle communicating surface.

15. A medical needle shield apparatus as recited in claim 1, further comprising a plurality of shields.

16. A medical needle shield apparatus comprising:
    a needle hub having an outer needle cannula extending therefrom, an inner needle being disposed for slidable movement with the outer needle cannula; and
    a shield being extensible from a retracted position to an extended position to enclose a distal end of the outer needle cannula, the shield defining a probe guide at a distal end thereof configured for receipt of a probe, the probe being configured for slidable movement with the outer needle cannula,
    a binding member disposed within the shield and comprising binding surfaces that define an aperture configured for slidable receipt of the outer needle cannula between the retracted position and the extended position; and
    the binding member further comprising at least one drag inducing member such that the at least one drag inducing member engages the outer needle cannula during slidable receipt of the outer needle cannula to create a drag force with the outer needle cannula,
    the binding member further comprising a needle communicating surface extending therefrom such that the needle communicating surface is engageable with the outer needle cannula to prevent inclination of the binding member,
        wherein the drag force facilitates inclination of the binding member relative to a longitudinal axis of the outer needle cannula once the needle communicating surface no longer contacts the distal end of the outer needle cannula such that the binding surfaces engage the outer needle cannula to prevent slidable movement of the shield in the extended position.

17. A medical needle shield apparatus as recited in claim 16, wherein the binding member further comprises a retainer extending transversely from the needle communicating surface for releasable engagement with the needle hub.

18. A medical needle shield apparatus as recited in claim 16, wherein the shield comprises a housing that defines at least one blocking member extending from an interior surface thereof, the binding member including an aperture plate being axially movable for engagement with the at least one blocking member that facilitates inclination of the binding member to a binding orientation.

19. A medical needle shield apparatus comprising:
a needle hub having an outer needle cannula extending therefrom to a distal end, an inner needle being disposed for slidable movement with the outer needle cannula, a handle being attached to the inner needle and defining a flash chamber in communication with the inner needle, the flash chamber having a fitting that facilitates connection to a medical device;
a shield being releasably mountable to the needle hub and extensible from a retracted position to an extended position to enclose a distal end of the inner needle, the handle being disposed adjacent the shield; and
a binding member disposed within the shield and comprising binding surfaces that define an aperture configured for slidable receipt of the inner needle between the retracted position and the extended position,
the binding member further comprising at least one drag inducing member such that the at least one drag inducing member engages the inner needle during slidable receipt of the inner needle to create a drag force with the inner needle,
the binding member further comprising a needle communicating surface extending therefrom such that the needle communicating surface is engageable with the inner needle to prevent inclination of the binding member, a retainer extending transversely from the needle communicating surface for releasable engagement with a hub slot of the needle hub,
wherein the drag force facilitates inclination of the binding member relative to a longitudinal axis of the inner needle once the needle communicating surface no longer contacts the distal end of the inner needle such that the binding surfaces engage the inner needle to prevent slidable movement of the shield in the extended position.

20. A medical needle shield apparatus as recited in claim 19, wherein the binding member further comprises a retainer extending transversely from the needle communicating surface for releasable engagement with the needle hub.

21. A medical needle shield apparatus as recited in claim 19, wherein the shield comprises a housing that defines at least one blocking member extending from an interior surface thereof, the binding member including an aperture plate being axially movable for engagement with the at least one blocking member that facilitates inclination of the binding member to a binding orientation.

22. A medical needle shield apparatus as recited in claim 19, further comprising a luer slip or luer lock attachment feature.

* * * * *